United States Patent
Zhou et al.

(10) Patent No.: US 12,065,447 B2
(45) Date of Patent: Aug. 20, 2024

(54) HETEROCYCLIC AMIDE FOR INHIBITING RIP1 KINASE AND USES THEREOF

(71) Applicant: SHANGHAI INSTITUTE OF MATERIA MEDICA, CHINESE ACADEMY OF SCIENCES, Shanghai (CN)

(72) Inventors: Bing Zhou, Shanghai (CN); Wei Tang, Shanghai (CN); Xiangbo Yang, Shanghai (CN); Huimin Lu, Shanghai (CN); Mengying Gao, Shanghai (CN); Yaxi Yang, Shanghai (CN); Huijin Feng, Shanghai (CN)

(73) Assignee: SHANGHAI INSTITUTE OF MATERIA MEDICA, CHINESE ACADEMY OF SCIENCES, Shanghai (CN)

( * ) Notice: Subject to any disclaimer, the term of this patent is extended or adjusted under 35 U.S.C. 154(b) by 0 days.

(21) Appl. No.: 18/045,149

(22) Filed: Oct. 8, 2022

(65) Prior Publication Data
US 2023/0167129 A1    Jun. 1, 2023

Related U.S. Application Data

(62) Division of application No. 17/289,642, filed as application No. PCT/CN2019/109899 on Oct. 8, 2019, now Pat. No. 11,498,927.

(30) Foreign Application Priority Data

Nov. 2, 2018 (CN) .......................... 201811301267.9
Aug. 2, 2019 (CN) .......................... 201910712428.1

(51) Int. Cl.
| | | |
|---|---|---|
| C07D 513/04 | (2006.01) |
| A61P 37/06 | (2006.01) |
| C07D 401/12 | (2006.01) |
| C07D 401/14 | (2006.01) |
| C07D 413/12 | (2006.01) |
| C07D 413/14 | (2006.01) |
| C07D 417/12 | (2006.01) |
| C07D 417/14 | (2006.01) |
| C07D 487/04 | (2006.01) |

(52) U.S. Cl.
CPC ............ *C07D 513/04* (2013.01); *A61P 37/06* (2018.01); *C07D 401/12* (2013.01); *C07D 401/14* (2013.01); *C07D 413/12* (2013.01); *C07D 413/14* (2013.01); *C07D 417/12* (2013.01); *C07D 417/14* (2013.01); *C07D 487/04* (2013.01)

(58) Field of Classification Search
CPC .................................................... C07D 513/04
USPC .................................................... 514/211.06
See application file for complete search history.

(56) References Cited

FOREIGN PATENT DOCUMENTS

| CN | 105121432 | 12/2015 |
| CN | 106573006 | 4/2017 |
| WO | 2017136727 | 8/2017 |
| WO | 2019213447 | 11/2019 |

OTHER PUBLICATIONS

Harris, P.A. et al., "Discovery of a First-in-Class Receptor Interacting Protein 1 (RIP 1)Kinase Specific Clinical Candidate (GSK2982772) for the Treatment of Inflammatory Diseases", Journal Medical Chemistry, 2017, vol. 60, pp. 1247-1261.
International Search Report and Written Opinion of International Application No. PCT/CN2019/109899 mailed on Dec. 27, 2019.

*Primary Examiner* — Kahsay Habte
(74) *Attorney, Agent, or Firm* — Ping Wang; Kalos Athena Wang PLLC

(57) ABSTRACT

The present invention relates to a heterocyclic amide inhibiting RIP1 kinase and the use thereof, and specifically, to a compound of formula I, its pharmaceutically acceptable salts, stereoisomers, enantiomers, diastereomers, atropisomers, optical isomers, racemates, polymorphs, solvates or isotopically labeled compounds, a pharmaceutical composition comprising the compound, and the pharmaceutical use thereof. The compound is particularly effective for treatment of diseases or disorders mediated by RIP1 kinase.

Formula I

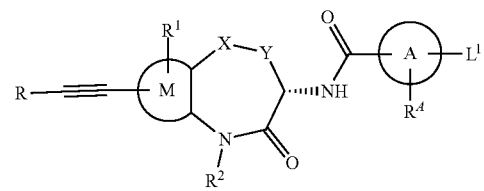

9 Claims, 10 Drawing Sheets

HETEROCYCLIC AMIDE FOR INHIBITING RIP1 KINASE AND USES THEREOF

This application is a divisional application of U.S. patent application Ser. No. 17/289,642, filed Apr. 28, 2021, which claims priority to International Patent Application No. PCT/CN2019/109899, filed Oct. 8, 2019. The entirety of all of the aforementioned applications is incorporated herein by reference.

TECHNICAL FIELD

The present invention relates to a heterocyclic amide compound and the use thereof. Specifically, the present invention relates to a heterocyclic amide inhibiting RIP1 kinase and the use thereof.

BACKGROUND ART

Receptor interacting protein 1 (RIP) kinase, originally called RIP, is a TKL family serine/threonine protein kinase involved in innate immune signal transduction. RIP1 kinase is a protein-containing RHIM domain, which has an N-terminal kinase domain and a C-terminal death domain. The death domain of RIP mediates the interaction with other proteins containing the death domain, including Fas and TNFR-1. TRAIL-R1 and TRAIL-R2 and TRADD, while the RHIM domain are very critical for binding to other RHIM domain-containing proteins, such as TRIF, DAI and RIP3, and various functions are achieved through these interactions. RIP1 is a central regulator transduced by cell signal, and involves in mediating both pro-survival and pro-grammed cell death pathways, as discussed in detail below.

The role of RIP in transduction of cell signaling has been evaluated under different conditions, but the best understanding can be obtained in mediate signal downstream the death receptor TNFR1. The achievement of TNFS linkage through TNF leads to oligomerization, thus recruiting a variety of proteins, including linear K63-linked polyubiquitinated RIP1. TRAF2/5, TRADD and cIPAs, to the cytoplasmic tail of the receptor. The complex dependent on RIP 1 acts as a scaffold protein (that is, kinase-independent), is called Complex I, and provides a platform for pro-survival signal transduction by activating the NF-κB and MAP kinase pathways. Further, in the condition of promoting RIP deubiquitin, the binding of TNF with its receptor (e.g. through A20 and CYLD protein or cIAP inhibition) will lead to receptor internalization and formation of Complex II or DISC (death-inducing signaling complex). The formation of DISC (including RIP1, TRADD, FADD and Caspase 8) leads to the activation of Caspase 8, and also initiates programmed apoptotic cell death in a non-RIP kinase-dependent manner. Apoptosis is largely a quiescent form of cell death, which participates in routine processes such as development and homeostasis of cells.

Under the conditions of forming DISC, expressing RIP3, and inhibiting apoptosis (such as FADD/caspase 8 deletion, caspase inhibition, or viral infection), there may be a third kind of RIP1 kinase dependency. Now, RIP3 can enter this complex, achieve phosphorylation through RIP, and initiate caspase-independent programmed necrosis cell apoptosis through activation of MLKL and PGAM5. In contrast to apoptosis, programmed necrosis (not to be confused with unprogrammed passive necrosis) results in the Damage-associated molecular pattern (DAMP) released from the cell. These DAMPs can provide a "danger signal" to surrounding cells and tissues, and induce pro-inflammatory responses, including inflammasome activation, cytokine production and cell recruitment.

By using RIP3 knockout mice (in which RIP1-mediated programmed necrosis is completely blocked) and Necrotatin-1 (a tool inhibitor of RIP1 kinase activity with poor oral bioavailability), it has been demonstrated that the abnormal regulation of RIP1 kinase-mediated programmed cell death is related to various inflammations. RIP3 knockout mice have been shown to be resistant to inflammatory bowel diseases (including ulcerative colitis and Crohn's disease), photoreceptor cell necrosis induced by retinal detachment, retinitis pigmentosa, bombesin-induced acute pancreatitis and sepsis/Systemic Inflammatory Response Syndrome (SIRS). It has been shown that Necrotatin-1 can effectively alleviate ischemic brain injury, retinal ischemia/reperfusion injury, Huntington's disease, renal ischemia-reperfusion injury, cisplatin-induced kidney injury and traumatic brain injury. Other diseases or disorders that are at least partially regulated by RIP1-dependent apoptosis, necrosis or cytokine production include blood and solid organ malignancies, bacterial infections and viral infections, Gaucher disease, etc.

There is still a need for an effective, selective, small molecule inhibitor of RIP 1 kinase activity that can block RIP1-dependent cell necrosis, so as to provide a therapeutic effect for diseases or events related to DAMP, cell death and/or inflammation.

SUMMARY OF THE INVENTION

In one aspect, the present invention provides a compound of formula (I), a pharmaceutically acceptable salt, stereoisomer, enantiomer, diastereomer, atropisomer, optical isomer, racemate, polymorph, solvate or isotopically labeled compound thereof:

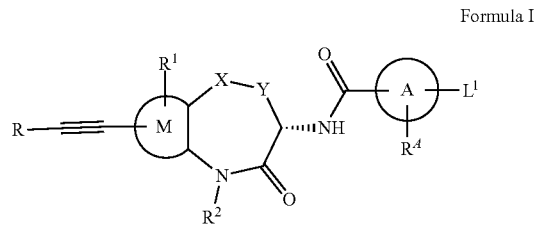

Formula I wherein

X is O, S, SO,

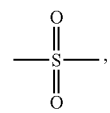

NH, CO, CH$_2$, CF$_2$, CH(CH$_3$), CH(OH) or N(CH$_3$);

Y is C$_1$-C$_2$ alkylene (i.e. CH$_2$ or CH$_2$CH$_2$);

Ring A is a benzene ring, a 5-6 membered heteroaromatic ring, a 5-6 membered non aromatic heterocyclic ring or

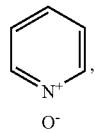

and the carbonyl moiety and $L^1$ connected to Ring A are in meta-positions;

$R^A$ is H or $C_1$-$C_4$ alkyl;

$L^1$ is $C_3$-$C_6$ alkyl, $C_3$-$C_6$ alkoxy, halogenated $C_3$-$C_6$ alkoxy, $C_3$-$C_6$ alkenyl, $C_3$-$C_6$ alkenyloxy, or

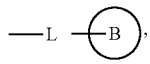

wherein

L is O, S, NH, N(CH$_1$), CH$_2$, CH$_2$CH$_2$, CH(CH$_3$), CHF, CF$_2$, CH$_2$O, CH$_2$N(CH$_3$), CH$_2$NH or CH(OH);

Ring B is a $C_3$-$C_6$ cycloalkyl, phenyl, 5-6 membered heteroaryl or 5-6 membered non-aromatic heterocyclyl, wherein the $C_3$-$C_6$ cycloalkyl, the phenyl, the 5-6 membered heteroaryl and the 5-6 membered non-aromatic heterocyclyl are each independently unsubstituted or substituted with one or two substituents each independently selected from the group consisting of halogen, $C_1$-$C_4$ alkyl, halogenated $C_1$-$C_4$ alkyl, $C_1$-$C_4$ alkoxy, halogenated $C_1$-$C_4$ alkoxy, nitro and $C_1$-$C_4$ alkyl C(O)—;

$R^2$ is H or CH$_3$;

Ring M is independently a $C_6$-$C_{30}$ aromatic ring or a 5-10 membered heteroaromatic ring;

$R^1$ representative 1-3 substituents each independently being H, halogen, —OH, —CN, —COOH, $C_1$-$C_6$ alkyl, $C_1$-$C_6$ haloalkyl, $C_1$-$C_6$ alkoxy, $C_1$-$C_6$ haloalkoxy, $C_2$-$C_{10}$ alkoxyalkyl, $C_2$-$C_{10}$ haloalkoxyalkyl, $C_1$-$C_6$ hydroxyalkyl, —B(OH)$_2$, —S(O)$_{n1}$R$^a$, —N(R$^a$)$_2$, —C(=O)N(R$^a$)$_2$, —NHC(=O)R$^a$, —NHC(=O)OR$^a$, —NHC(=O)C(=O)N(R$^a$)$_2$, —NHC(=O)C(=O)OR$^a$, —NHC(=O)N(R$^a$)$_2$, —NHC(=O)NR$^a$C(=O)N(R$^a$)$_2$, —NHC(=O)NR$^a$S(O)$_2$OR$^a$, —NHC(=O)NR$^a$S(O)$_2$N(R$^a$)$_2$, —NHC(=S)N(R$^a$), —NHC(=N—C≡N)NR$^a$, —NHC(=N—C≡N)SR$^a$, —NHS(O)$_{n1}$R$^a$, M$^a$, —(C$_1$-C$_6$ alkylene)-B(OH)$_2$, —(C$_1$-C$_6$ alkylene)-S(O)$_{n1}$R$^a$, —(C$_1$-C$_6$ alkylene)-N(R$^a$)$_2$, —(C$_1$-C$_6$ alkylene)-C(=O)N(R$^a$)$_2$, —(C$_1$-C$_6$ alkylene)—NHC(=O)R$^a$, —(C$_1$-C$_6$ alkylene)-NHC(=O)OR$^a$, —(C$_1$-C$_6$ alkylene)-NHC(=O)C(=O)N(R$^a$)$_2$, —(C$_1$-C$_6$ alkylene)-NHC(=O)C(=O)OR$^a$, —(C$_1$-C$_6$ alkylene)-NHC(=O)N(R$^a$)$_2$, —(C$_1$-C$_6$ alkylene)-NHC(=O)NR$^a$C(=O)N(R$^a$)$_2$, —(C$_1$-C$_6$ alkylene)-NHC(=O)NR$^a$S(O)$_2$OR$^a$, —(C$_1$-C$_6$ alkylene)-NHC(=O)NR$^3$S(O)$_2$N(R$^3$)$_2$, —(C$_1$-C$_6$ alkylene)-NHC(=S)N(R$^a$)$_2$, —(C$_1$-C$_6$ alkylene)-NHC(=N—C≡N)NR$^a$, —(C$_1$-C$_6$ alkylene)-NHC(=N—C≡N)SR$^a$, —(C$_1$-C$_6$ alkylene)-NHS(O)$_{n1}$R$^a$, —(C$_1$-C$_6$ alkylene)-M$^a$, —OM$^a$, —SM$^a$, or —N(R$^a$)M$^a$;

R$^a$ at each occurrence is independently hydrogen, $C_1$-$C_6$ alkyl, $C_6$-$C_{10}$ aryl, 5-10 membered heteroaryl, 3-10 membered non-aromatic heterocyclyl, $C_3$-$C_{10}$ cycloalkyl, or $C_5$-$C_{10}$ cycloalkenyl, wherein the $C_1$-$C_6$ alkyl, the $C_6$-$C_{10}$ aryl, the 5-10 membered heteroaryl, the 3-10 membered non-aromatic heterocyclyl, the $C_3$-$C_{10}$ cycloalkyl, and the $C_5$-$C_{10}$ cycloalkenyl are each independently unsubstituted or substituted with one or two selected from the group consisting of amino, hydroxyl, $C_1$-$C_4$ alkoxy, $C_1$-$C_6$ alkyl, $C_3$-$C_{10}$ cycloalkyl, and CN;

M$^a$ at each occurrence is independently $C_6$-$C_{10}$ aryl, 5-10 membered heteroaryl, 3-10 membered non-aromatic heterocyclyl, $C_3$-$C_{10}$ cycloalkyl, or $C_3$-$C_{10}$ cycloalkenyl, wherein the $C_6$-$C_{10}$ aryl, the 5-10 membered heteroaryl, the 3-10 membered non-aromatic heterocyclyl, the $C_3$-$C_{10}$ cycloalkyl, and the $C_3$-$C_{10}$ cycloalkenyl are each independently unsubstituted or substituted with one or two selected from the group consisting of halogen, $C_1$-$C_4$ alkyl, $C_1$-$C_4$ alkoxy, and —CN;

n1 at each occurrence is independently 0, 1 or 2;

R is each independently hydrogen, $C_1$-$C_{10}$ alkyl, $C_5$-$C_{10}$ aryl, 5-10 membered heteroaryl, 3-10 membered non-aromatic heterocyclyl, $C_3$-$C_{10}$ cycloalkyl, or $C_3$-$C_{10}$ cycloalkenyl, wherein the $C_1$-$C_{10}$ alkyl, the $C_6$-$C_{10}$ aryl, the 5-10 membered heteroaryl, the 3-10 membered non-aromatic heterocyclyl, the $C_3$-$C_{10}$ cycloalkyl, and the $C_3$-$C_{10}$ cycloalkenyl are each independently unsubstituted or substituted with 1 to 4 M$^d$s;

M$^d$ at each occurrence is independently $C_1$-$C_6$ alkyl, $C_2$-$C_6$ alkenyl, $C_2$-$C_6$ alkynyl, halogen, $C_1$-$C_6$ haloalkyl, —CN, NO$_2$, SCF$_3$, oxo, —OM$^e$, —OC(O)M$^h$, —OC(O)NM$^f$M$^g$, —SM$^e$, —S(O)$_2$M$^e$, —S(O)$_2$NM$^f$M$^g$, —C(O)M$^e$, —C(O)-(5-10 membered monocyclic heterocyclic ring), —C(O)-(5-10-membered monocyclic heteroaryl), —C(O)OM$^e$, —C(O)NM$^f$M$^g$, —NM$^f$M$^g$, —N(M$^e$)C(O)M$^h$, —N(M$^e$)S(O)$_2$M$^h$, —N(M$^e$)C(O)OM$^h$, —N(M)C(O)NM$^f$M$^g$, —(C$_1$-C$_6$ alkylene)-OM$^e$, —(C$_1$-C$_6$ alkylene)-OC(O)M$^h$, —(C$_1$-C$_6$ alkylene)-OC(O)NM$^f$M$^g$, —(C$_1$-C$_6$ alkylene)-S(O)$_2$M$^e$, —(C$_1$-C$_6$ alkylene)-S(O)$_2$NM$^f$M$^g$, —(C$_1$-C$_6$ alkylene)-C(O)M$^e$, —(C$_1$-C$_6$ alkylene)-C(O)OM$^e$, —(C$_1$-C$_6$ alkylene)-C(O)NM$^f$M$^g$, —(C$_1$-C$_6$ alkylene)-NM$^f$M$^g$, —(C$_1$-C$_6$ alkylene)-N(M$^e$)C(O)M$^h$, —(C$_1$-C$_6$ alkylene)-N(M$^e$)S(O)$_2$M$^h$, —(C$_1$-C$_6$ alkylene)-N(M$^e$)C(O)OM$^h$, —(C$_1$-C$_6$ alkylene)-N(M$^e$)C(O)NM$^f$M$^g$, —(C$_1$-C$_6$ alkylene)-CN, $C_6$-$C_{10}$ aryl, 5-10 membered heteroaryl, 3-10 membered non-aromatic heterocyclyl, $C_3$-$C_{10}$ cycloalkyl, or $C_3$-$C_{10}$ cycloalkenyl, wherein the $C_6$-$C_{10}$ aryl, the 5-10 membered heteroaryl, the 3-10 membered non-aromatic heterocyclyl, the $C_3$-$C_{10}$ cycloalkyl and the $C_3$-$C_{10}$ cycloalkenyl are each independently unsubstituted or substituted with one or two substituents each independently selected from the group consisting of halogen, $C_1$-$C_4$ alkyl, $C_1$-$C_4$ alkoxy, and —CN;

M$^e$, M$^f$, M$^g$ and M$^h$ at each occurrence are each independently hydrogen, $C_1$-$C_6$ alkyl, $C_1$-$C_6$ haloalkyl, $C_3$-$C_{10}$ cycloalkyl, $C_6$-$C_{10}$ aryl, 5-10 membered heteroaryl, or 3-10 membered non-aromatic heterocyclyl wherein the $C_1$-$C_6$ alkyl, the $C_3$-$C_{10}$ cycloalkyl, the $C_6$-$C_{10}$ aryl, the 5-10 membered heteroaryl, and the 3-10 membered non-aromatic heterocyclyl are each independently unsubstituted or substituted with one or two substituents each independently selected from the group consisting of halogen, hydroxy, $C_1$-$C_4$ alkyl, $C_1$-$C_4$ alkoxy, —CN, —S(O)$_2$(C$_1$-C$_4$ alkyl), and —C(O)(C$_1$-C$_4$ alkyl); or two M$^d$s together with the ring atoms to which they are connected form a 3-8 membered saturated or unsaturated ring;

more specifically, two M$^d$s on the same carbon together with the ring atom to which they are connected may form a 3-8 membered saturated or unsaturated ring, so as to form a Spiro ring structure;

two $M^d$s on adjacent carbons together with the ring atoms to which they are connected may form a 3-8 membered saturated or unsaturated ring, so as to form a fused ring structure;

two $M^d$s on meta carbons together with the ring atoms to which they are connected may form a 3-8 membered saturated or unsaturated ring, so as to form a bridged ring structure.

Preferably, the compound of formula I is a compound represented by formula Ia or Ib:

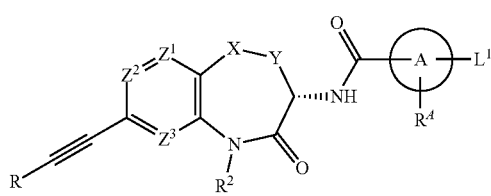

Ia

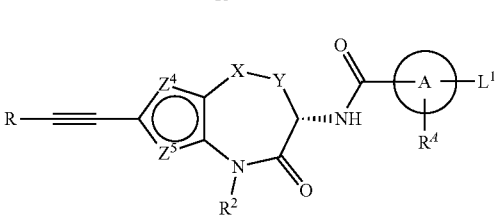

Ib $Z^1$ is N, CH, C(CH$_3$), or C(halogen);

$Z^2$ is N or CR$^1$;

$Z_3$ is N, CH, C(CH$_3$), or C(halogen); and $Z^1$, $Z^2$, $Z^3$ are not N at the same time;

$Z^4$ is O, CR$^1$, S, N, or NR$^1$;

$Z^5$ is O, CR$^1$, S, N, or NR$^1$;

A, $L^1$, X, Y, R, $R^4$, $R^1$ and $R^2$ at each occurrence are the same as defined in the formula I mentioned above.

Preferably, the compound of formula I is a compound represented by formula Ic, Id, Ie, or If:

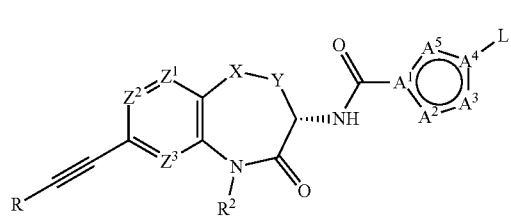

Ic

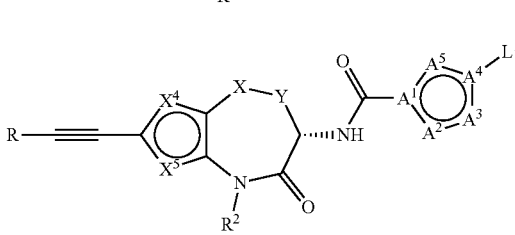

Id

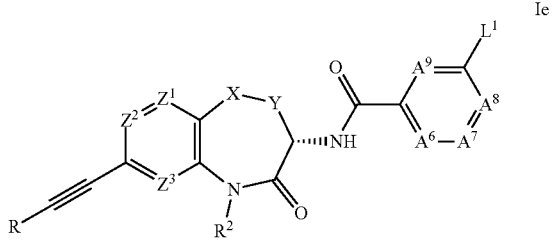

Ie

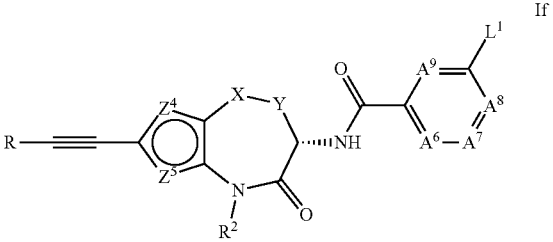

If $Z^1$ is N, CH, C(CH$_3$), or C(halogen);

$Z^2$ is N or CR$^1$;

$Z^3$ is N, CH, C(CH$_3$), or C(halogen); and $Z^1$, $Z^2$, $Z^3$ are not N at the same time;

$Z^4$ is O, CR$^1$, S, N, or NR$^1$;

$Z^5$ is O, CR$^1$, S, N, or NR$^1$;

$A^1$ is C;

$A^4$ is C or N; and $A^2$, $A^3$ and $A^5$ are each independently selected the group consisting of CR$^4$, O, S, N and NR$^4$, so as to form a ring moiety of furyl, thienyl, isoxazolyl, oxazolyl, thiazolyl, oxadiazolyl, pyrrolyl, pyrazolyl, imidazolyl, triazolyl, or tetrazolyl, wherein at most one R$^4$ is not hydrogen;

$A^6$, $A^7$, $A^8$ and $A^9$ are each independently CR$^4$, wherein at most one R$^4$ is not hydrogen; or one of $A^6$, $A^7$, $A^8$ and $A^9$ is N, and the others of $A^6$, $A^7$, $A^8$ and $A^9$ are CH; or one of $A^6$, $A^7$, $A^8$ and $A^9$ is N$^+$—O$^-$, and the others of $A^6$, $A^7$, $A^8$ and $A^9$ are CH;

$L^1$, X, Y, R, $R^4$, $R^1$ and $R^2$ at each occurrence are the same as defined in the formula I mentioned above.

The N$^+$—O$^-$ in the $A^6$ to $A^9$ refers to binding of a positive oium ion formed by N and the ring atoms, with an O$^-$ ion.

Preferably, the compound of the formula I is a compound represented by formula Ig or Ih:

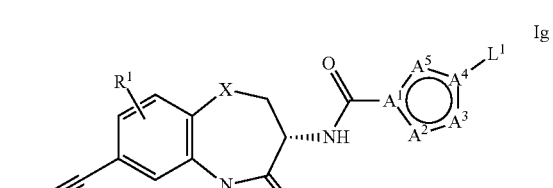

Ig

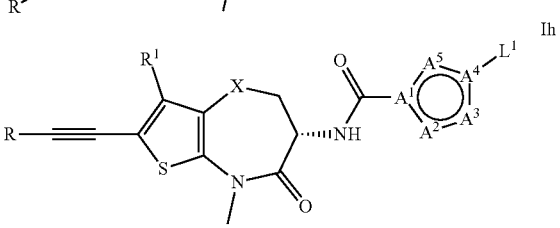

Ih

R¹ is H, halogen, —OH, —CN, $C_1$-$C_6$ alkyl, $C_1$-$C_6$ haloalkyl, $C_1$-$C_6$ alkoxy, or $C_1$-$C_6$ haloalkoxy;

X is O, S, $CH_2$, NH or N(CH);

A¹ is C;

A⁴ is C or N; and

A², A³ and A⁵ are each independently selected from the group consisting of CR⁴, O, S, N and NR⁴, so as to form a ring moiety of furyl, thienyl, isoxazolyl, oxazolyl, thiazolyl, oxadiazolyl, pyrrolyl, pyrazolyl, imidazolyl, triazolyl, or tetrazolyl, wherein at most one R⁴ is not hydrogen;

L¹, R, and R⁴ at each occurrence are the same as defined in the formula I mentioned above;

Preferably, the compound of the formula I is a compound represented by the formula Ii or Ij:

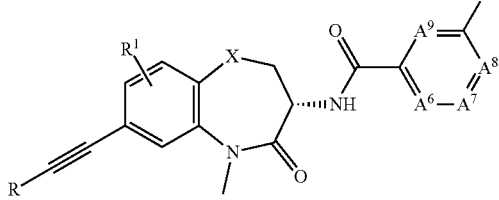

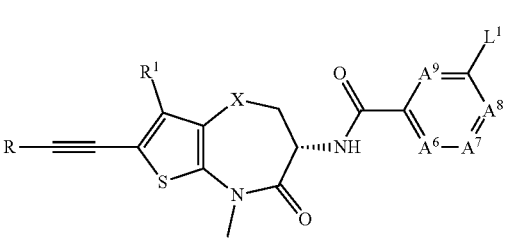

R¹ is H, halogen, —OH, —CN, $C_1$-$C_6$ alkyl, $C_1$-$C_6$ haloalkyl, $C_1$-$C_6$ alkoxy, or $C_1$-$C_6$ haloalkoxy;

X is O, S, $CH_2$, NH or N($CH_3$);

A⁶, A⁷, A⁸ and A⁹ are each independently CR⁴, wherein at most one R⁴ is not hydrogen; or one of A⁶, A⁷, A⁸ and A⁹ is N, and the others of A⁶, A⁷, A⁸ and A⁹ are CH; or one of A⁶, A⁷, A⁸ and A⁹ is N⁺—O⁻, and the others of A⁶, A⁷, A⁸ and A⁹ are CH;

L¹, R, and R⁴ at each occurrence are the same as defined in the formula I mentioned above.

The N⁺—O⁻ in the A⁶ to A⁹ refers to binding of a positive oium ion formed by N and ring atoms, with an O⁻ ion.

Preferably, the compound of the formula I is a compound represented by the formula Ik or Il:

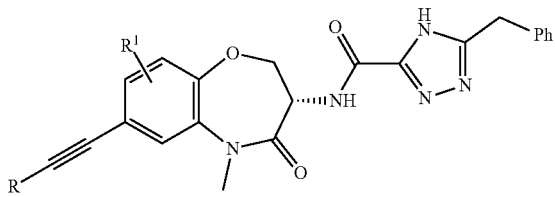

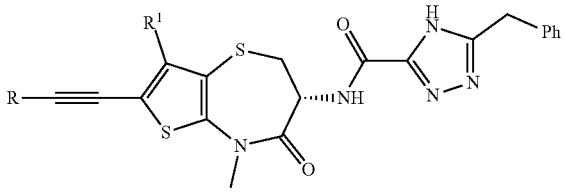

R¹ is H, F, Cl, $CH_3$, or $CH_2CH_3$;

R is isoxazolyl, oxazolyl, thiazolyl, oxadiazolyl, pyrrolyl, pyrazolyl, imidazolyl, triazolyl, pyridinyl, pyrimidinyl, $C_3$-$C_6$ cycloalkyl,

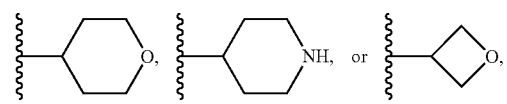

each independently being unsubstituted or substituted with one substituent selected from the group consisting of F, Cl, methyl, ethyl, isopropyl and cyclopropyl.

Preferably, the compound of the formula I is a compound represented by formula Im or In:

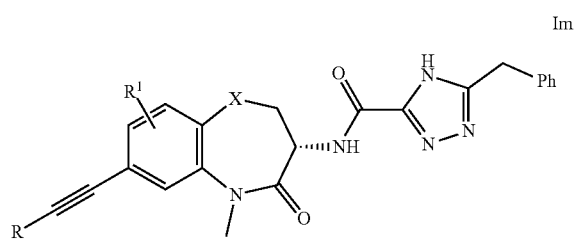

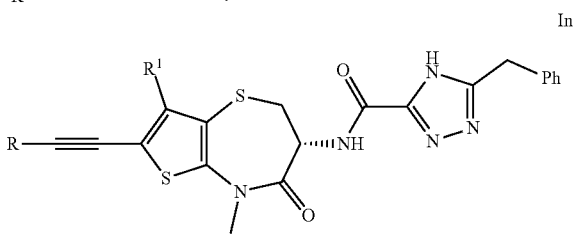

R¹ is H, F, Cl, $CH_3$, or $CH_2CH_3$;

X is O, S or $CH_2$;

R is $C_1$-$C_6$ alkyl, $C_6$-$C_{10}$ aryl, 5-10 membered heteroaryl, 3-7 membered non-aromatic heterocyclyl, $C_3$-$C_8$ cycloalkyl, or $C_5$-$C_8$ cycloalkenyl, wherein the $C_1$-$C_6$ alkyl, the $C_6$-$C_{10}$ aryl, the 5-10 membered heteroaryl, the 3-7 membered non-aromatic heterocyclyl, the $C_3$-$C_8$ cycloalkyl, or the $C_5$-$C_8$ cycloalkenyl are each independently unsubstituted or substituted with 1 to 4 $M^d$s;

$M^d$ is selected from the group consisting of F, Cl, methyl, ethyl, propyl, butyl, trifluoromethyl, —($C_1$-$C_6$ alkylene)-OH, isopropyl, cyclopropyl, hydroxyl, methoxy, amino, methylamino, dimethylamino, diethylamino, $C_6$-$C_{10}$ aryl, 5-10 membered heteroaryl, 3-6 membered non-aromatic heterocyclyl; wherein the $C_6$-$C_{10}$ aryl, the 5-10 membered heteroaryl, and the 3-6 membered non-aromatic heterocyclyl are each independently unsubstituted or substituted by one or two substituents each independently selected from the group consisting of halogen, $C_1$-$C_4$ alkyl, $C_1$-$C_4$ alkoxy, and —CN, or two $M^d$s together with the ring atoms to which they are connected form a 3-8 membered saturated or unsaturated ring.

Preferably, the compound of formula I is selected from the group consisting of the following compounds:

ZB-R-44
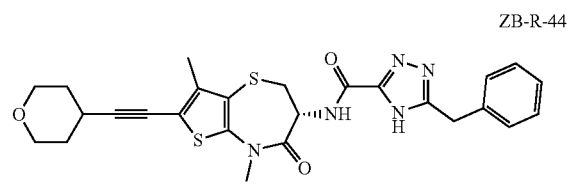

ZB-R-45
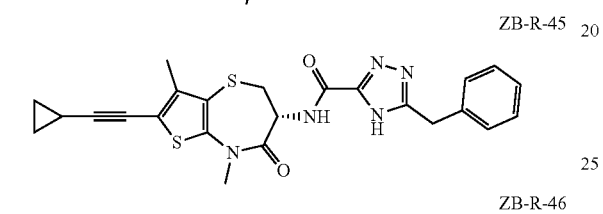

ZB-R-46
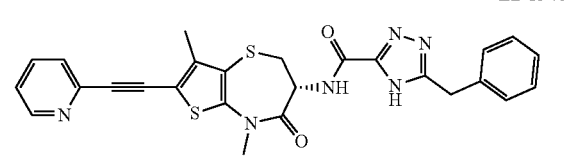

ZB-R-47
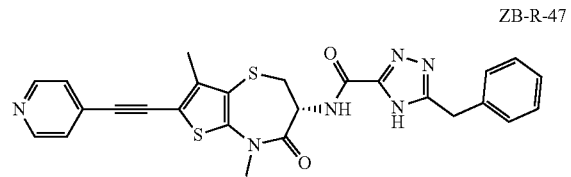

ZB-R-42
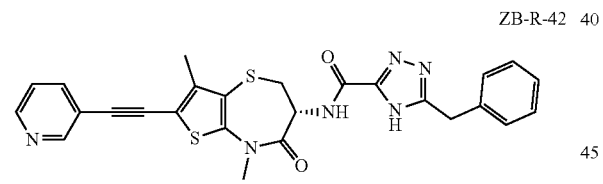

ZB-R-48
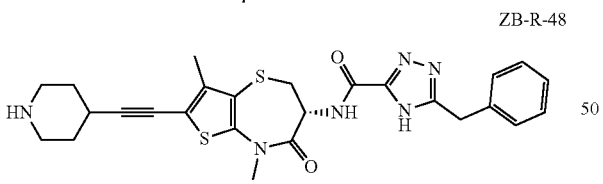

ZB-R-39
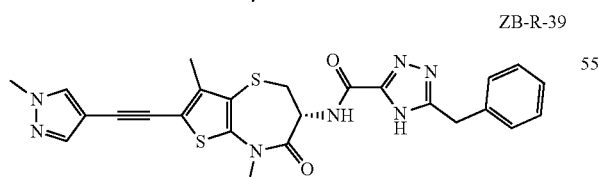

ZB-R-1
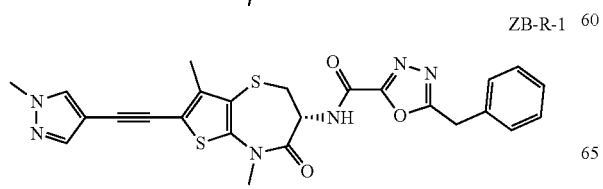

-continued

ZB-R-2
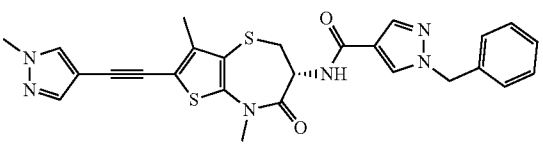

ZB-R-3
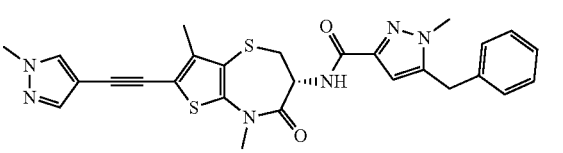

ZB-R-4
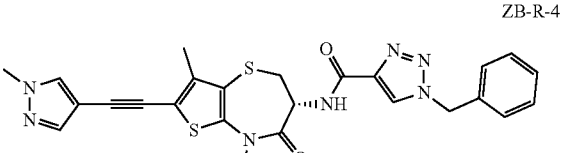

ZB-R-5
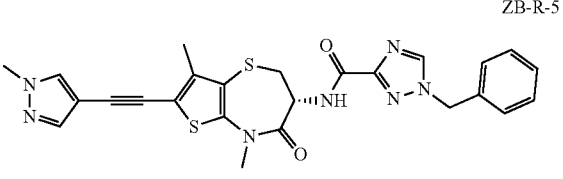

ZB-R-6
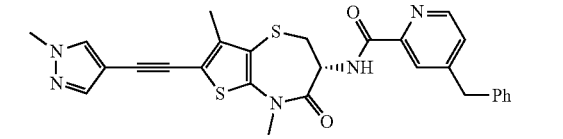

ZB-R-50
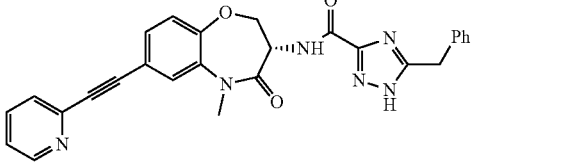

ZB-R-51
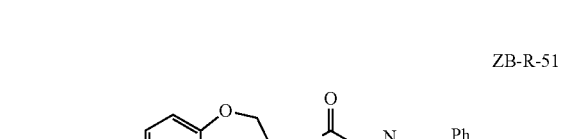

ZB-R-52

ZB-R-53
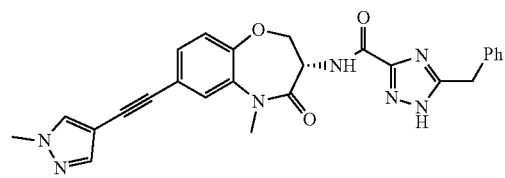
ZB-R-54
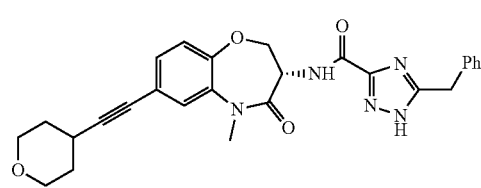
ZB-R-55
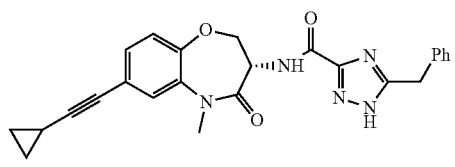
ZB-R-56
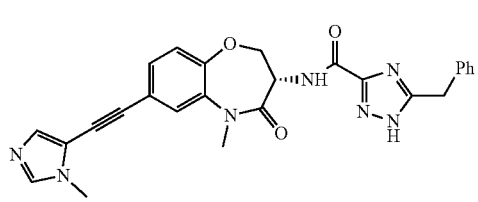
ZB-R-57
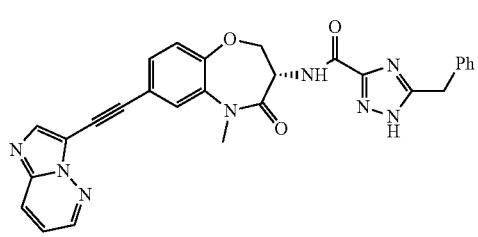
ZB-R-58
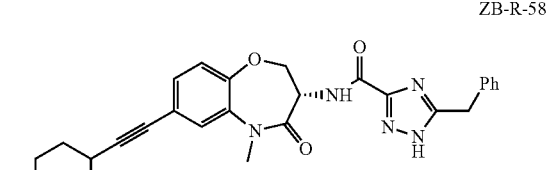
ZB-R-7
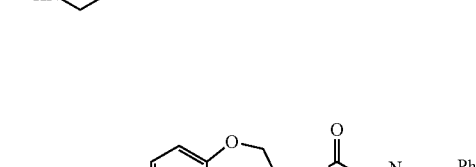
ZB-R-8
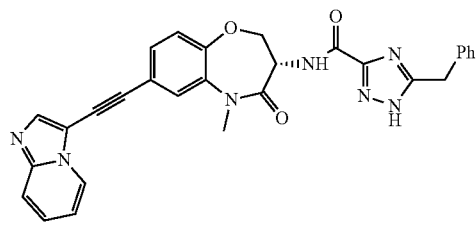
ZB-R-9
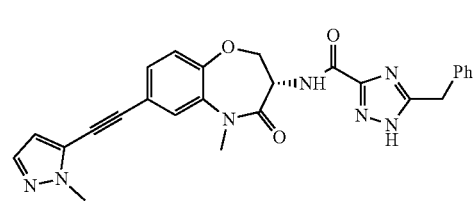
ZB-R-10
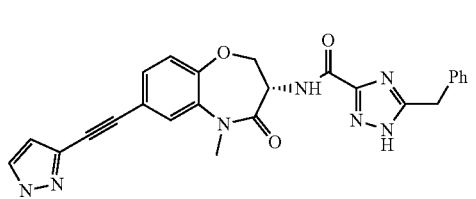
ZB-R-67
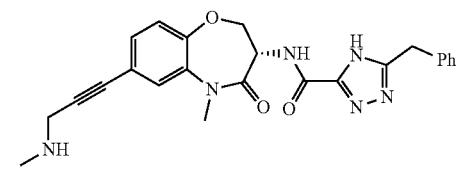
ZB-R-68
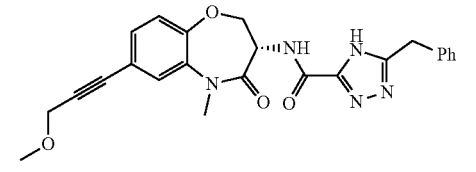
ZB-R-76
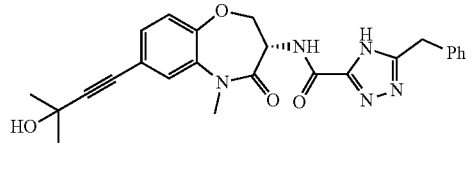
ZB-R-77
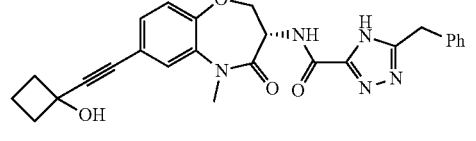
ZB-R-78
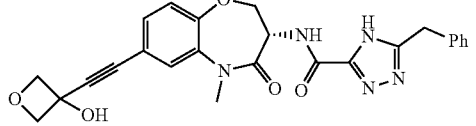

ZB-R-79
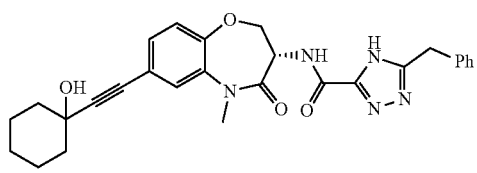
ZB-R-80
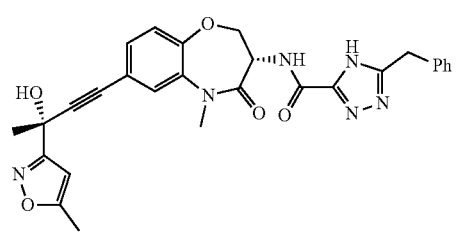
ZB-R-81
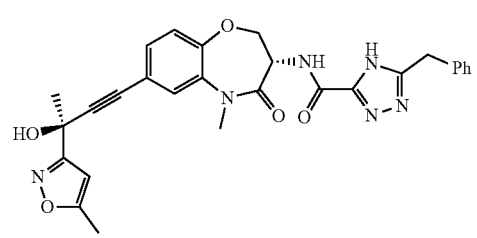
ZB-R-82
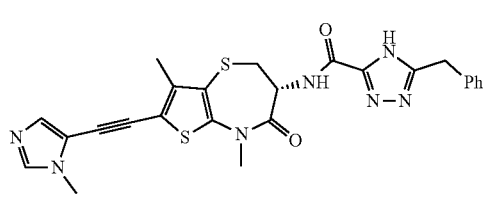
ZB-R-83
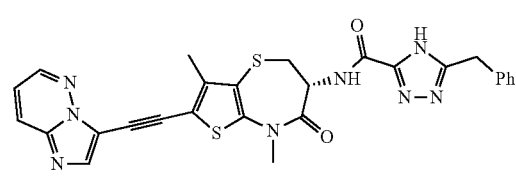
ZB-R-84
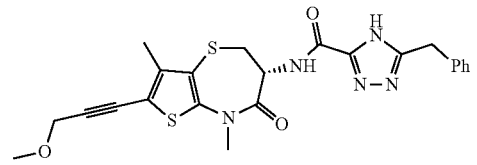
ZB-R-85
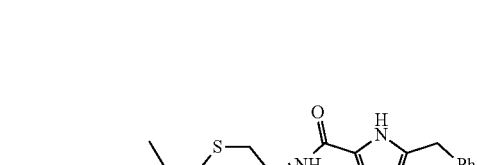
ZB-R-86
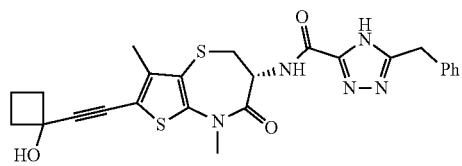
ZB-R-87
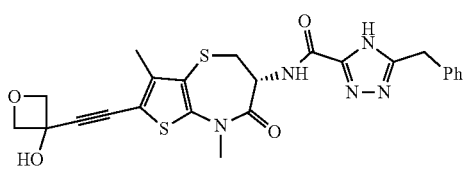
ZB-R-88
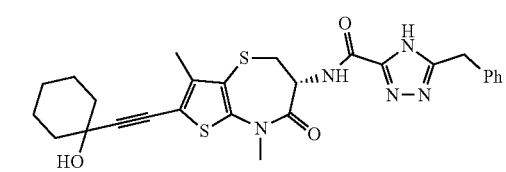
ZB-R-89
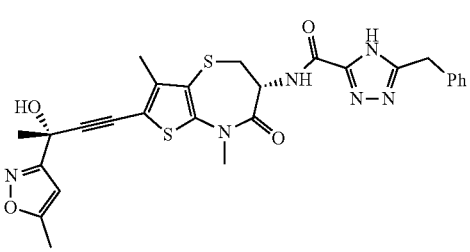
ZB-R-90
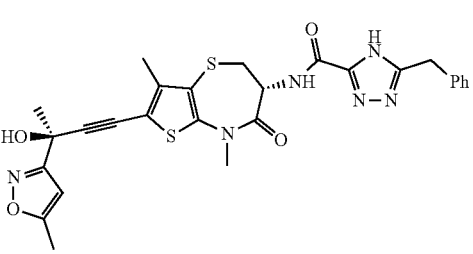
ZB-R-20
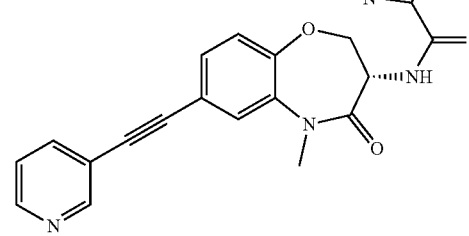

ZB-R-21
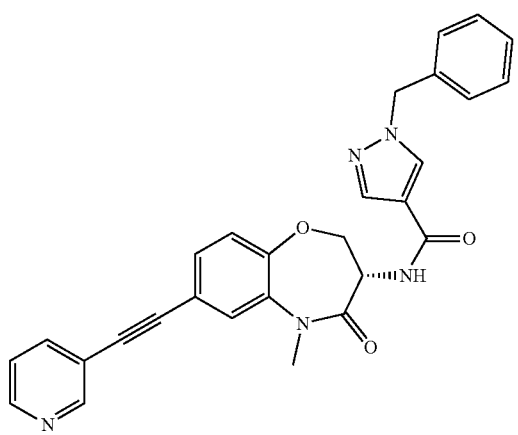
ZB-R-22
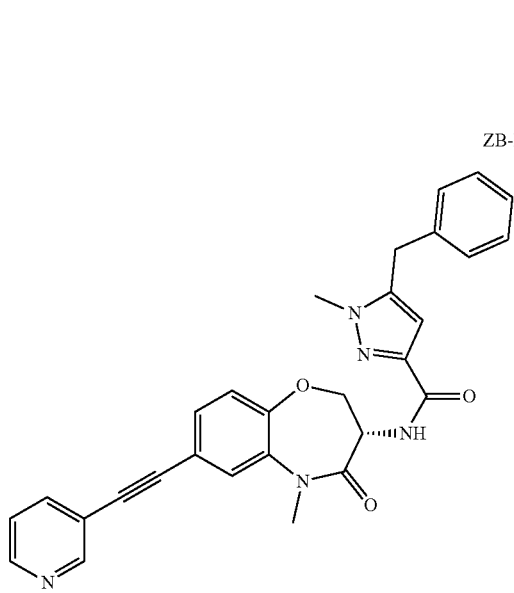
ZB-R-23
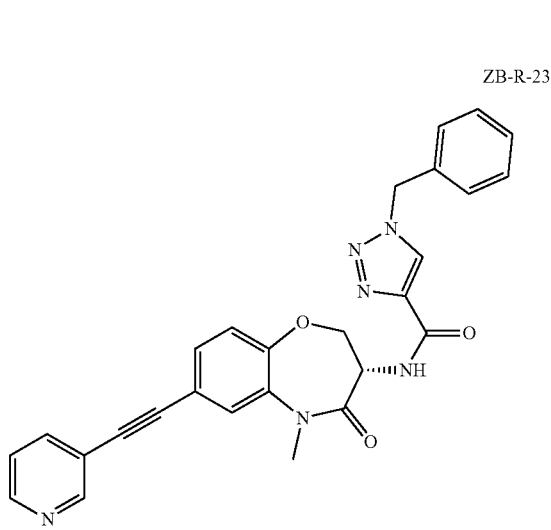
ZB-R-24
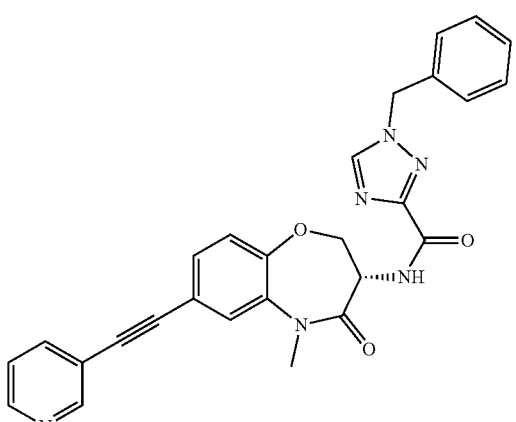
ZB-R-25
ZB-R-26
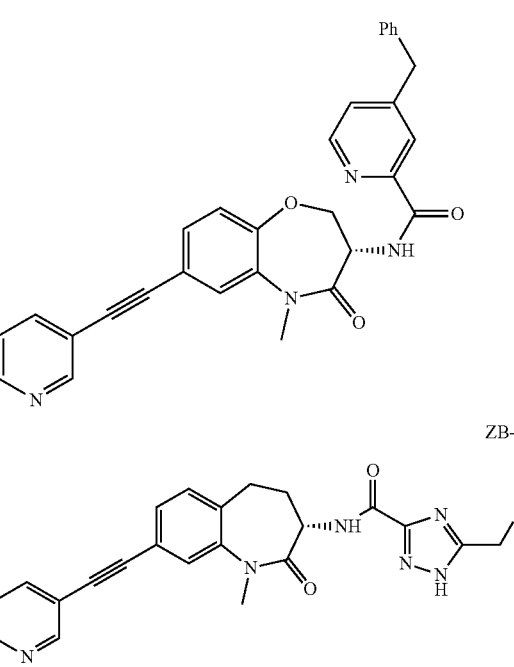
ZB-R-27
ZB-R-28
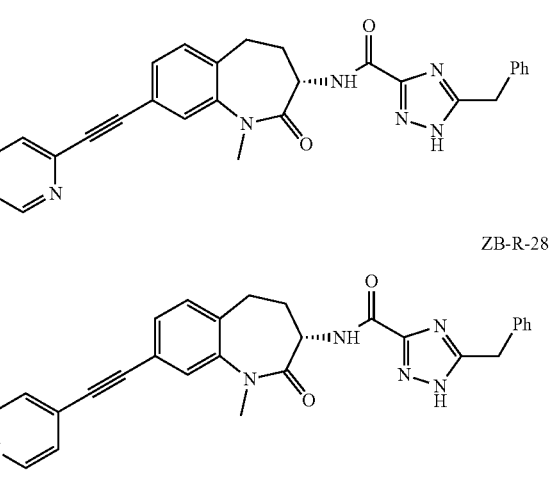

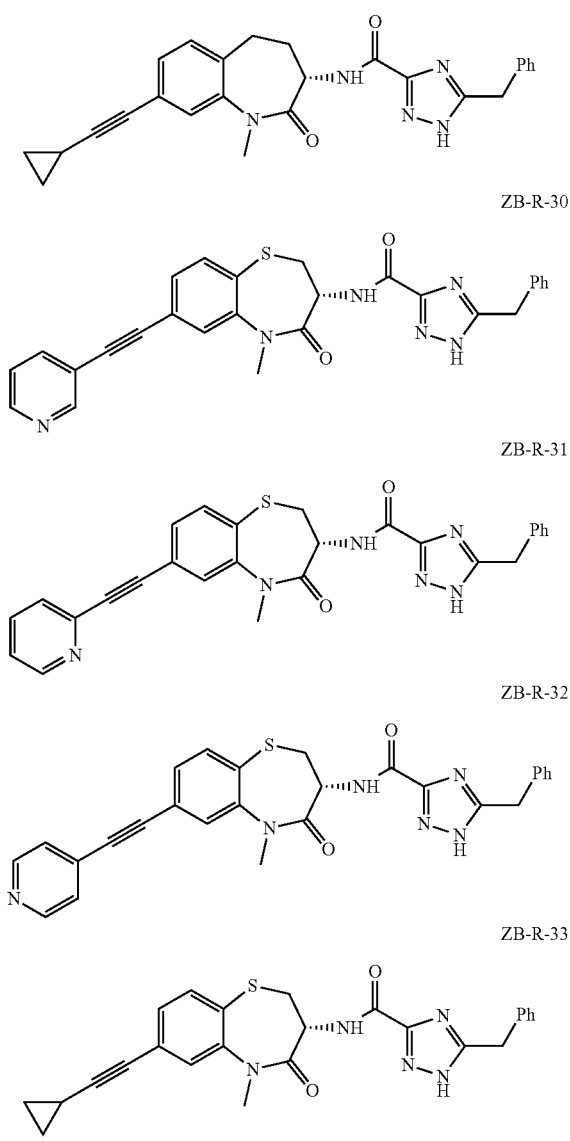

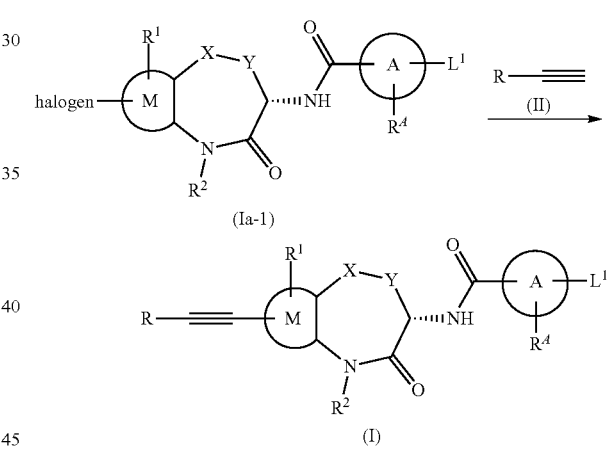

be at least partially regulated by programmed necrosis, especially inflammatory bowel disease (including Crohn's disease, ulcerative colitis), psoriasis, retinal detachment, retinitis pigmentosa, macular degeneration, pancreatitis, atopic dermatitis, rheumatoid arthritis, spondyloarthritis, gout, SoJIA, systemic lupus erythematosus, Sjogren's syndrome, systemic scleroderma, antiphospholipid syndrome, vasculitis, osteoarthritis, non-alcoholic fatty liver hepatitis, autoimmune hepatitis, autoimmune hepatobiliary disease, primary sclerosed cholangitis, nephritis, celiac disease, autoimmune ITP, transplant rejection, solid organ ischemia-reperfusion injury, sepsis, systemic inflammatory response syndrome, cerebrovascular accident, myocardial infarction, Huntington's disease, Alzheimer's disease, Parkinson's disease, allergic disease, asthma, multiple sclerosis, Type I diabetes, Wegener's granulomatosis, pulmonary sarcoidosis, Behcet's disease, interleukin-I converting enzyme-related fever syndrome, chronic obstructive pulmonary disease, tumor necrosis factor receptor-related periodic syndrome, and periodontitis.

According to another aspect of the invention, provided is a method for preparing the compound of the present invention, wherein the method is one selected from the following schemes.

An aryl halide (Formula Ia-1, wherein halogen is Cl, Br, or I) is treated with a R-containing alkynyl compound (formula II) under a Sonogashira coupling condition to produce a compound of Formula I. Generally, the coupling reaction is carried out in the presence of a metal catalyst, which includes but not limited to a palladium metal catalyst, a copper metal catalyst or a combination thereof, and a base, in a suitable solvent at an elevated temperature, for example, about 80° C. to 150° C. The reaction can be promoted by microwave radiation. The palladium metallic catalyst includes, but not limited to, bis(triphenylphosphine)palladium (11) dichloride, allylpalladium (II) chloride dimer, [1,1'-bis(diphenylphosphino)ferrocene]palladium dichloride ((dppf)PdCl$_2$), palladium (II) acetate. The copper metallic catalyst includes, but not limited to, cuprous iodide. Examples of suitable bases that can be used include, but not limited to, triethylamine, pyridine, diisopropylethylamine, 1,8-diazabicyclo[5.4.0]undec-7-ene (DBU). Non-limiting examples of the suitable solvent include N,N-dimethylformamide, dimethylacetamide, methanol, ethanol, acetoni- Preferably, the isotope-labeled compound is, for example, a deuterium substituted compound. The isotope-labeled compounds can be used in applications such as metabolism detection.

In another aspect, the present invention provides a pharmaceutical composition comprising a therapeutically effective amount of one or more selected from the group consisting of the compound of formula (I), and pharmaceutically acceptable salts, enantiomers, diastereomers, atropisomers, optical isomers, racemates, polymorphs, solvates and isotopically labeled compounds thereof, and optionally, a pharmaceutically acceptable carrier.

In another aspect, the compounds in the present invention are particularly effective for the treatment of a disease or disorder mediated by RIP1 kinase. Such RIP1 mediated disease or disorder is a disease or disorder mediated by activation of RIP1 kinase, and therefore, the inhibition of RIP1 kinase is beneficial to the treatment of the disease or disorder. In particular, the compound of the present invention can be used in treatment of a disease/disorder that may trile, dimethoxyethane, dimethylsulfoxide, dioxane, tetrahydrofuran, ethylene glycol dimethyl ether, toluene.

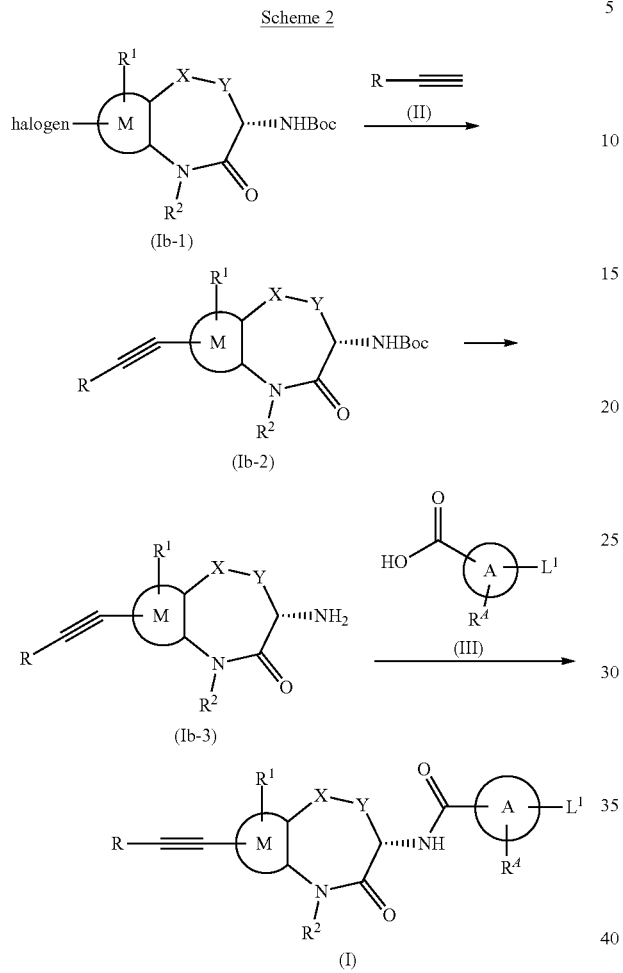

An aryl halide (Formula Ib-1, wherein halogen is Cl, Br, or I) is treated with a R-containing alkynyl compound (formula II) under a Sonogashira coupling condition to obtain an intermediate (formula Ib-2) by coupling, and then boc is deprotected under an acidic condition to obtain a free amine (formula Ib-3). Subsequently, the generated free amine (formula Ib-3) is condensed with a suitable acid (formula III) in the presence of an amide condensation reagent to obtain the target product (formula I).

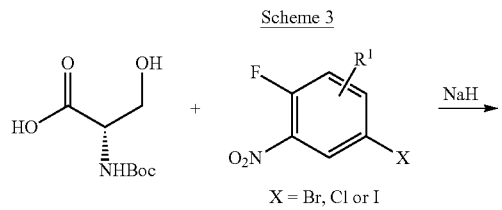

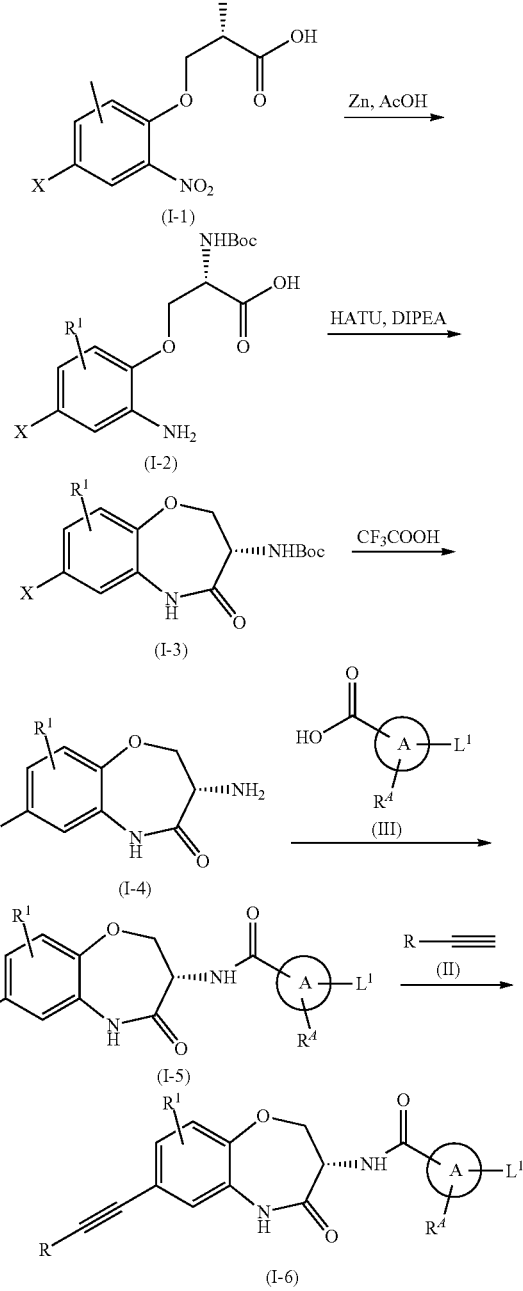

Boc-L-serine is reacted with an appropriately substituted 1-fluoro-2-nitrobenzene in the presence of a base to obtain I-1, and then the nitro is reduced to obtain the amine 1-2 (the reduction condition includes but not limited to Zn/AcOH, Fe/NH$_4$Cl/EtOH, Zn/NH$_4$Cl/EtOH), and an intramolecular condensation is conducted in the presence of a condensation reagent to obtain an intermediate (formula I-3) (the condensation reagent is, for example, but not limited to HATU, HBTU, EDC.HCl, BOP), and then Boc is deprotected under an acidic condition (such as but not limited to CF$_3$COOH, HCl) to obtain the free amine I-4. Further, the generated free amine is condensed with a suitable acid (formula III) in the presence of an amide condensation reagent (such as but not limited to HATU, HBTU, EDC.HCl, BOP) to obtain an intermediate (formula I-5). Finally, the I-5 is treated with a R-containing alkynyl compound (formula II) under a Sonogashira coupling condition to obtain the final product I-6.

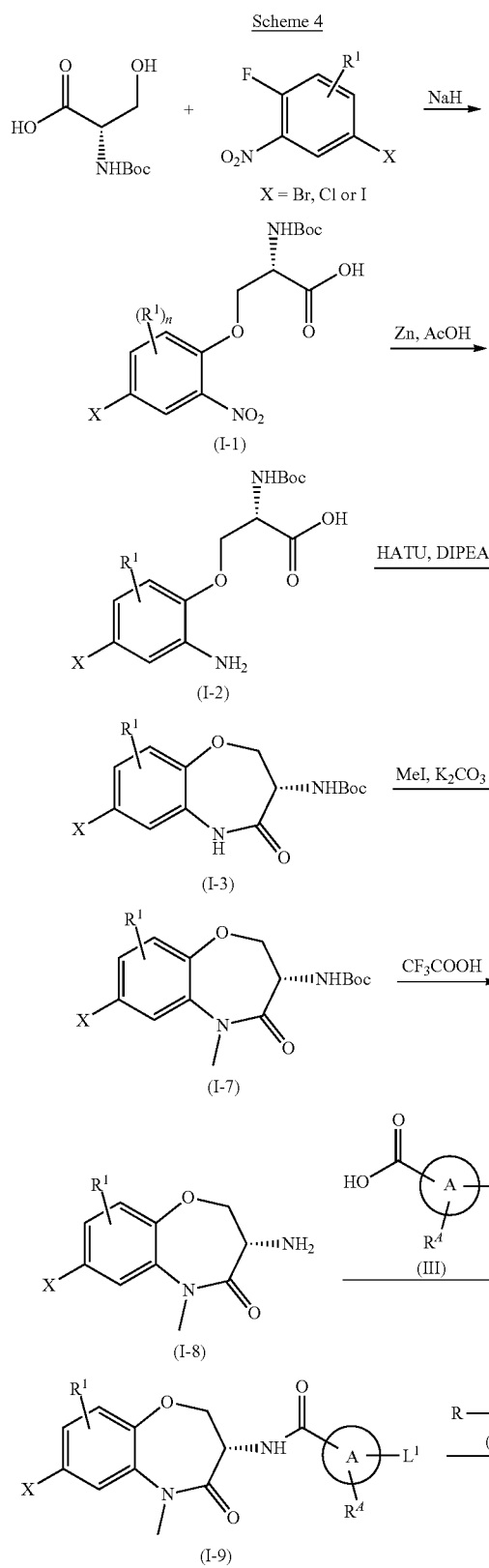

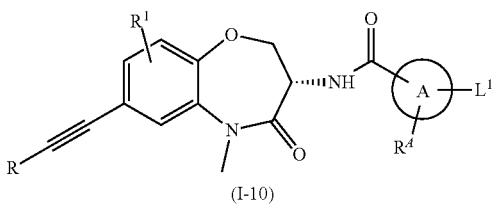

Alternatively, a compound of formula I-3 is produced according to the same steps in 3, methylated to give I-7, and then boc-deprotected under an acidic condition (e.g., but not limited to CF$_3$COOH, HCl) to give the free amine I-8. Then the generated free amine I-8 is condensed E with a suitable acid (formula III) in the presence of an amide condensation reagent (such as but not limited to HATU, HBTU, EDC.HCl, BOP) to obtain an intermediate (formula I-9). Finally, I-9 is treated with a R-containing alkynyl compound (formula II) under a Sonogashira coupling condition to obtain the final product I-10.

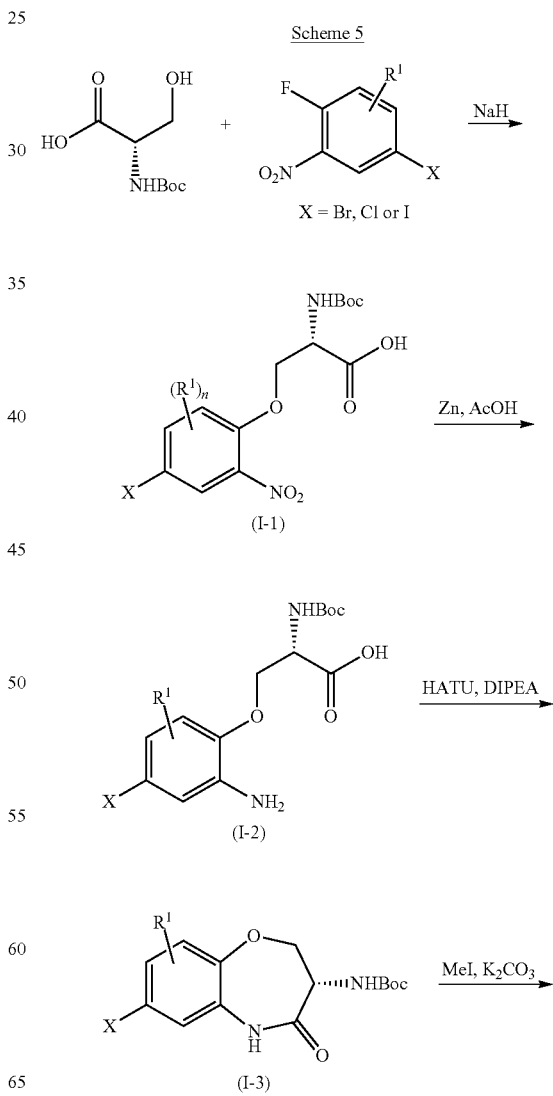

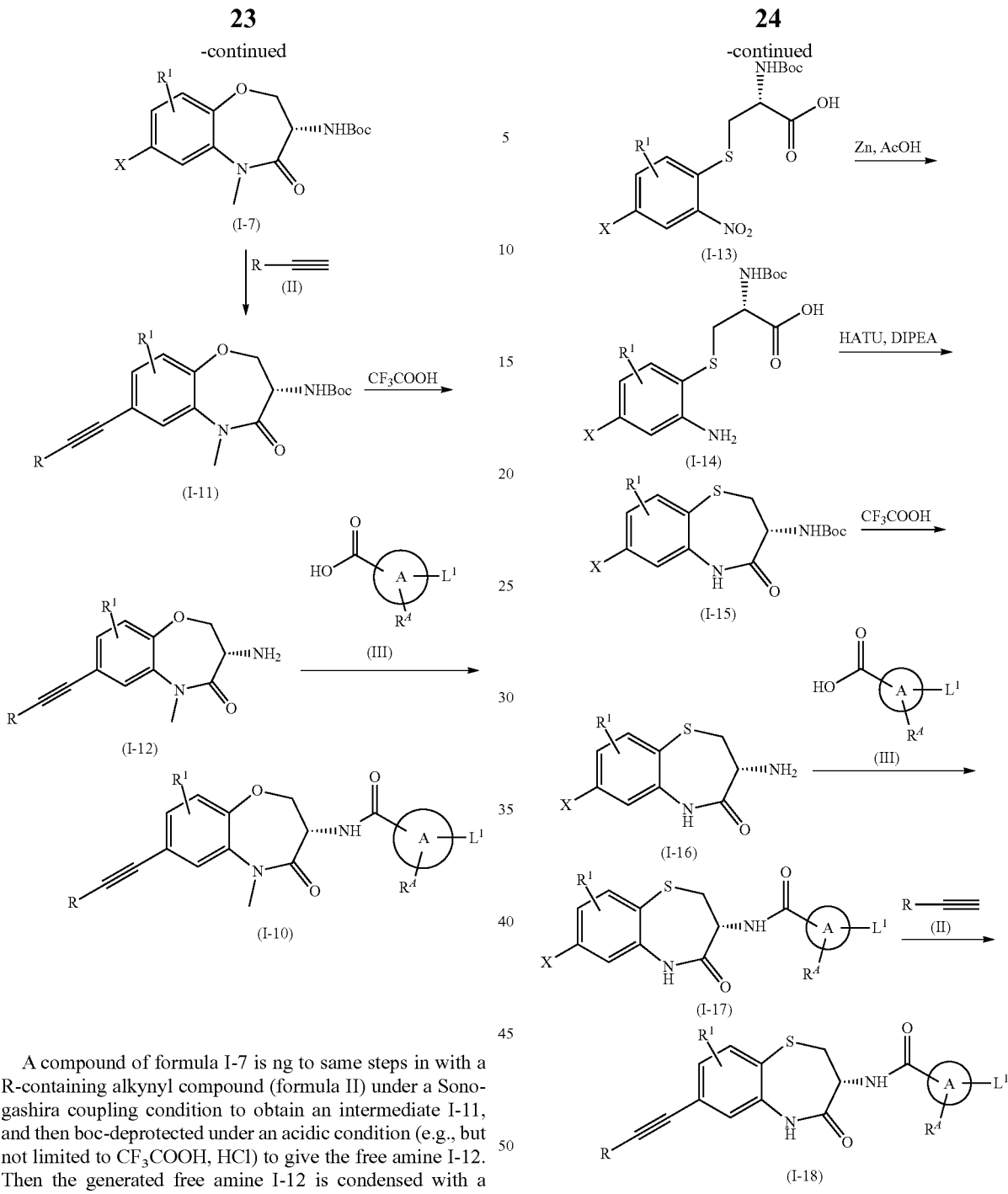

A compound of formula I-7 is ng to same steps in with a R-containing alkynyl compound (formula II) under a Sonogashira coupling condition to obtain an intermediate I-11, and then boc-deprotected under an acidic condition (e.g., but not limited to $CF_3COOH$, HCl) to give the free amine I-12. Then the generated free amine I-12 is condensed with a suitable acid (formula 111) in the presence of an amide condensation reagent (such as but not limited to HATU, HBTU, EDC.HCl, BOP) to obtain the final product (formula I-10).

Scheme 6

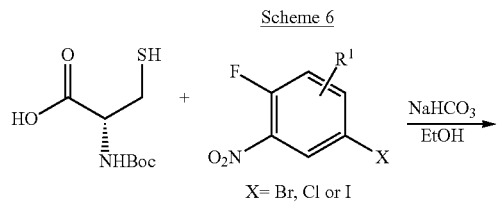

X= Br, Cl or I

Boc-L-cysteine is reacted with an appropriately substituted 1-fluoro-2-nitrobenzene in the presence of a base to obtain I-13, and then the nitro is reduced to obtain the amine I-14 (the reduction condition includes such as but not limited to Zn/AcOH, Fe/$NH_4$Cl/EtOH, Zn/$NH_4$Cl/EtOH), and an intramolecular condensation is conducted in the presence of a condensation reagent to obtain an intermediate of formula I-15 (the condensation reagent is, for example, but not limited to HATU, HBTU, EDC.HCl, or BOP), and then Boc deprotection is performed under an acidic condition (such as but not limited to $CF_3COOH$, HCl) to obtain the free amine I-16. Then the generated free amine I-16 is condensed with a suitable acid (formula III) in the presence of an amide condensation reagent (such as but not limited to HATU, HBTU, EDC.HCl, BOP) to obtain an intermediate (formula I-17). Finally, I-17 is treated with a R-containing alkynyl compound (formula II) under a Sonogashira coupling condition to obtain the final product I-18.

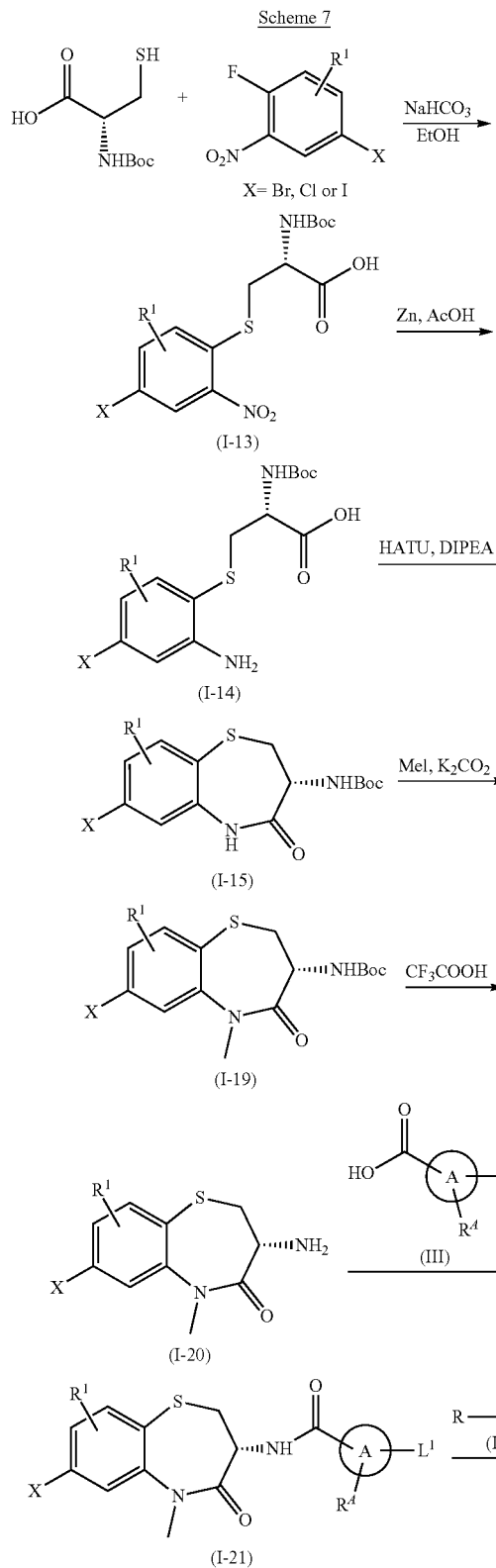

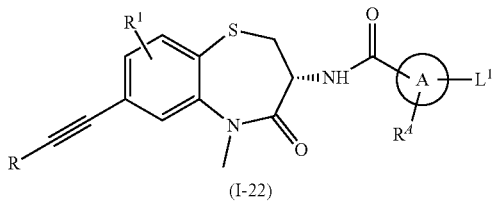

A compound of formula I-15 is produced according to the same steps in methylated to give I-19, and then boc-deprotected under an acidic condition (e.g., but not limited to CF₃COOH, HCl) to give the free amine I-20. Then the generated free amine I-20 is condensed with a suitable acid (formula III) in the presence of an amide condensation reagent (such as but not limited to HATU, HBTU, EDC.HCl, BOP) to obtain an intermediate (formula I-21). Finally, I-21 is treated with a R-containing alkynyl compound (formula II) under a Sonogashira coupling condition to obtain the final product I-22.

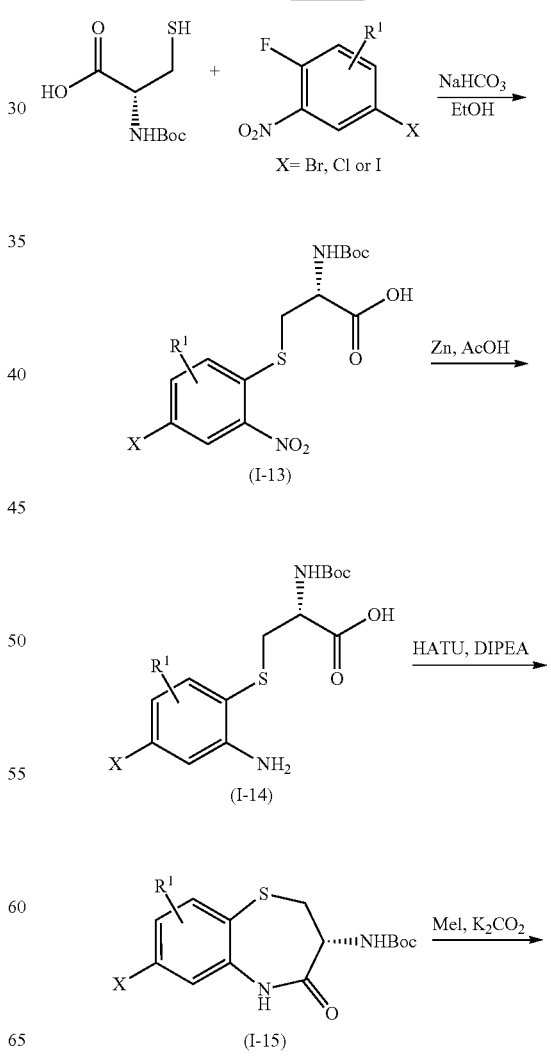

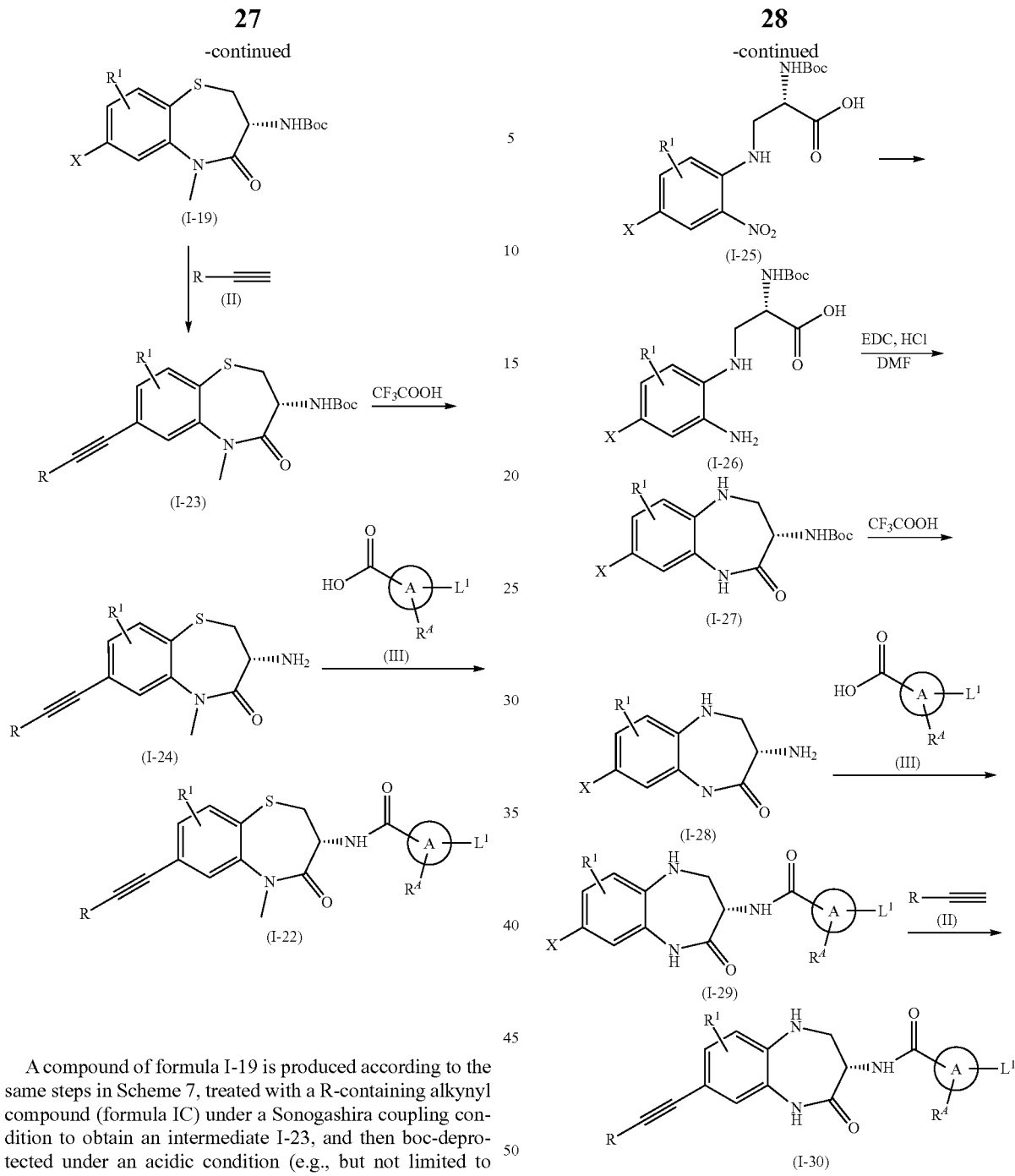

A compound of formula I-19 is produced according to the same steps in Scheme 7, treated with a R-containing alkynyl compound (formula IC) under a Sonogashira coupling condition to obtain an intermediate I-23, and then boc-deprotected under an acidic condition (e.g., but not limited to $CF_3COOH$, HCl) to give the free amine I-24. Then the generated free amine I-24 is condensed with a suitable acid (formula III) in the presence of an amide condensation reagent (such as but not limited to HATU, HBTU, EDC.HCl, BOP) to obtain the final product (formula I-22).

3-amino-alanine is reacted with an appropriately substituted 1-fluoro-2-nitrobenzene in the presence of a base to obtain I-25, and then the nitro is reduced to obtain the amine I-26 (the reduction condition includes such as but not limited to Zn/AcOH, Fe/$NH_4$Cl/EtOH, Zn/$NH_4$Cl/EtOH), and an intramolecular condensation is conducted in the presence of a condensation reagent to obtain an intermediate of formula I-27 (the condensation reagent is, for example, but not limited to HATU, HBTU, EDC.HCl, or BOP), and then Boc deprotection is conducted under an acidic condition (such as but not limited to $CF_3COOH$, HCl) to obtain the free amine I-28. Then the generated free amine I-28 is condensed with a suitable acid (formula III) in the presence of an amide condensation reagent (such as but not limited to HATU, HBTU, EDC.HCl, BOP) to obtain an intermediate (formula Scheme 9

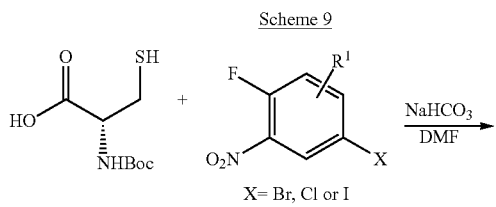

X= Br, Cl or I

I-29). Finally, I-29 is treated with a R-containing alkynyl compound (formula II) under a Sonogashira coupling condition to obtain the final product I-30.

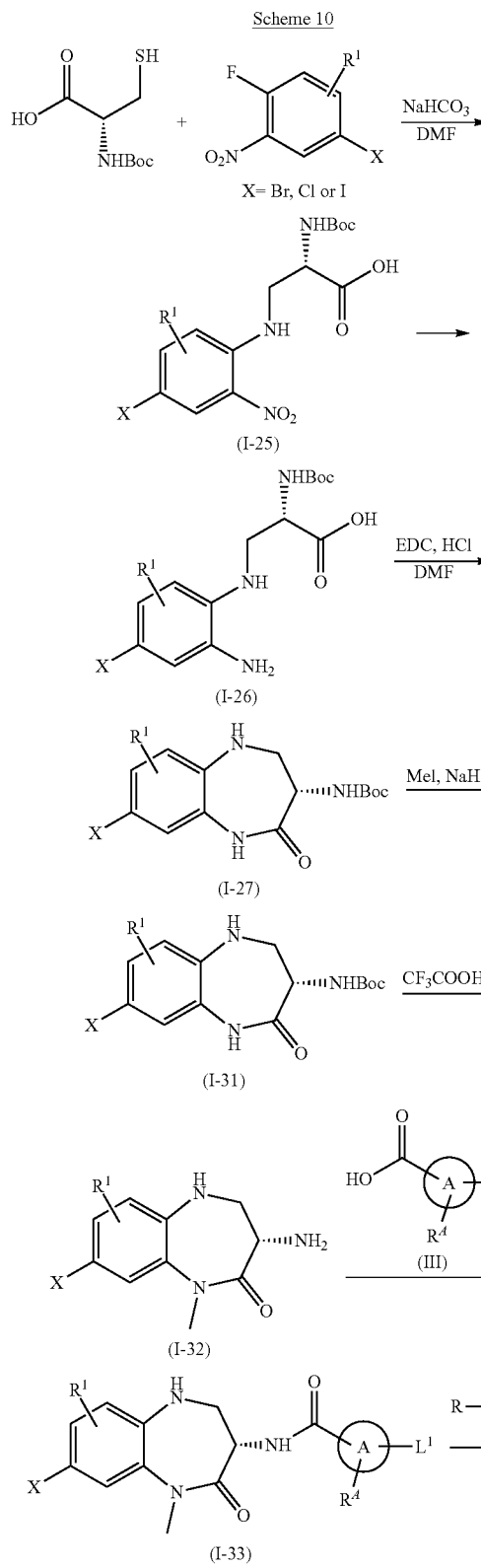

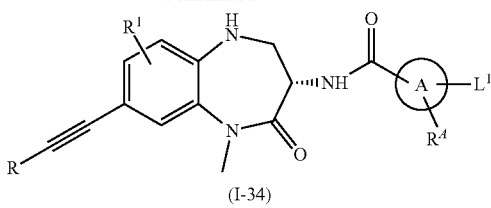

A compound of formula I-27 is produced according to the same steps in Scheme 9, methylated to give I-31, and then Boc-deprotected under an acidic condition (e.g., but not limited to CF$_3$COOH, HCl) to give the free amine I-32. Then the generated free amine I-32 is condensed with a suitable acid (formula III) in the presence of an amide condensation reagent (such as but not limited to HATU, HBTU, EDC.HCl, BOP) to obtain an intermediate (formula I-33). Finally, I-33 is treated with a R-containing alkynyl compound (formula II) under a Sonogashira coupling condition to obtain the final product I-34.

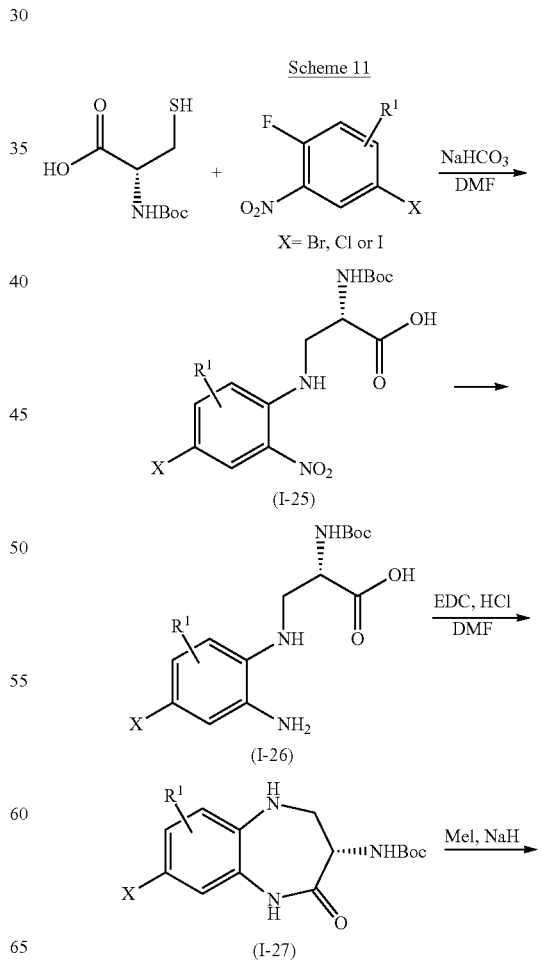

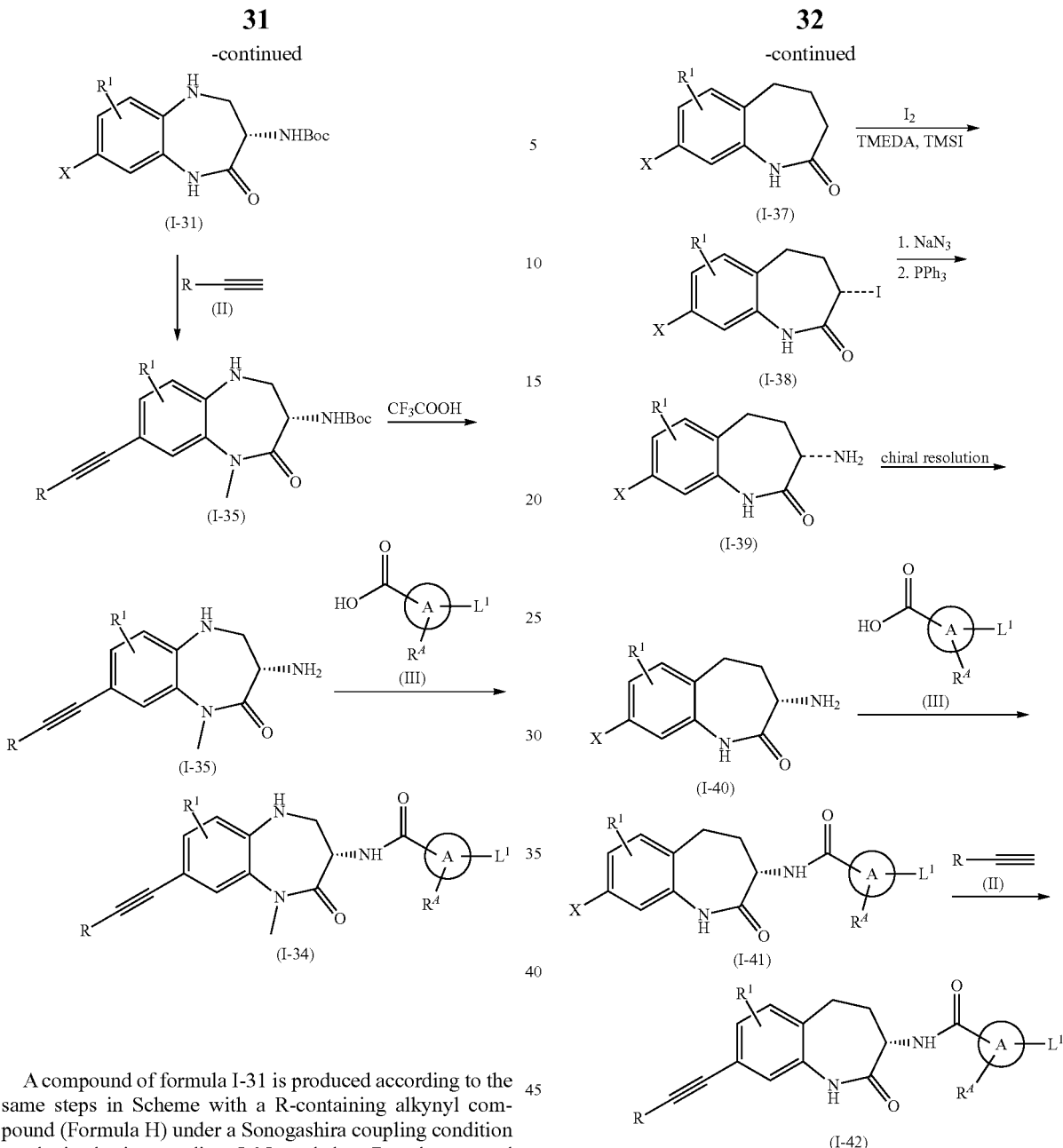

A compound of formula I-31 is produced according to the same steps in Scheme with a R-containing alkynyl compound (Formula II) under a Sonogashira coupling condition to obtain the intermediate I-35, and then Boc-deprotected under an acidic condition (e.g., but not limited to CF₃COOH, HCl) to give the free amine I-36. Then the generated free amine I-36 is condensed with a suitable acid (formula III) in the presence of an amide condensation reagent (such as but not limited to HATU, HBTU, EDC.HCl, BOP) to obtain the final product (formula I-34).

Scheme 12

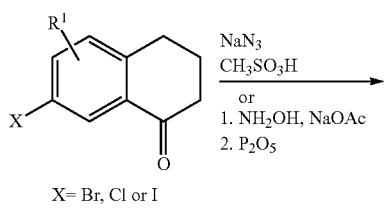

Through an acid-mediated Schmidt reaction with sodium azide or through an Beckmann rearrangement reaction of an ketoxime formed by reaction with NH₂OH, an suitably substituted tetralone can be converted into an suitably substituted 1,3,4,5-tetrahydro-1-benzazepine-2-one (Formula I-37). Then, I-37 is converted into an α-iodobenzolactam (formula I-38) through trimethyl iodosilane-mediated iodination, and then converted into an α-azidobenzolactam with sodium azide, and then subjected to staudinge reduction with triphenylphosphine to generate an α-aminobenzolactam (formula I-39), followed by chiral resolution to obtain the key intermediate (formula I-40), which is then condensed with a suitable acid (formula III) in the presence of an amide condensation reagent to obtain an intermediate (formula I-41). Finally, I-41 is treated with a R-containing alkynyl compound (formula II) under a Sonogashira coupling condition to obtain the final product I-42.

Scheme 13

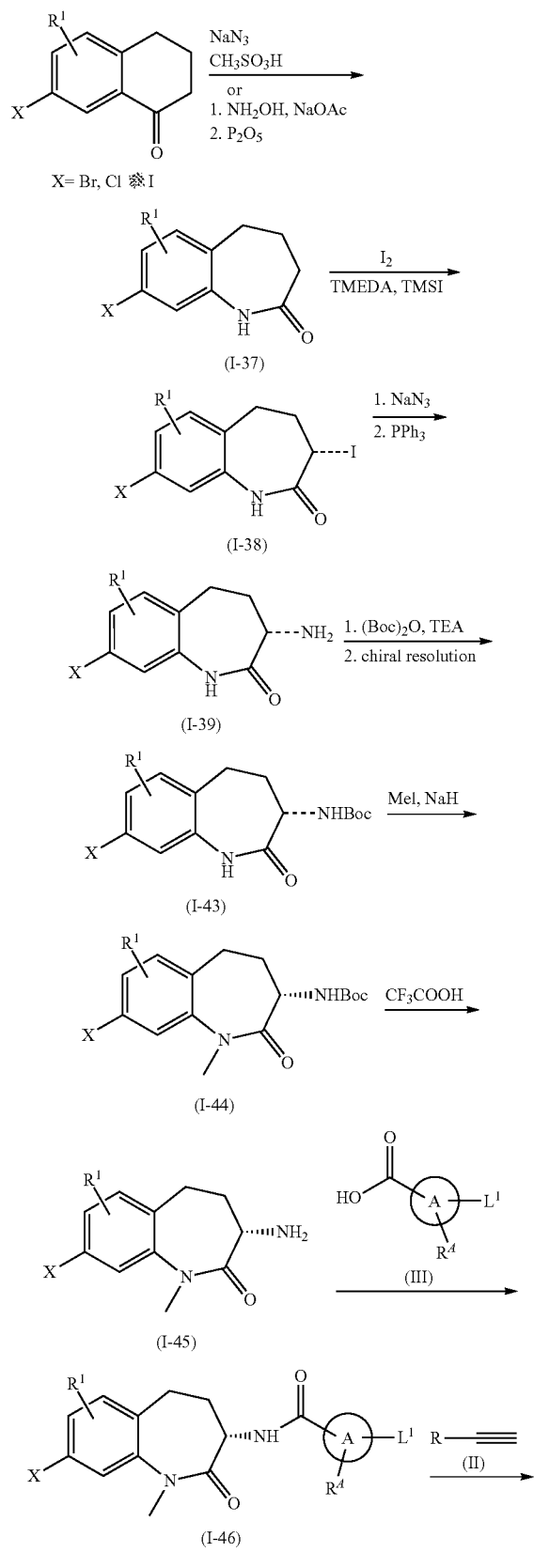

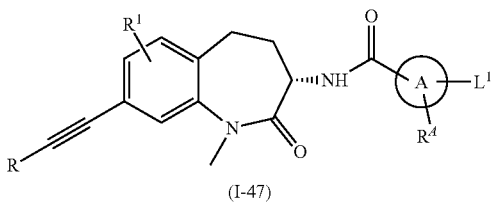

The compound I-39 is produced according to the same steps as in Scheme 12. The intermediate α-aminobenzolactam (formula I-39) is protected by Boc, and then subjected to chiral resolution to obtain an intermediate (formula I-43). The compound of formula I-43 is methylated to give I-44, which is then Boc-deprotected under an acidic condition (e.g., but not limited to CF$_3$COOH, HCl) to give the free amine I-45. Then the generated free amine I-45 is condensed with a suitable acid (formula III) in the presence of an amide condensation reagent (such as but not limited to HATU, HBTU, EDC.HCl, BOP) to obtain an intermediate (formula I-46). Finally, I-46 is treated with a R-containing alkynyl compound (formula II) under a Sonogashira coupling condition to obtain the final product I-47.

Scheme 14

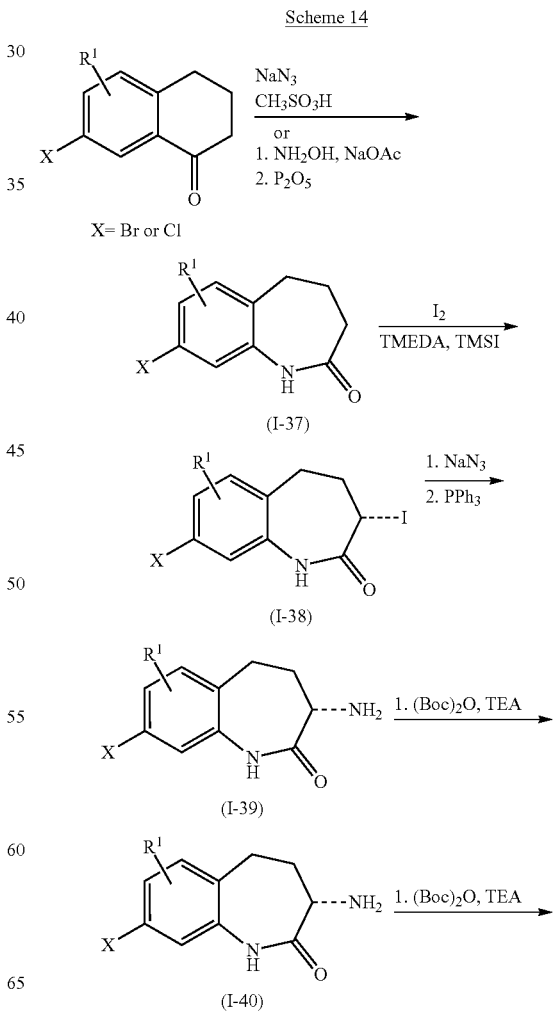

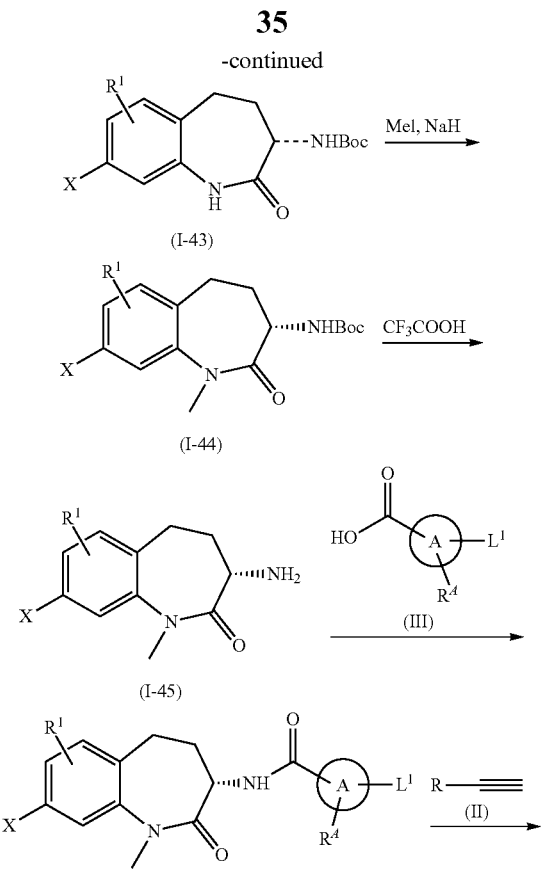

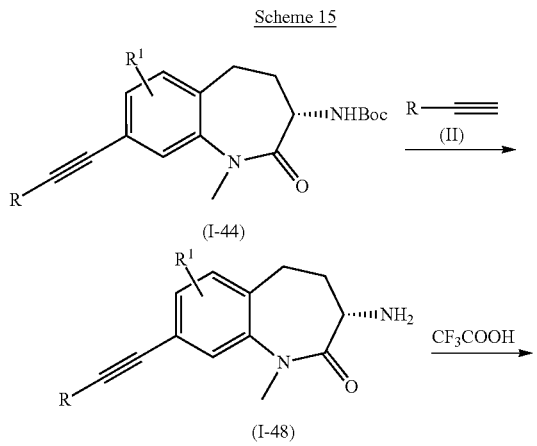

The compound I-40 is produced according to the same steps as in intermediate (formula I-43) is obtained by the reaction of the intermediate (formula I-40) with Boc anhydride. Then the final product I-47 is obtained following the steps in Scheme 13.

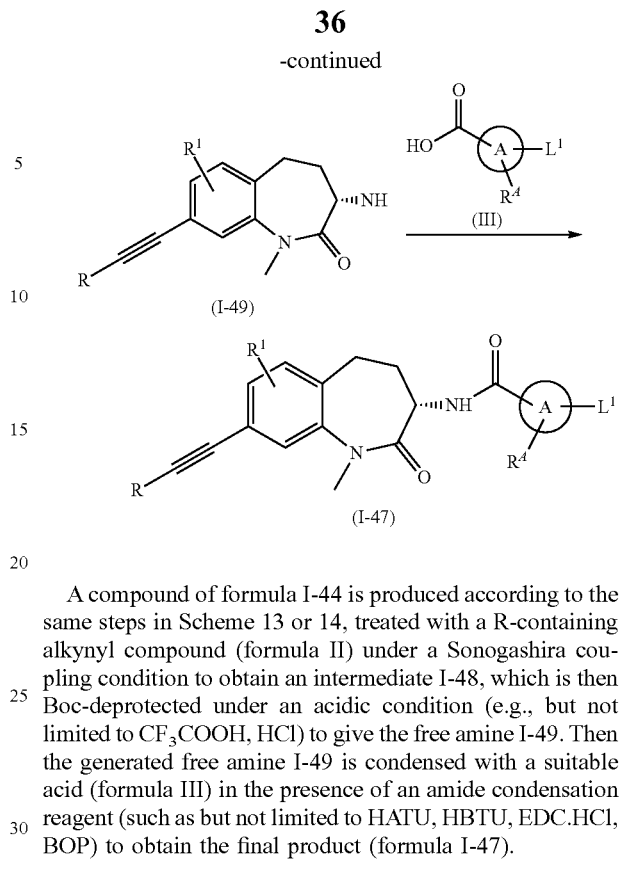

A compound of formula I-44 is produced according to the same steps in Scheme 13 or 14, treated with a R-containing alkynyl compound (formula II) under a Sonogashira coupling condition to obtain an intermediate I-48, which is then Boc-deprotected under an acidic condition (e.g., but not limited to CF₃COOH, HCl) to give the free amine I-49. Then the generated free amine I-49 is condensed with a suitable acid (formula III) in the presence of an amide condensation reagent (such as but not limited to HATU, HBTU, EDC.HCl, BOP) to obtain the final product (formula I-47).

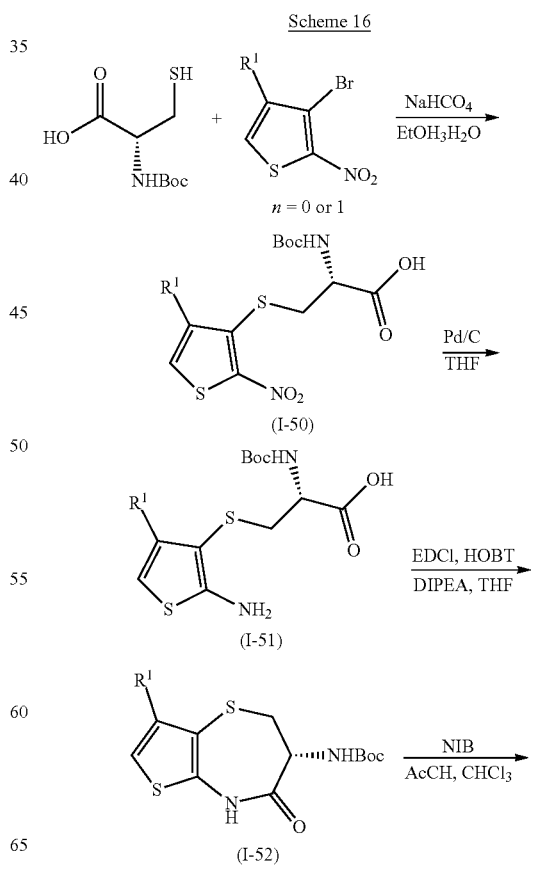

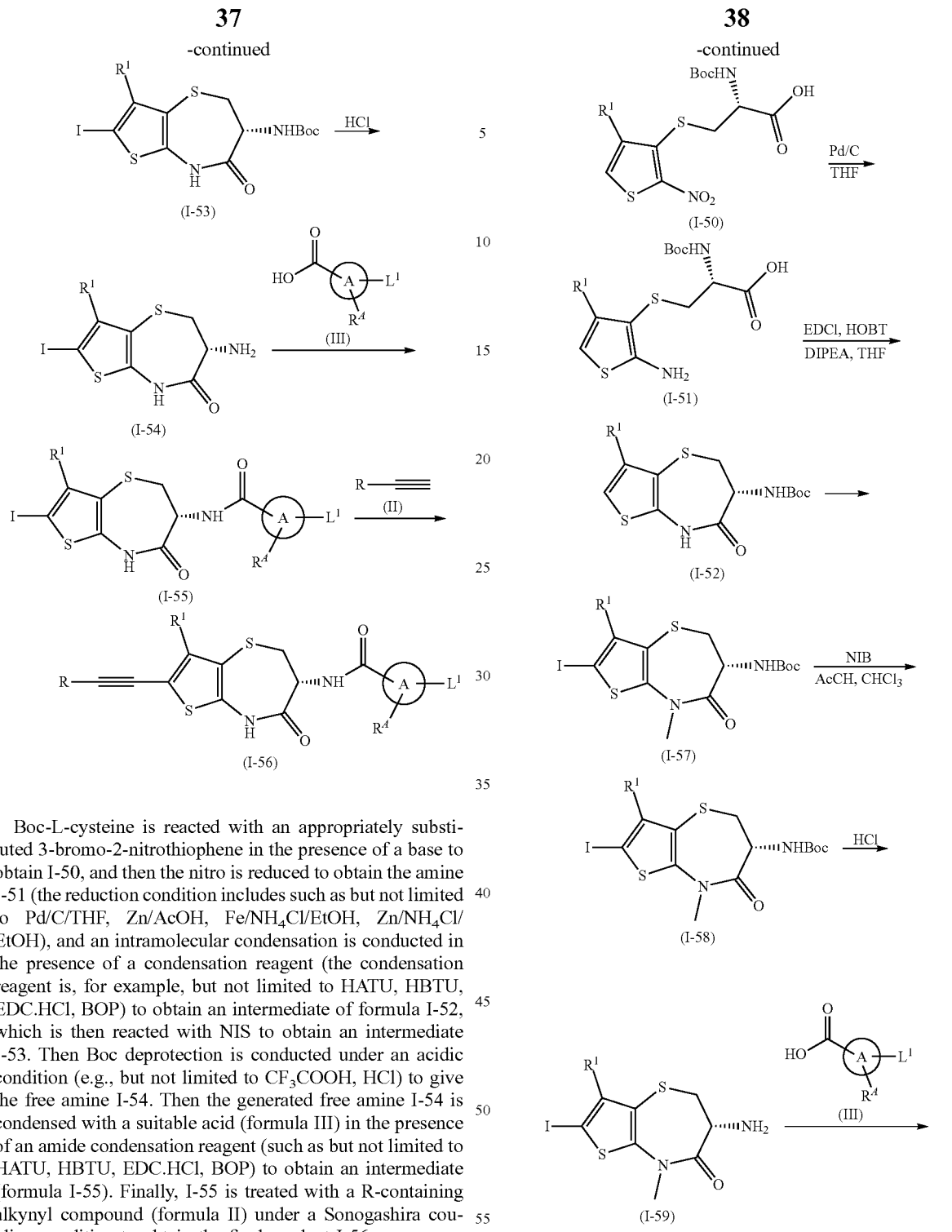

Boc-L-cysteine is reacted with an appropriately substituted 3-bromo-2-nitrothiophene in the presence of a base to obtain I-50, and then the nitro is reduced to obtain the amine I-51 (the reduction condition includes such as but not limited to Pd/C/THF, Zn/AcOH, Fe/NH$_4$Cl/EtOH, Zn/NH$_4$Cl/EtOH), and an intramolecular condensation is conducted in the presence of a condensation reagent (the condensation reagent is, for example, but not limited to HATU, HBTU, EDC.HCl, BOP) to obtain an intermediate of formula I-52, which is then reacted with NIS to obtain an intermediate I-53. Then Boc deprotection is conducted under an acidic condition (e.g., but not limited to CF$_3$COOH, HCl) to give the free amine I-54. Then the generated free amine I-54 is condensed with a suitable acid (formula III) in the presence of an amide condensation reagent (such as but not limited to HATU, HBTU, EDC.HCl, BOP) to obtain an intermediate (formula I-55). Finally, I-55 is treated with a R-containing alkynyl compound (formula II) under a Sonogashira coupling condition to obtain the final product I-56.

Scheme 17

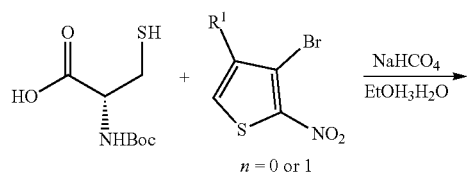

n = 0 or 1

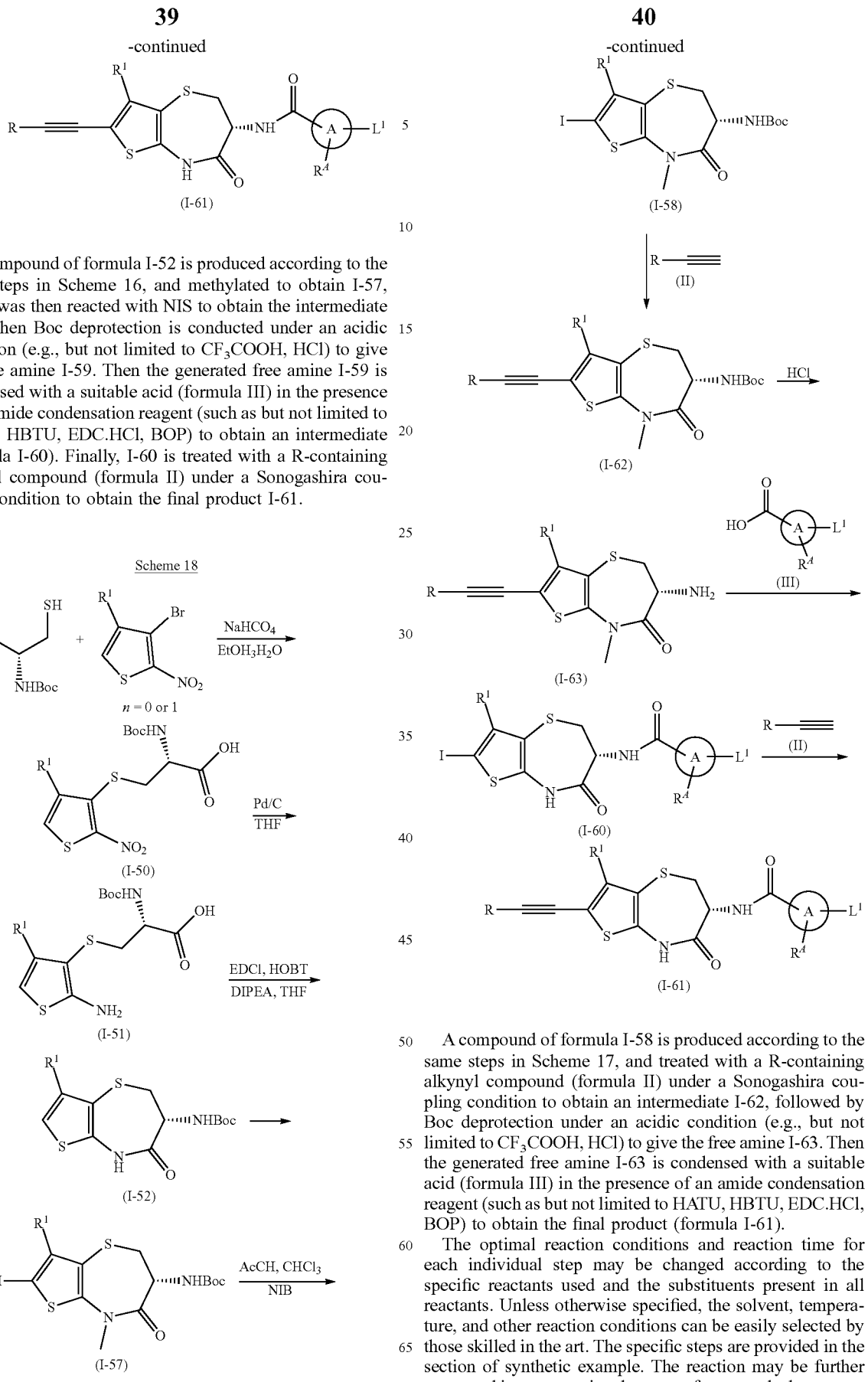

A compound of formula I-52 is produced according to the same steps in Scheme 16, and methylated to obtain I-57, which was then reacted with NIS to obtain the intermediate I-58. Then Boc deprotection is conducted under an acidic condition (e.g., but not limited to $CF_3COOH$, HCl) to give the free amine I-59. Then the generated free amine I-59 is condensed with a suitable acid (formula III) in the presence of an amide condensation reagent (such as but not limited to HATU, HBTU, EDC.HCl, BOP) to obtain an intermediate (formula I-60). Finally, I-60 is treated with a R-containing alkynyl compound (formula II) under a Sonogashira coupling condition to obtain the final product I-61.

A compound of formula I-58 is produced according to the same steps in Scheme 17, and treated with a R-containing alkynyl compound (formula II) under a Sonogashira coupling condition to obtain an intermediate I-62, followed by Boc deprotection under an acidic condition (e.g., but not limited to $CF_3COOH$, HCl) to give the free amine I-63. Then the generated free amine I-63 is condensed with a suitable acid (formula III) in the presence of an amide condensation reagent (such as but not limited to HATU, HBTU, EDC.HCl, BOP) to obtain the final product (formula I-61).

The optimal reaction conditions and reaction time for each individual step may be changed according to the specific reactants used and the substituents present in all reactants. Unless otherwise specified, the solvent, temperature, and other reaction conditions can be easily selected by those skilled in the art. The specific steps are provided in the section of synthetic example. The reaction may be further processed in a conventional manner, for example, by removing the solvent from the residue and further purifying according to methods generally known in the art such as, but not limited to, crystallization, distillation, extraction, grinding, and chromatography. Unless otherwise specified, starting materials and reactants are commercially available or may be prepared by those skilled in the art from commercially available materials using methods described in chemical literatures.

Routine tests, including proper adjustment of the reaction conditions, the reactants and sequence of the synthetic route, the protection of any chemical functional group which may not be compatible with the reaction conditions, and the deprotection at an appropriate point in the reaction sequences of the method, are all included within the scope of the invention. Appropriate protecting groups and methods for protecting and deprotecting different substituents using such appropriate protecting groups are well known to those skilled in the art; examples thereof are found in T. Greene and P. Wuts, Protecting Groups in Chemical Synthesis (third edition), John Wiley & Sons, NY (1999), which is incorporated herein by reference in its entirety. The synthesis of the compounds of the present invention can be achieved by methods similar to those described in the synthetic schemes described above and in the specific examples.

If the starting material is not commercially available, it can be prepared by steps selected from the group consisting of standard organic chemistry techniques, techniques similar to the synthesis of known structural analogs, or techniques similar to the steps described in the above scheme or the section of synthetic examples. When an optically active form of the compound of the present invention is required, it can be obtained by performing one of the steps described herein using an optically active starting material (for example, prepared by asymmetric induction in an appropriate reaction step), or can be obtained by resolving a stereoisomer mixture of a compound or an intermediate by using a standard procedure (for example, chromatographic separation, recrystallization or enzymatic resolution).

Similarly, when a pure geometric isomer of the compound of the present invention is required, it can be obtained by performing one of the steps described above using a pure geometric isomer as a starting material, or can be obtained by resolving a geometric isomer mixture of a compound or an intermediate by using a standard procedure, such as chromatographic separation.

DETAILED EMBODIMENTS

Figure 1:
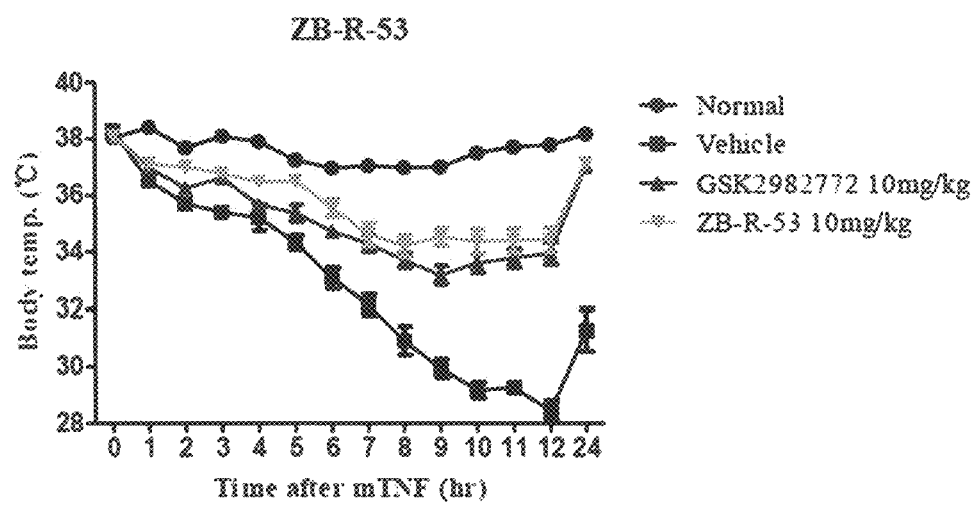
FIGS. 1-4 are respectively the temperature-time graphs of the model mice which were administered with the compound ZB-R-53, ZB-R-54, ZB-R-55, or ZB-R-50 of the present application, normal mice, model mice which is blank control, and the model mice which were administered with the positive control compound in hypothermic shock models.
Figure 2:
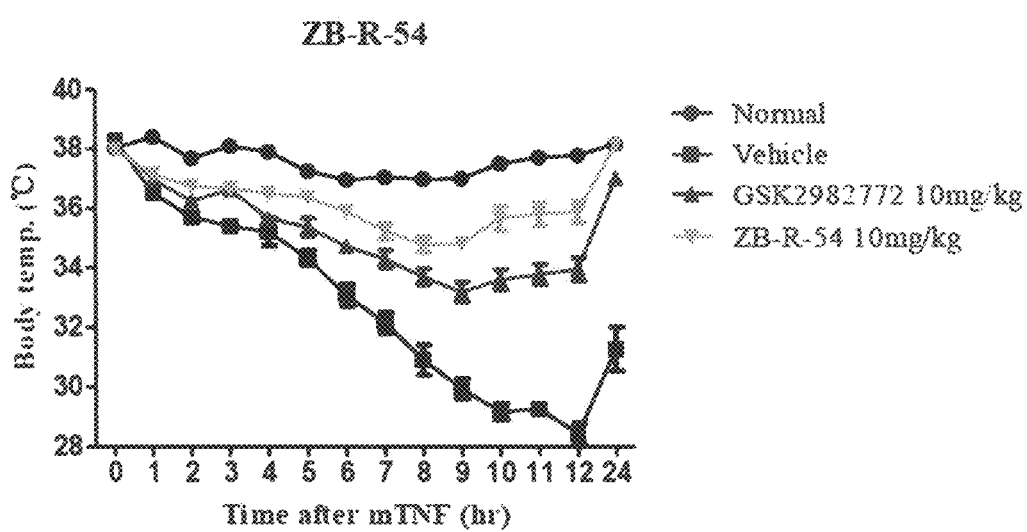
Figure 3:
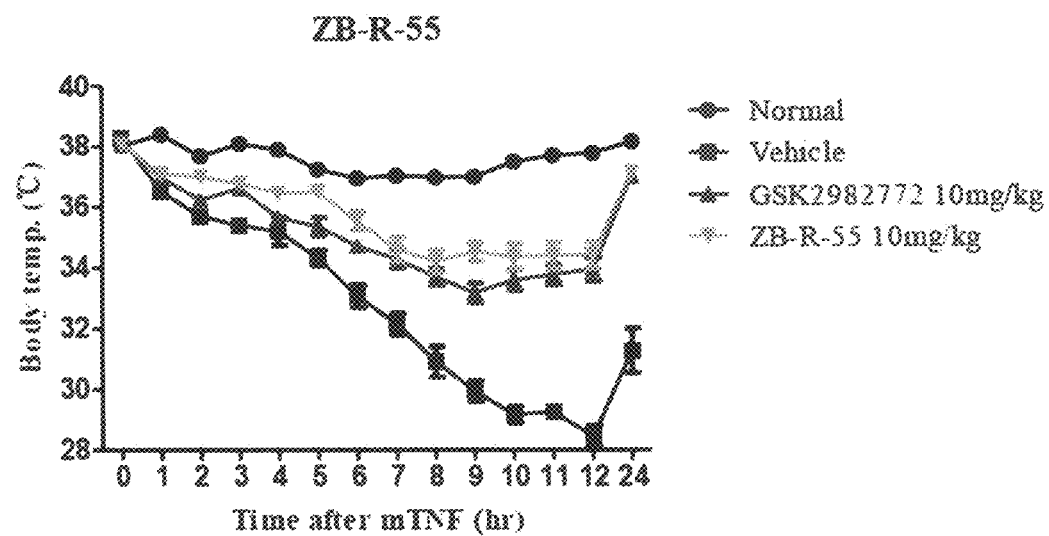
Figure 4:
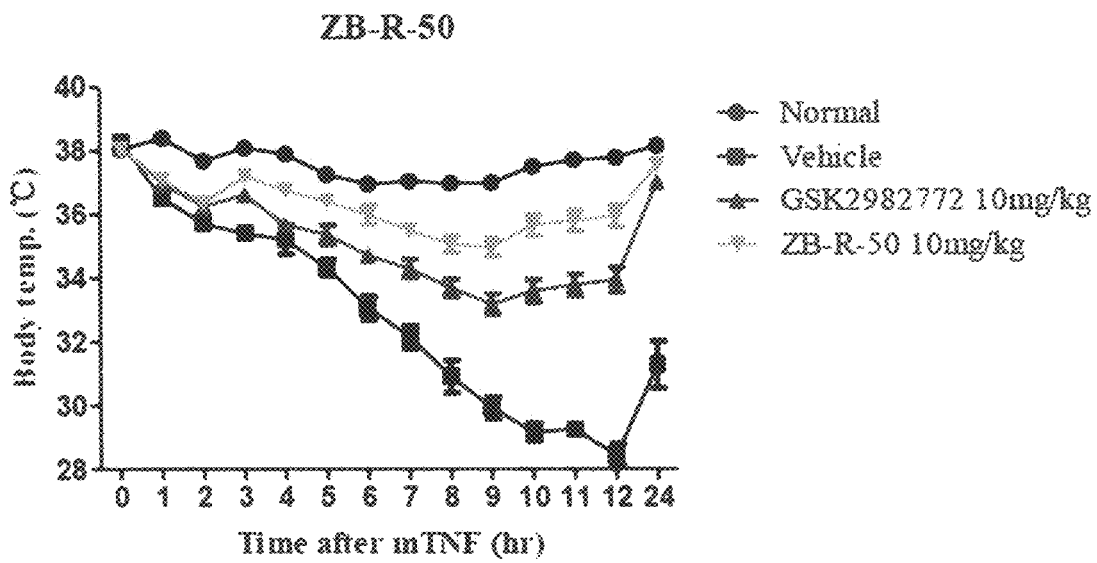
Figure 5:
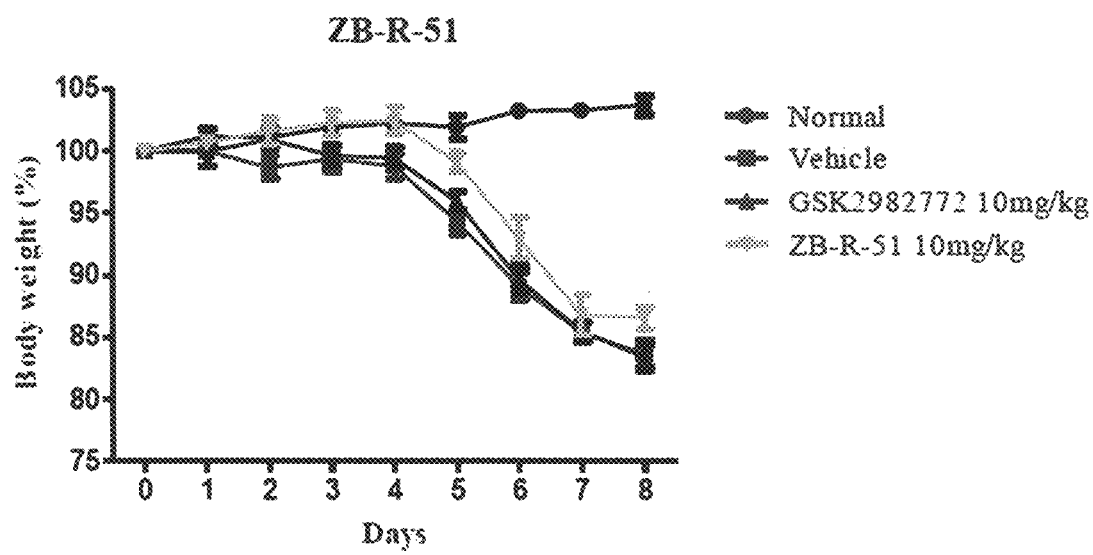
FIGS. 5 and 6 are respectively the body weight-time graphs and the disease activity index-time graphs of normal mice, blank control group, positive control group administered with GSK, and mice administered with the compound ZB-R-51 of the present application.
Figure 6:
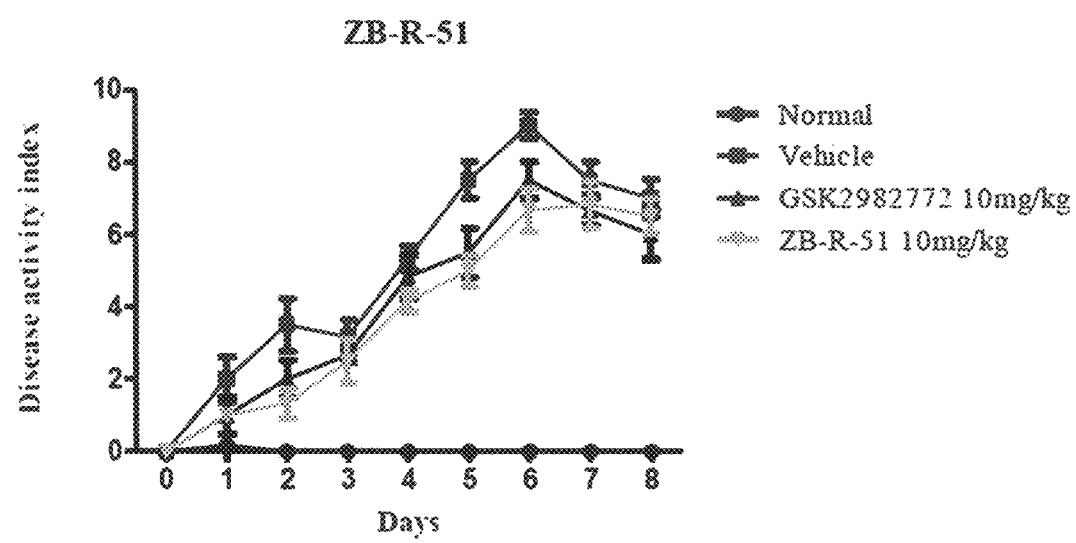
Figure 7:
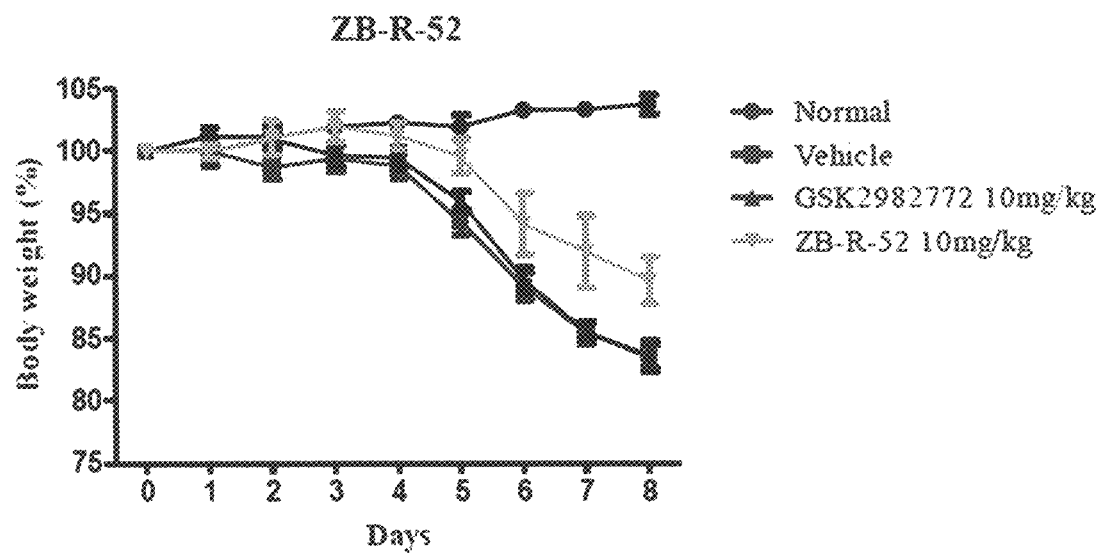
FIGS. 7 and 8 are respectively the body weight-time graphs and the disease activity index-time graphs of normal mice, blank control group, positive control group administered with GSK, and mice administered with the compound ZB-R-52 of the present application.
Figure 8:
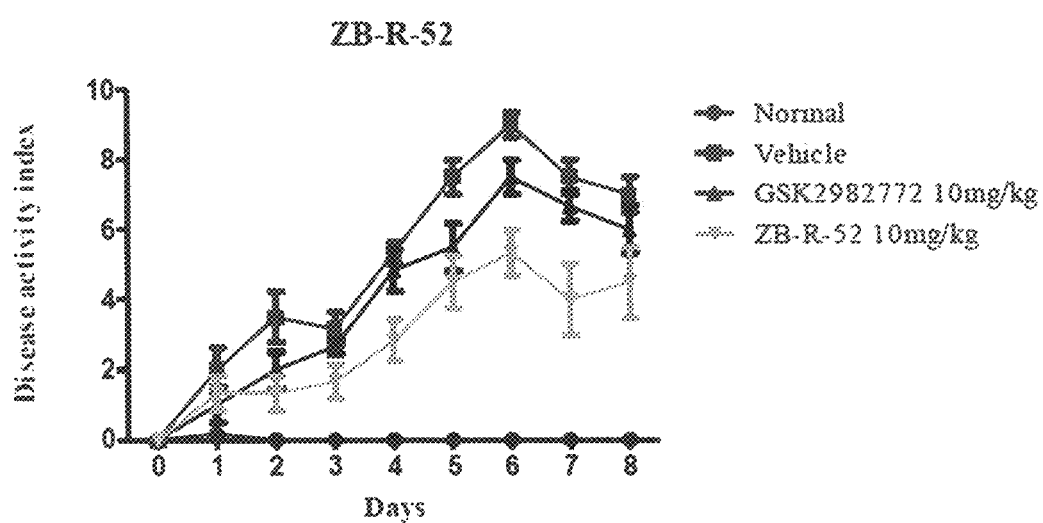

The following examples may be used for illustrative purposes, and are only used to explain the technical solutions of the present invention, and do not intend to limit the present invention to these examples.

Example 1: Preparation of Intermediate M-8

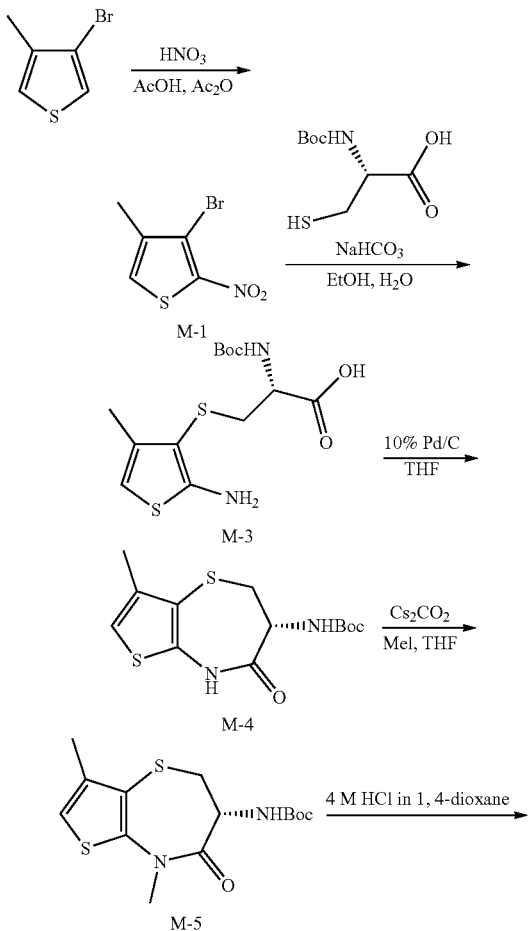

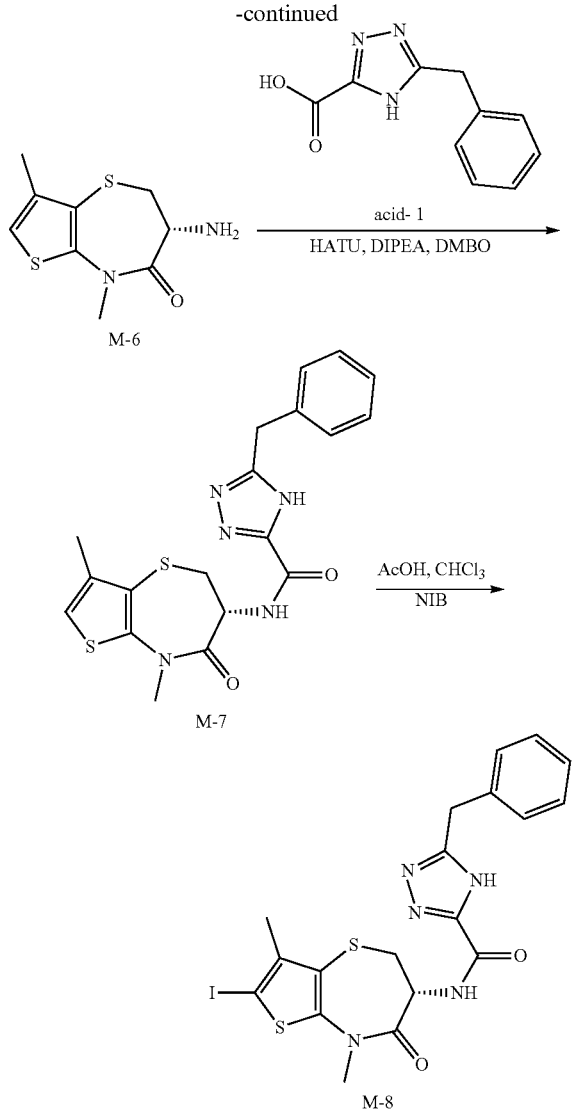

Step Four:

To the tetrahydrofuran solution of M-3 obtained in the previous step, 190 mg of 1-(3-dimethylaminopropyl)-3-ethylcarbodiimide hydrochloride (EDC.HCl), 50 mg of 1-hydroxylbenzotriazole (HOBT), and 200 mg of N,N-diisopropylethylamine (DEPEA) were added, reacted at room temperature for 3 to 4 h, rotary-dried and directly separated by column chromatography to obtain 30 mg of the intermediate M-4.

Step Five:

M-4 (220 mg), cesium carbonate (330 mg) and methyl iodide (125 mg) were dissolved in 10 mL of anhydrous tetrahydrofuran, reacted at room temperature for 2 h, rotary-dried to remove the solvent, and added with water and ethyl acetate to extract. The organic layer was collected, dried over anhydrous sodium sulfate and rotary-dried to obtain M-5. $^1$H NMR (400 MHz, CDCl$_3$) δ 6.84 (m, 1H), 5.55 (d, J=7.4 Hz, 1H), 4.50 (dd, J=18.3, 7.2 Hz, 1H), 3.75 (dd, J=10.8, 6.6 Hz, 1H), 3.39 (s, 3H), 2.99 (t, J=11.2 Hz, 1H), 2.22 (d, J=1.0 Hz, 3H), 1.39 (s, 9H).

Step Six:

M-5 obtained in the previous step was dissolved in 3 mL of a solution of 4M HCl in 1,4-dioxane, reacted for 30 min and directly rotary-dried to obtain M-6.

Step Seven:

M-6 (27 mg) was dissolved in DMSO (1 mL), added with 35 mg of acid-1 (for the preparation of the acid please refer to CN105121432A and *J. Med Chem.* 2017, 60, 1247), HATU (O-(7-azabenzotriazol-1-yl)-N,N,N',N'-tetramethyl-urea hexafluorophosphate, CAS: 148893-10-1, 56 mg) and N,N-diisopropylethylamine (DIPEA) (60 mg), reacted overnight, and added with water and ethyl acetate to extract. The organic layer was collected, dried over anhydrous sodium sulfate, and subjected to column chromatography to obtain M-7.

Step Eight:

M-7 (80 mg) was dissolved in 1 mL of acetic acid and 2.5 mL of chloroform, added with N-iodosuccinimide (NIS) (52 mg), reacted at room temperature for 30 min, added with water, and extracted with dichloromethane. The organic layer was dried over anhydrous sodium sulfate, and rotary-dried to obtain M-8.

Step One:

500 mg of 3-bromo-4-methyl-thiophene (CAS: 30318-99-1) was dissolved in a mixture of acetic anhydride (0.7 mL) and acetic acid (5 mL), cooled in an ice bath for 10 min, added with 150 mL of fuming nitric acid and reacted at room temperature for 4 h. Subsequently, the reaction mixture was poured into an ice water to precipitate a solid, which was filtered to give the intermediate M-1.

Step Two:

N-Boc-L-cysteine (220 mg), M-1 (210 mg) and NaHCO$_3$ (640 mg) were dissolved in ethanol (10 mL) and water (10 mL) and refluxed at 70° C. overnight under argon. The reaction mixture was cooled to room temperature, added with 0.5 M HCl to adjust the system to be acidic, and extracted with ethyl acetate. The organic layer was dried over anhydrous sodium sulfate to obtain the compound M-2.

Step Three:

M-2 (200 mg) and 10% Pd/C (200 mg) were dissolved in tetrahydrofuran (20 mL), replaced with hydrogen for three times, hydrogenated at normal temperature and pressure for 12 h, and filtered off 10% Pd/C through celite to obtain a tetrahydrofuran solution of M-3.

Example 2

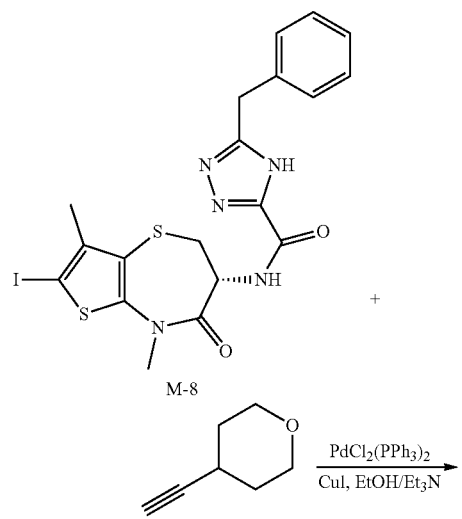

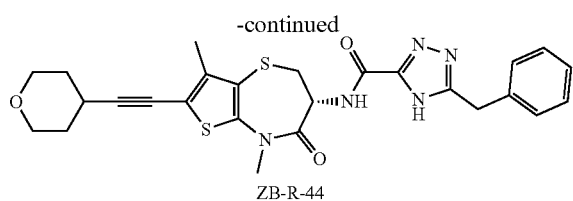

ZB-R-44

M-8 (30 mg), 4-ethynyl-pyran (10 mg), PdCl₂(PPh₃)₂ (CAS: 13965-03-2, 4.6 mg) and cuprous iodide (2.5 mg) were dissolved in 2 mL of ethanol and 0.5 mL of triethylamine, heated to 70° C. under argon, reacted for 3 h, cooled to room temperature, rotary-evaporated under vacuum to remove the solvent, and separated by HPLC to obtain the compound ZB-R-44. HPLC-MS: [M+H]⁺=522.2.

Example 3

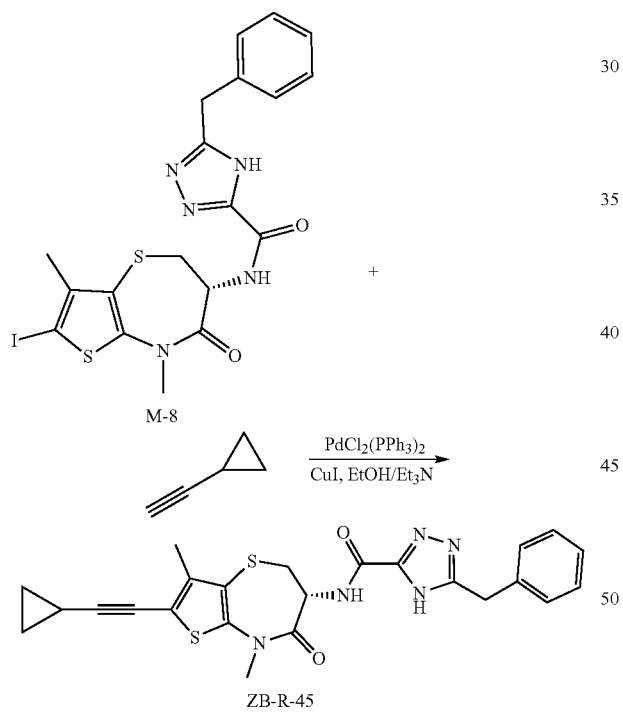

ZB-R-45

M-8 (30 mg), cyclopropylacetylene (10 mg), PdCl₂(PPh₃)₂ (CAS: 13965-03-2, 4.6 mg) and cuprous iodide (2.5 mg) were dissolved in 2 mL of ethanol and 0.5 mL of triethylamine, heated to 70° C. under argon, reacted for 3 h, cooled to room temperature, rotary-evaporated under vacuum to remove the solvent, and separated by HPLC to obtain the compound ZB-R-45. HPLC-MS: [M+H]⁺=478.2. ¹H NMR (400 MHz, MeOD) δ 7.30 (m, 5H), 4.82 (dd, J=11.5, 6.3 Hz, 1H), 4.17 (s, 2H), 3.78 (dd, J=11.1, 6.7 Hz, 1H). 3.37 (s, 3H), 3.28 (t, J=11.5 Hz, 1H), 2.28 (s, 3H), 1.57 (m, 1H), 1.02-0.89 (m, 2H), 0.83-0.76 (m, 2H).

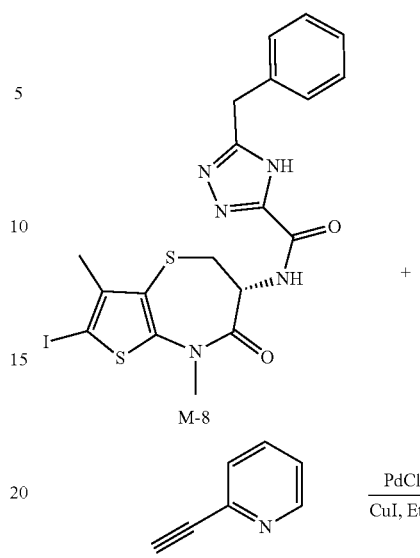

ZB-R-46

M-8 (30 mg), 2-ethynylpyridine (11 mg), PdCl₂(PPh₃)₂ (CAS: 13965-03-2, 4.6 mg) and cuprous iodide (2.5 mg) were dissolved in 2 mL of ethanol and 0.5 mL of triethylamine, heated to 70° C. under argon, reacted for 3 h, cooled to room temperature, rotary evaporated under vacuum to remove the solvent, and separated by HPLC to obtain the compound ZB-R-46. HPLC-MS: [M+H]⁺=515.2. ¹H NMR (400 MHz, MeOD) δ 8.58 (d, J=5.0 Hz, 1H), 7.90 (t, J=7.8 Hz, 1H), 7.67 (d, J=7.8 Hz, 1H), 7.45 (dd, J=7.4, 5.0 Hz, 1H), 7.38-7.20 (m, 5H), 4.90-4.83 (m, 1H). 4.17 (s, 2H), 3.82 (dd. J=11.2, 6.4 Hz, 1H), 3.43 (s, 3H), 3.33 (t, J=11.4 Hz, 1H), 2.47 (s, 3H).

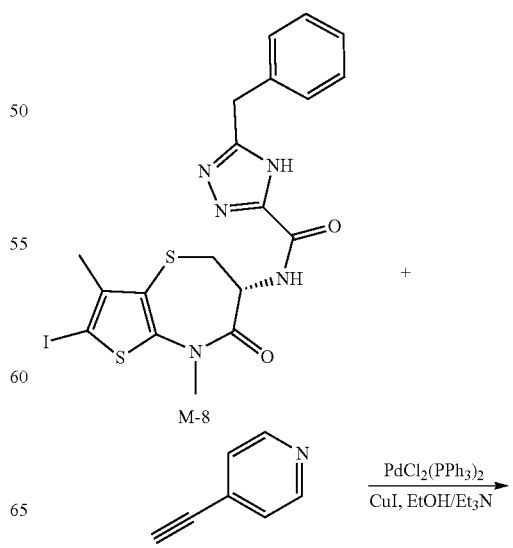

-continued

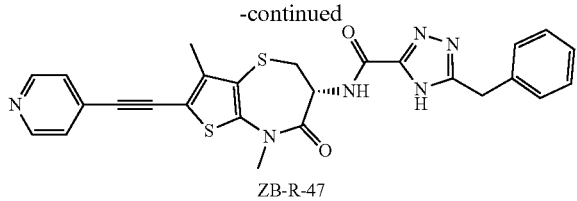

ZB-R-47

M-8 (30 mg), 4-ethynylpyridine (11 mg), PdCl$_2$(PPh$_3$)$_2$ (CAS: 13965-03-2, 4.6 mg) and cuprous iodide (2.5 mg) were dissolved in 2 mL of ethanol and 0.5 mL of triethylamine, heated to 70° C. under argon, reacted for 3 h, cooled to room temperature, rotary evaporated under vacuum to remove the solvent, and separated by HPLC to obtain the compound ZB-R-47. $^1$H NMR (400 MHz, CDCl$_3$) δ 8.58 (d, J=4.5 Hz, 2H), 8.13 (brs, 1H), 7.37 (d, J=4.5 Hz, 2H), 7.25 (m, 5H), 4.92 (m, 1H), 4.14 (s, 2H), 3.87 (dd, J=11.1, 6.6 Hz, 1H), 3.41 (s, 3H), 3.13 (t, J=11.1 Hz, 1H), 2.39 (s, 3H). HPLC-MS: [M+H]$^+$=515.2.

Example 6

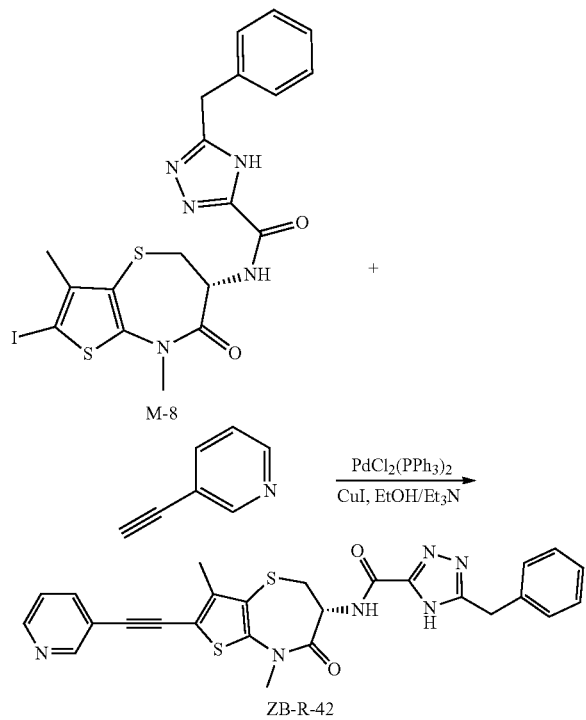

M-8 (30 mg), 3-ethynylpyridine (11 mg), PdCl$_2$(PPh$_3$)$_2$ (CAS: 13965-03-2, 4.6 mg) and cuprous iodide (2.5 mg) were dissolved in 2 mL of ethanol and 0.5 mL of triethylamine, heated to 70° C. under argon, reacted for 3 h, cooled to room temperature, rotary evaporated under vacuum to remove the solvent, and separated by HPLC to obtain the compound ZB-R-42. HPLC-MS: [M+H]$^+$=515.2. $^1$H NMR (400 MHz, MeOD) δ 8.71 (d, J=1.6 Hz, 1H), 8.54 (dd, J=5.0, 1.3 Hz, 1H), 7.99 (d, J=7.9 Hz, 1H), 7.49 (dd, J=7.9, 5.0 Hz, 1H), 7.37-7.22 (m, 5H), 4.88-4.82 (m, 1H). 4.17 (s, 2H), 3.81 (dd, J=11.3, 6.6 Hz, 1H), 3.42 (s, 3H), 3.33 (t, J=11.4 Hz, 1H), 2.43 (s, 3H).

Example 7

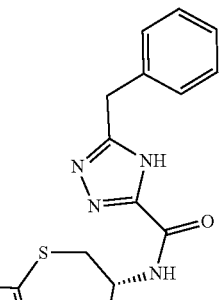

M-8

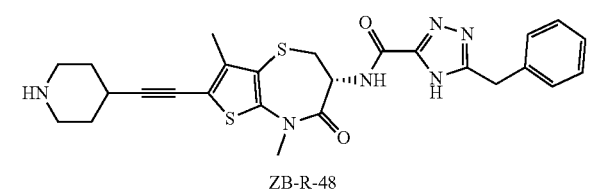

ZB-R-48

M-8 (30 mg), 1-Boc-4-ethynyl-piperidine (11 mg), PdCl$_2$(PPh$_3$)$_2$ (CAS: 13965-03-2, 4.6 mg) and cuprous iodide (2.5 mg) were dissolved in 2 mL of ethanol and 0.5 mL of triethylamine, heated to 70° C. under argon, reacted for 3 h, cooled to room temperature, and added with water and ethyl acetate to extract. The organic layer was collected, dried over anhydrous sodium sulfate, and rotary-dried under vacuum to remove the solvent to obtain an intermediate. Subsequently, the intermediate was added with 2 mL of 4M HCl in 1,4-dioxane, reacted for 30 min, rotary-evaporated under vacuum to remove the solvent, and directly separated by HPLC to obtain the compound ZB-R-48. HPLC-MS: [M+H]$^+$=521.2.

Example 8

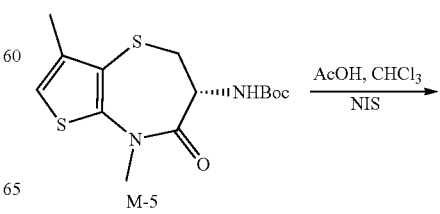

M-5

-continued

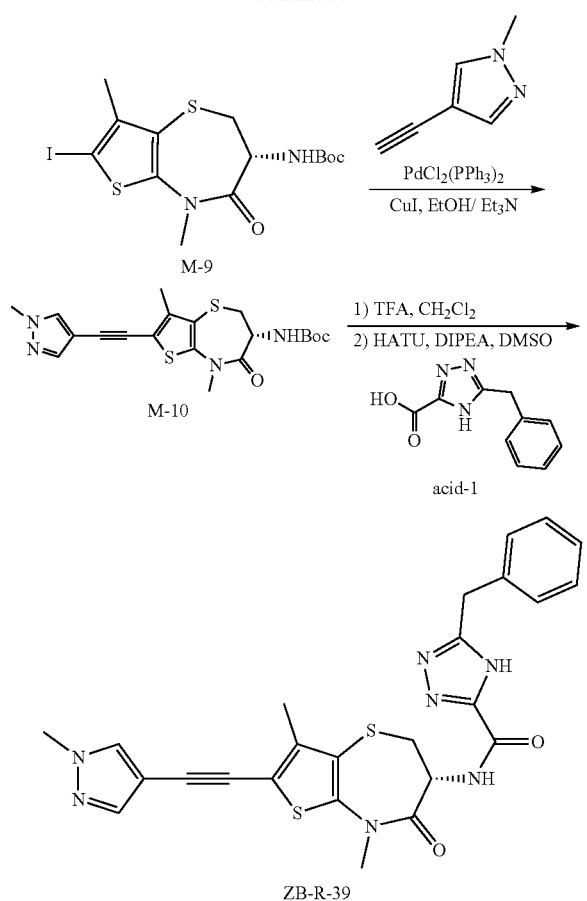

Step 1:

M-5 (80 mg) was dissolved in 1 mL of acetic acid and 2.5 mL of chloroform, added with N-iodosuccinimide (NIS) (65 mg), reacted at room temperature for 30 min, added with water, and extracted with dichloromethane. The organic layer was dried over anhydrous sodium sulfate, and rotary-dried to obtain M-9.

Step 2:

M-9 (20 mg), N-methyl-4-ynylpyrazole (CAS: 39806-89-8)(11 mg), PdCl$_2$(PPh$_3$)$_2$ (CAS: 13965-03-2, 4.6 mg) and cuprous iodide (2.5 mg) were dissolved in 2 mL of ethanol and 0.5 mL of triethylamine, heated to 70° C. under argon, reacted for 3 h, cooled to room temperature, rotary evaporated under vacuum to remove the solvent, and separated by column chromatography to obtain the compound M-10. $^1$H NMR (400 MHz, CDCl$_3$) δ 7.64 (s, 1H), 7.57 (s, 1H), 5.55 (d, J=7.8 Hz, 1H), 4.52 (dt, J=11.3, 7.0 Hz, 1H), 3.92 (s, 3H), 3.76 (dd, J=11.1, 6.4 Hz, 1H), 3.38 (s, 3H), 3.00 (t, J=11.3 Hz, 1H), 2.29 (s, 3H), 1.39 (s, 9H).

Step 3:

M-10 (25 mg) was dissolved in 2 mL of dichloromethane and 1 mL of trifluoroacetic acid, reacted for 1 h, and rotary-dried to remove the solvent to obtain an intermediate amine. Then the intermediate was dissolved in DMSO (1 mL), added with 35 mg of acid-1 (for the preparation of the acid please refer to CN105121432A and *J. Med Chem.* 2017, 60, 1247), HATU (56 mg) and DIPEA (60 mg), reacted overnight, and added with water and ethyl acetate to extract. The organic layer was collected, dried over anhydrous sodium sulfate, rotary-evaporated under vacuum to remove the solvent, and separated by HPLC to obtain the compound ZB-R-39. $^1$H NMR (400 MHz, CDCl$_3$) δ 8.15 (d, J=8.0 Hz, 1H), 7.64 (s, 1H), 7.58 (s, 1H), 7.29-7.19 (m, 5H), 4.92 (dt, J=11.5, 7.4 Hz, 1H), 4.15 (s, 2H), 3.92 (s, 3H), 3.85 (dd, J=10.5, 5.8 Hz, 1H), 3.39 (s, 3H), 3.10 (t, J=11.3 Hz, 1H), 2.32 (s, 3H). HPLC-MS: [M+H]$^+$=518.2

Example 9

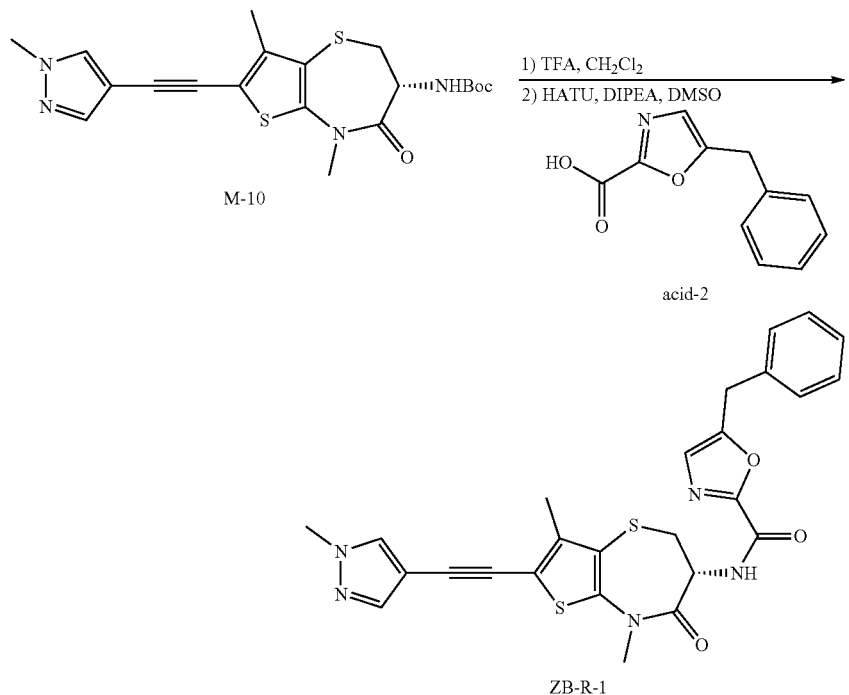

M-10 (25 mg) was dissolved in 2 mL of dichloromethane and 1 mL of trifluoroacetic acid, reacted for 1 h, and rotary-dried to remove the solvent to obtain an intermediate amine. Then the intermediate was dissolved in DMSO (1 mL), added with 35 mg of acid-2 (for the preparation of the acid please refer to CN 105121432A and *J. Med Chem.* 2017, 60, 1247), HATU (56 mg) and DIPEA (60 mg), reacted overnight, added with water and ethyl acetate to extract. The organic layer was collected, dried over anhydrous sodium sulfate, rotary-evaporated under vacuum to remove the solvent, and separated by HPLC to obtain the compound ZB-R-1. HPLC-MS: [M+H]$^+$=518.2.

Example 10

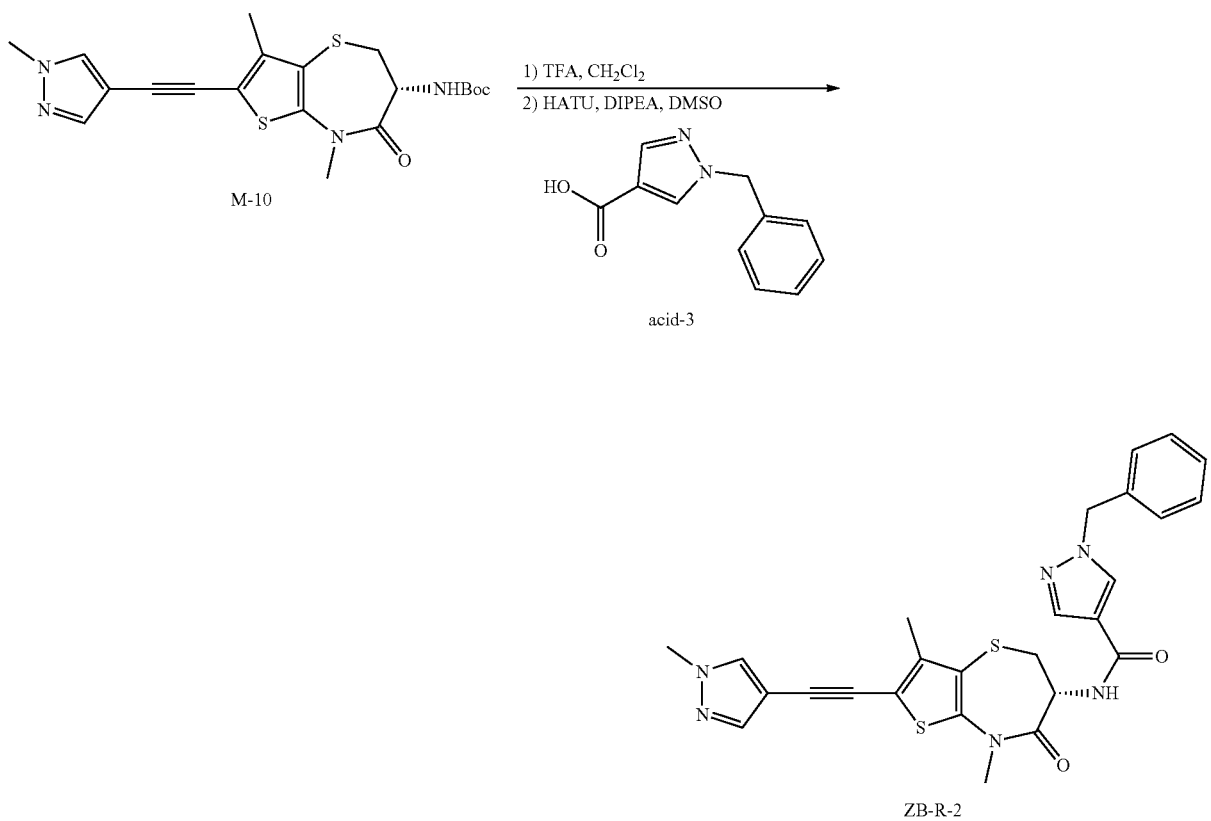

M-10 (25 mg) was dissolved in 2 mL of dichloromethane and 1 mL of trifluoroacetic acid, reacted for 1 h, and rotary-dried to remove the solvent to obtain an intermediate amine. Then the intermediate was dissolved in DMSO (1 mL), added with 35 mg of acid-3 (the acid was purchased commercially, or for the preparation of the acid please refer to CN 105121432A and *J. Med Chem.* 2017, 60, 1247), HATU (56 mg) and DIPEA (60 mg), reacted overnight, added with water and ethyl acetate to extract. The organic layer was collected, dried over anhydrous sodium sulfate, rotary-evaporated under vacuum to remove the solvent, and separated by HPLC to obtain the compound ZB-R-2. HPLC-MS: [M+H]$^+$=517.2.

Example 11

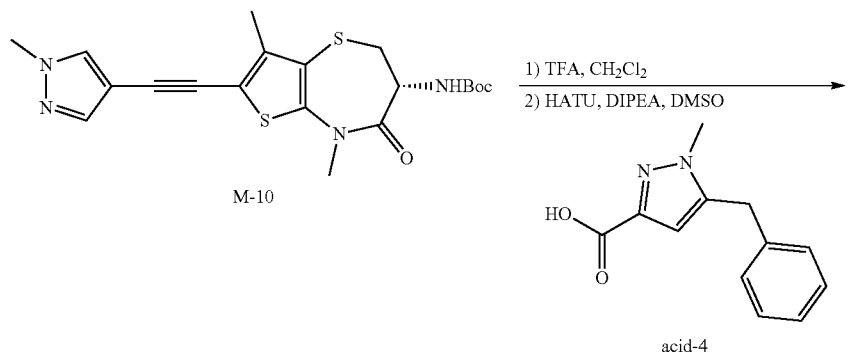

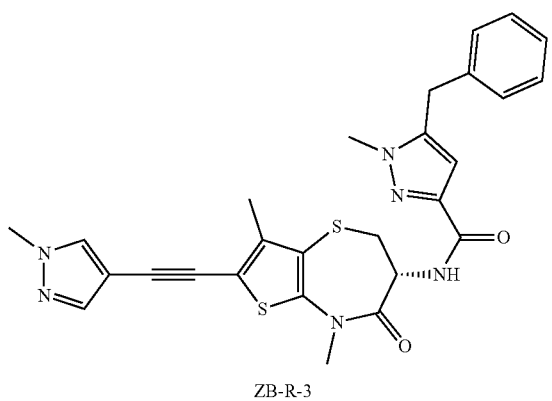

ZB-R-3

M-10 (25 mg) was dissolved in 2 mL of dichloromethane and 1 mL of trifluoroacetic acid, reacted for 1 h, and rotary-dried to remove the solvent to obtain an intermediate amine. Then the intermediate was dissolved in DMSO (1 mL), added with 35 mg of acid-4 (the acid was FA purchased commercially, or for the preparation of the acid please refer to CN105121432A and *J. Med Chem.* 2017, 60, 1247), HATU (56 mg) and DIPEA (60 mg), reacted overnight, and added with water and ethyl acetate to extract. The organic layer was collected, dried over anhydrous sodium sulfate, rotary-evaporated under vacuum to remove the solvent, and separated by HPLC to obtain the compound ZB-R-3. HPLC-MS: $[M+H]^+=531.2$.

Example 12

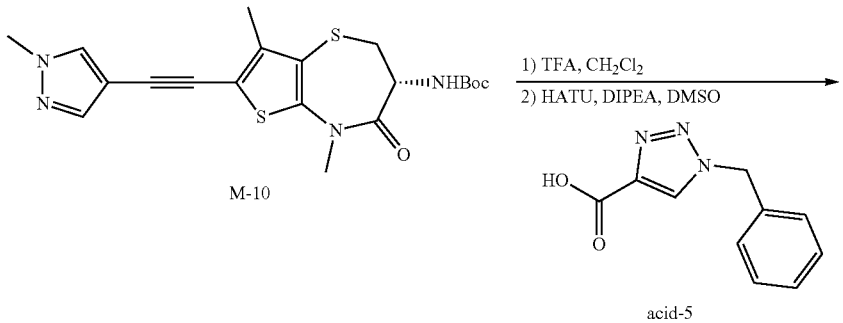

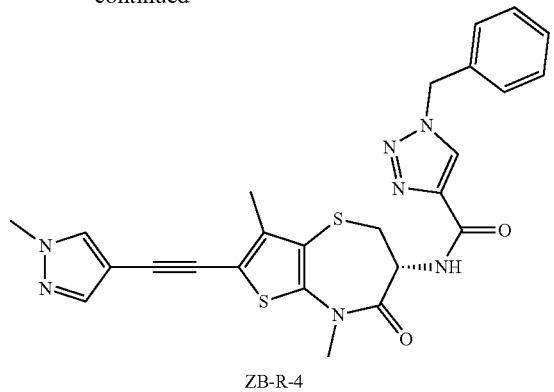

ZB-R-4

M-10 (25 mg) was dissolved in 2 mL of dichloromethane and 1 mL of trifluoroacetic acid, reacted for 1 h, and rotary-dried to remove the solvent to obtain an intermediate amine. Then the intermediate was dissolved in DMSO (1 mL), added with 35 mg of acid-5 (the acid was purchased commercially, or for the preparation of the acid please refer to CN 105121432A and *J. Med Chem.* 2017, 60, 1247), HATU (56 mg) and DIPEA (60 mg), reacted overnight, and added with water and ethyl acetate to extract. The organic layer was collected, dried over anhydrous sodium sulfate, rotary-evaporated under vacuum to remove the solvent, and separated by HPLC to obtain the compound ZB-R-4. HPLC-MS: [M+H]⁺=518.2.

Example 13

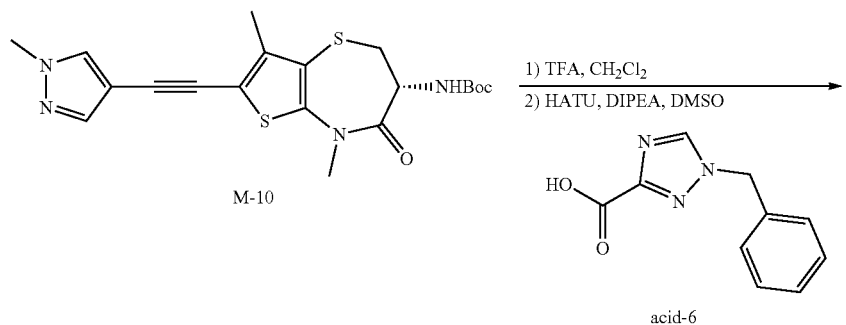

M-10 (25 mg) was dissolved in 2 mL of dichloromethane and 1 mL of trifluoroacetic acid, reacted for 1 h, and rotary-dried to remove the solvent to obtain an intermediate amine. Then the intermediate was dissolved in DMSO (1 mL), added with 35 mg of acid-6 (the acid was purchased commercially, or for the preparation of the acid please refer to CN105121432A and *J. Med Chem.* 2017, 60, 1247), HATU (56 mg) and DIPEA (60 mg), reacted overnight, and added with water and ethyl acetate to extract. Ile organic layer was collected, dried over anhydrous sodium sulfate, rotary-evaporated under vacuum to remove the solvent, and separated by HPLC to obtain compound ZB-R-5. HPLC-MS: [M+H]⁺=518.2.

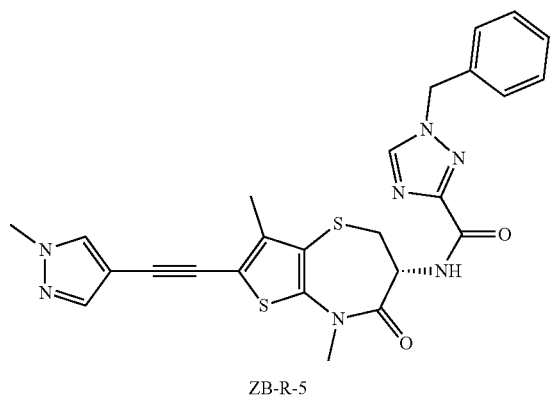

ZB-R-5

Example 14

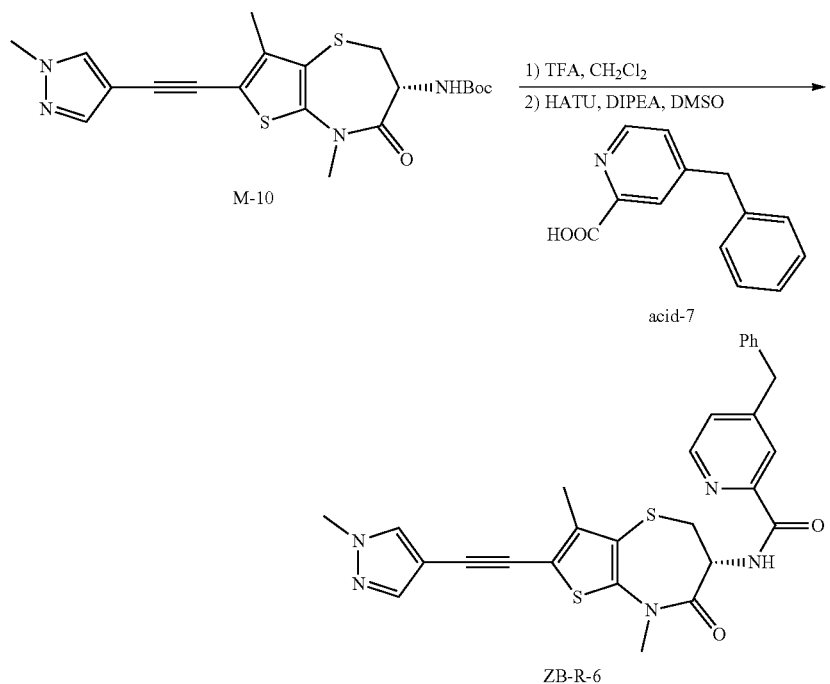

M-10 (25 mg) was dissolved in 2 mL of dichloromethane and 1 mL of trifluoroacetic acid, reacted for 1 h, and rotary-dried to remove the solvent to obtain an intermediate amine. Then the intermediate was dissolved in DMSO (1 mL), added with 35 mg of acid-7 (the acid was purchased commercially, or for the preparation of the acid please refer to CN105121432A and *J. Med Chem.* 2017, 60, 1247), HATU (56 mg) and DIPEA (60 mg), reacted overnight, and added with water and ethyl acetate to extract. The organic layer was collected, dried over anhydrous sodium sulfate, rotary-evaporated under vacuum to remove the solvent, and separated by HPLC to obtain the compound ZB-R-6. HPLC-MS: [M+H]$^+$=528.1.

Example 15

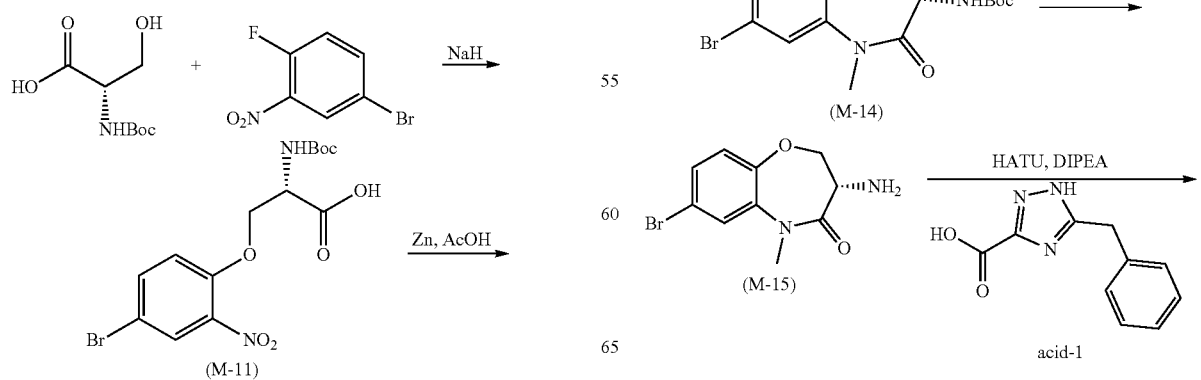

-continued

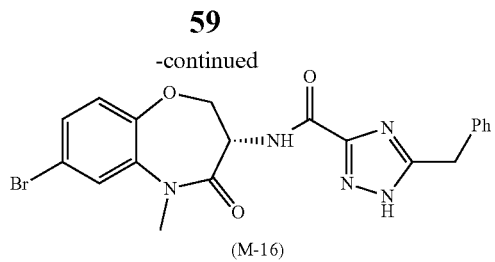

(M-16)

Step One:

60% sodium hydride (430 mg) was dissolved in DMF (10 mL), added dropwise with a solution of N-Boc-L-serine (CAS: 3262-72-4) (1000 mg) in DMF (5 mL), reacted for 10 min, added with 4-bromo-1-fluoro-2-nitrobenzene (CAS: 364-73-8) (1.06 g), further reacted for 3 h, added with 0.5 M HCl to adjust to be weakly acidic, and extracted with ethyl acetate. The organic layer was dried over anhydrous sodium sulfate to obtain the compound M-11.

Step Two:

M-11 (100 mg) was dissolved in acetic acid (2 mL), added with 80 mg of zinc powder, and reacted for 3 h. The solid was filtered off, and the filtrate was rotary-dried, and added with methylene chloride and water to extract. The organic layer was collected, dried over anhydrous sodium sulfate, and rotary-dried to remove the solvent to obtain M-12, which was directly used for the next step without purification.

Step Three:

M-12 obtained in the previous step was dissolved in 3 mL of DMSO, added with HATU (CAS: 148893-10-1, 120 mg) and N,N-diisopropylethylamine (130 mg), reacted for 3 h, and added with ethyl acetate and water to extract. The organic layer was collected, dried over anhydrous sodium sulfate, and rotary-dried to remove the solvent and separated by column chromatography to obtain M-13.

Step Four:

50 mg of M-13 was dissolved in 3 mL DMF, added with 30 mg of potassium carbonate and 24 mg of methyl iodide, reacted for 3 h, and added with 15 ml of water to precipitate a large amount of solid, which was filtered and dried to obtain the intermediate M-14.

Step Five:

40 mg of M-14 was dissolved in 3 mL of methylene chloride, added with 1 ml of trifluoroacetic acid, reacted for 30 min, and rotary-dried to remove the solvent to obtain an intermediate M-15, which was directly used for the next step without purification.

Step Six:

M-15 obtained in the previous step was added with DMSO (1 mL), and then with 27 mg of acid-1 (for the preparation of the acid please refer to CN 105121432A and *J. Med Chem.* 2017, 60, 1247), HATU (62 mg) and DIPEA (60 mg), reacted overnight, and added with water and ethyl acetate to extract. The organic layer was collected, dried over anhydrous sodium sulfate, and pal separated by column chromatography to obtain M-16. $^1$H NMR (400 MHz, MeOD) δ 7.61 (d, J=2.3 Hz, 1H), 7.42 (dd, J=8.6, 2.3 Hz, 1H), 7.32-7.21 (m, 5H), 7.13 (d, J=8.8 Hz, 1H), 4.99 (dd, J=11.5, 7.5 Hz, 1H), 4.57 (dd, J=9.9, 7.5 Hz, 1H), 4.40 (dd, J=11.6, 10 Hz, 1H), 4.14 (s, 2H), 3.37 (s, 3H).

Example 16

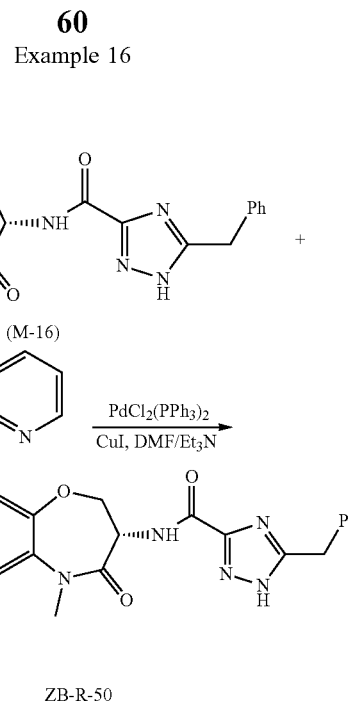

M-16 (25 mg), 2-ethynylpyridine (10 mg), PdCl$_2$(PPh$_3$)$_2$ (CAS: 13965-03-2, 4.6 mg) and cuprous iodide (2.5 mg) were dissolved in 2 mL of N,N-dimethylformamide (DMF) and 1 mL of triethylamine, heated to 85° C. under argon, reacted for 3 h, cooled to room temperature, rotary evaporated under vacuum to remove the solvent, and separated by HPLC to obtain the compound ZB-R-50. HPLC-MS: [M+H]$^+$=479.2. $^1$H NMR. (400 MHz, MeOD) δ 8.64 (m, 1H), 8.01 (t, J=8.0 Hz, 1H), 7.82-7.73 (m, 2H), 7.60-7.52 (m, 2H), 7.36-7.24 (m, 6H), 5.06 (m, 1H), 4.65 (dd, J==10.5, 7.6 Hz, 1H), 4.50 (t, J=10.5 Hz, 1H), 4.19 (s, 2H), 3.46 (s, 3H).

Example 17

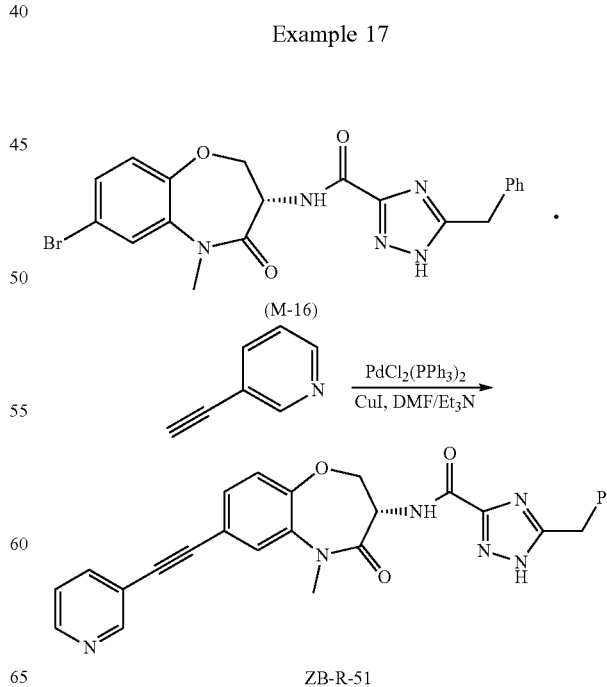

M-16 (25 mg) 3-ethynylpyridine (10 mg) PdCl$_2$(PPh$_3$)$_2$ (CAS-13965-03-2, 4.6 mg) and cuprous iodide (2.5 mg) were dissolved in 2 mL of N,N-dimethylformamide (DMF) and 1 mL of triethylamine, heated to 85° C. under argon, reacted for 3 h, cooled to room temperature, rotary evaporated under vacuum to remove the solvent, and separated by HPLC to obtain the compound ZB-R-51. HPLC-MS: [M+H]$^+$=479.2. $^1$H NMR (400 MHz, DMSO-d$_6$) δ 14.41 (brs, 1H), 8.77 (s, 1H), 8.61 (d, J=3.6 Hz, 1H), 8.45 (brs, 1H), 8.04-7.97 (m, 1H), 7.77 (d, J=1.9 Hz, 1H), 7.52-7.47 (m, 2H), 7.34-7.22 (m, 6H), 4.87 (dt, J=11.4, 7.8 Hz, 1H), 4.65 (t, J=10.3 Hz, 1H), 4.45 (dd, J=9.8, 7.6 Hz, 1H), 4.12 (s, 2H), 3.34 (s, 3H).

Example 18

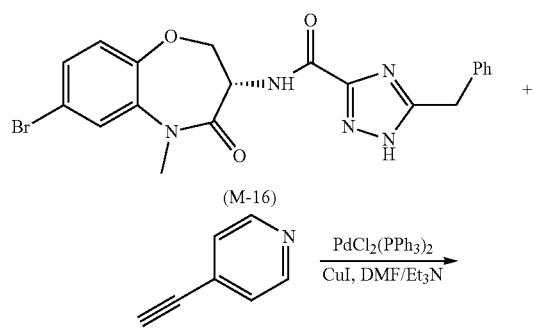

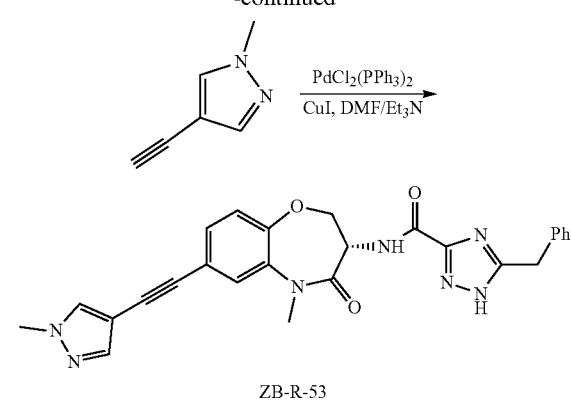

M-16 (25 mg), 4-ethynylpyridine (10 mg), PdCl$_2$(PPh$_3$)$_2$ (CAS: 13965-03-2, 4.6 mg) and cuprous iodide (2.5 mg) were dissolved in 2 mL of N,N-dimethylformamide (DMF) and 1 mL of triethylamine, heated to 85° C. under argon, reacted for 3 h, cooled to room temperature, rotary evaporated under vacuum to remove the solvent, and separated by HPLC to obtain the compound ZB-R-52. HPLC-MS: [M+H]$^+$=479.2. $^1$H NMR (400 MHz, MeOD) δ 8.60 (d, J=5.2 Hz, 2H), 7.71 (s, 1H), 7.60 (d, J=5.6 Hz, 2H), 7.54 (d, J=8.0 Hz, 1H), 7.38-7.23 (m, 6H), 5.07 (dd, J=11.5, 7.5 Hz, 1H). 4.68-4.62 (m, 1H), 4.52-4.46 (m, 1H), 4.19 (s, 2H), 3.46 (s, 3H).

Example 19

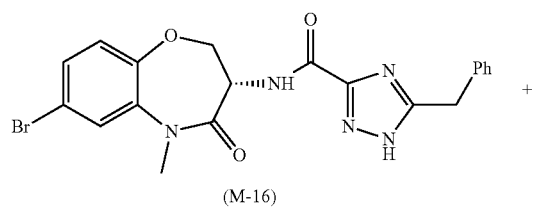

M-16 (25 mg), N-methyl-4-ynylpyrazole (10 mg), PdCl$_2$(PPh$_3$)$_2$ (CAS: 13965-03-2, 4.6 mg) and cuprous iodide (2.5 mg) were dissolved in 2 mL of N,N-dimethylformamide (DMF) and 1 mL of triethylamine, heated to 85° C. under argon, reacted for 3 h, cooled to room temperature, rotary evaporated under vacuum to remove the solvent, and separated by HPLC to obtain the compound ZB-R-53. HPLC-MS: [M+H]$^+$=482.2. $^1$H NMR (400 MHz, MeOD) δ 7.86 (s, 1H), 7.65 (s, 1H), 7.54 (d, J=1.6 Hz, 1H), 7.42-7.19 (m, 7H), 5.05 (dd, J=11.6, 7.4 Hz, 1H), 4.66-4.59 (m, 1H), 4.49-4.40 (m, 1H), 4.18 (s, 2H), 3.92 (s, 3H), 3.43 (s, 3H).

Example 20

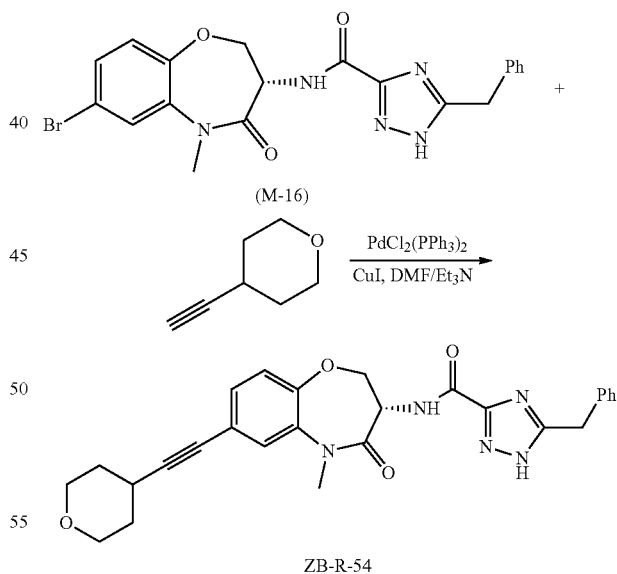

M-16 (25 mg), 4-ethynylpyran (10 mg), PdCl$_2$(PPh$_3$)$_2$ (CAS: 13965-03-2, 4.6 mg) and cuprous iodide (2.5 mg) were dissolved in 2 mL of N,N-dimethylformamide (DMF) and 1 mL of triethylamine, heated to 85° C. under argon, reacted for 3 h, cooled to room temperature, rotary evaporated under vacuum to remove the solvent, and separated by HPLC to obtain the compound ZB-R-54. HPLC-MS: [M+H]$^+$=486.2.

Example 21

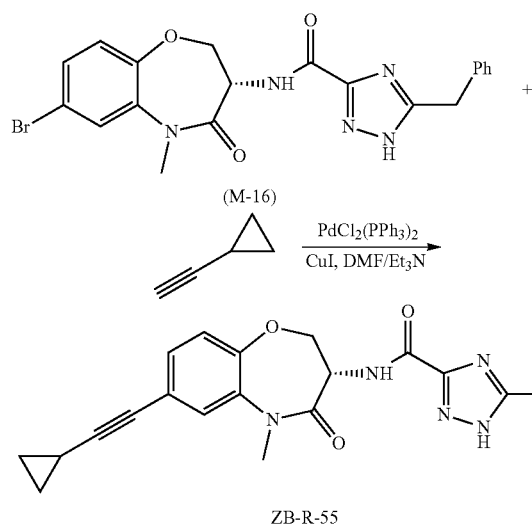

M-16 (25 mg), cyclopropylacetylene (10 mg), PdCl$_2$(PPh$_3$)$_2$ (CAS: 13965-03-2, 4.6 mg) and cuprous iodide (2.5 mg) were dissolved in 2 mL of N,N-dimethylformamide (DMF) and 1 mL of triethylamine, heated to 85° C. under argon, reacted for 3 h, cooled to room temperature, rotary evaporated under vacuum to remove the solvent, and separated by HPLC to obtain the compound ZB-R-55. HPLC-MS: [M+H]$^+$=442.2. $^1$H NMR (400 MHz, MeOD) δ 7.42 (d, J=1.7 Hz, 1H), 7.37-7.24 (m, 6H), 7.15 (d, J=8.3 Hz, 1H), 5.01 (dd, J=11.2, 7.6 Hz, 1H), 4.63-4.56 (m, 1H), 4.45-4.38 (m, 1H), 4.18 (s, 2H), 3.40 (s, 3H), 1.48 (m, 1H), 0.94-0.88 (m, 2H), 0.79-0.73 (m, 2H).

Example 22

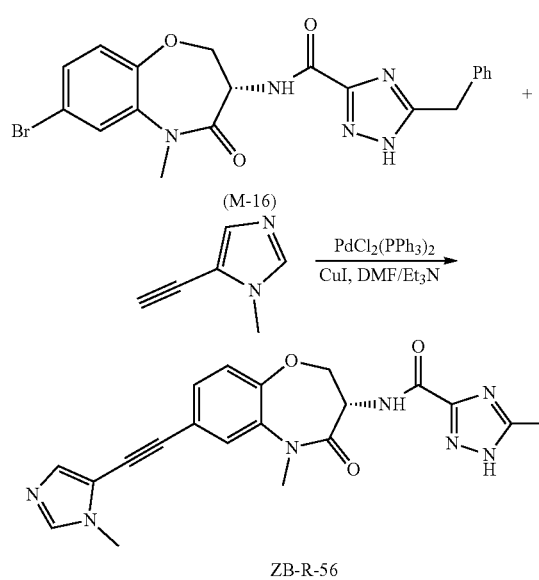

M-16 (25 mg), 5-ethynyl-1-methyl-1H-imidazole (CAS: 71759-92-7, 10 mg), PdCl$_2$(PPh$_3$)$_2$ (CAS: 13965-03-2, 4.6 mg) and cuprous iodide (2.5 mg) were dissolved in 2 mL of N,N-dimethylformamide (DMF) and 1 mL of triethylamine, heated to 85° C.; under argon, reacted for 3 h, cooled to room temperature, rotary evaporated under vacuum to remove the solvent, and separated by HPLC to obtain the compound ZB-R-56. HPLC-MS: [M+H]$^+$=482.2. $^1$H NMR (400 MHz, MeOD) δ 7.75 (s, 1H), 7.65 (s, 1H), 7.48 (d, J=8.3 Hz, 1H), 7.37-7.22 (m, 7H), 5.06 (dd, J=11.6, 7.6 Hz, 1H), 4.68-4.60 (m, 1H), 4.51-4.43 (m, 1H), 4.19 (s, 2H), 3.82 (s, 3H), 3.45 (s, 3H).

Example 23

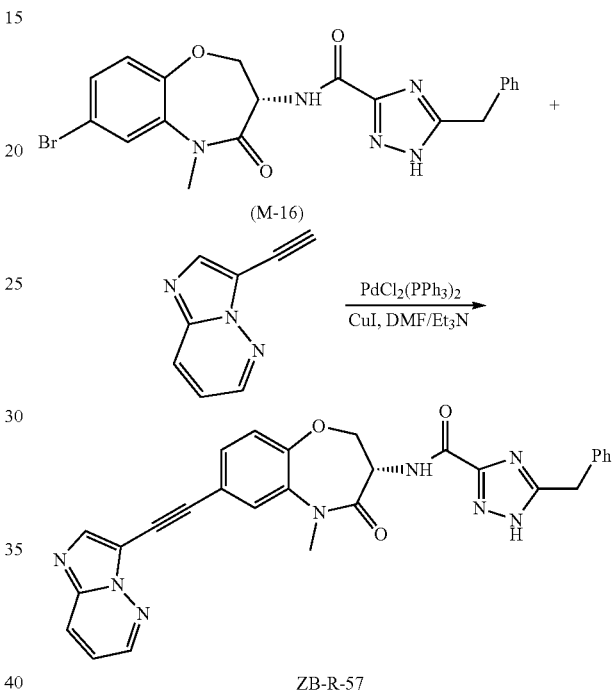

M-16 (25 mg), 3-alkynylimidazo[1,2-B]pyridazine (CAS: 943320-61-4, 13 mg), PdCl$_2$(PPh$_3$)$_2$ (CAS: 13965-03-2, 4.6 mg) and cuprous iodide (2.5 mg) were dissolved in 2 mL of N,N-dimethylformamide (DMF) and 1 mL of triethylamine, heated to 85° C. under argon, reacted for 3 h, cooled to room temperature, rotary evaporated under vacuum to remove the solvent, and separated by HPLC to obtain the compound ZB-R-57. HPLC-MS: [M+H]$^+$=519.2. $^1$H NMR (400 MHz, MeOD) δ 8.63 (d, J=3.6 Hz, 1H), 8.15-8.04 (m, 2H), 7.73 (s, if), 7.56 (d, J=8.1 Hz, 1H), 7.40-7.22 (m, 7H), 5.08 (dd, J=11.1, 7.1 Hz, 1H), 4.69-4.60 (m, 1H), 4.48 (t, J==10.6 Hz, 1H), 4.19 (s, 2H), 3.47 (s, 3H).

Example 24

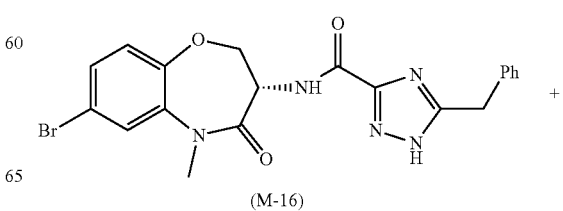

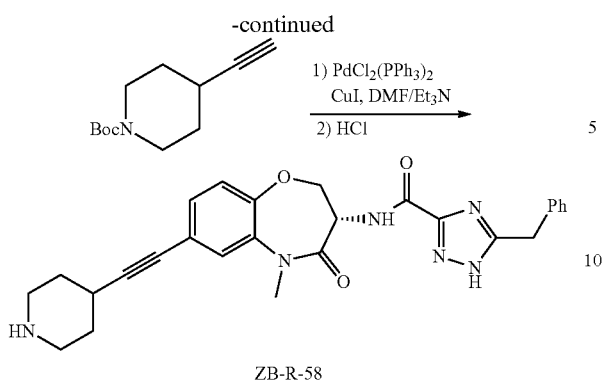

ZB-R-58

M-16 (25 mg), 1-Boc-4-ethynyl-piperidine (12 mg), PdCl$_2$(PPh$_3$)$_2$ (CAS: 13965-03-2, 4.6 mg) and cuprous iodide (2.5 mg) were dissolved in 2 mL of N,N-dimethylformamide (DMF) and 1 mL of triethylamine, heated to 85° C. under argon, reacted for 3 h, cooled to room temperature, and added with water and ethyl acetate to extract. The organic layer was collected, dried over anhydrous sodium sulfate, and rotary-dried to remove the solvent to obtain an intermediate. Subsequently, the intermediate was added with 3 mL of 4M HCl in 1,4-dioxane, reacted for 30 min, rotary-evaporated under vacuum to remove the solvent, and separated by HPLC (mobile phase was acetonitrile and water (containing 0.1% trifluoroacetic acid)) to obtain the compound ZB-R-58. $^1$H NMR (400 MHz, MeOD) δ 7.50 (s, 1H), 7.39-7.18 (m, 7H), 5.02 (dd, J=11.2, 7.6 Hz, 1H), 4.65-4.54 (m, 1H), 4.46 (t, J=10.8 Hz, 1H), 4.19 (s, 2H), 3.47-3.38 (m, 5H), 3.24-3.14 (m, 2H), 3.13-3.04 (m, 1H), 2.25-2.12 (m, 2H), 2.02-1.89 (m, 2H). HPLC-MS: [M+H]$^+$=485.2.

Example 25

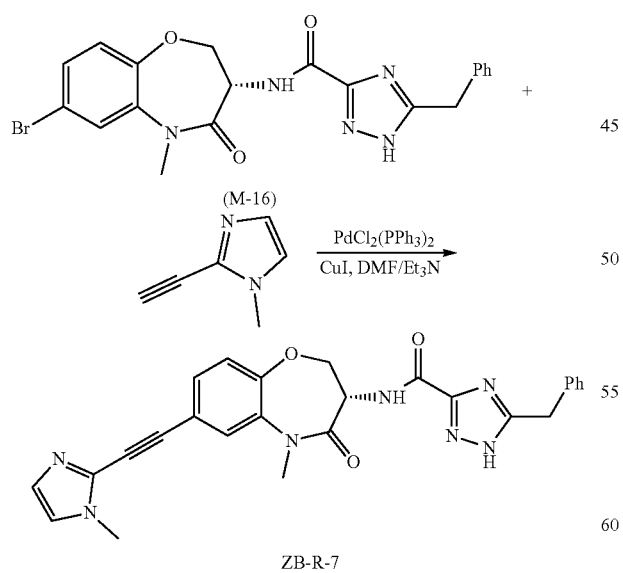

ZB-R-7

M-16 (25 mg), 1-methyl-2-ethynyl-1H-imidazole (CAS: 37067-93-9, 10 mg), PdCl$_2$(PPh$_3$)$_2$ (CAS: 13965-03-2, 4.6 mg) and cuprous iodide (2.5 mg) were dissolved in 2 mL of N,N-dimethylformamide (DMF) and 1 mL of triethylamine, heated to 85° C. under argon, reacted for 3 h, cooled to room temperature, rotary evaporated under vacuum to remove the solvent, and separated by HPLC to obtain the compound ZB-R-7. HPLC-MS: [M+H]$^+$=482.2.

Example 26

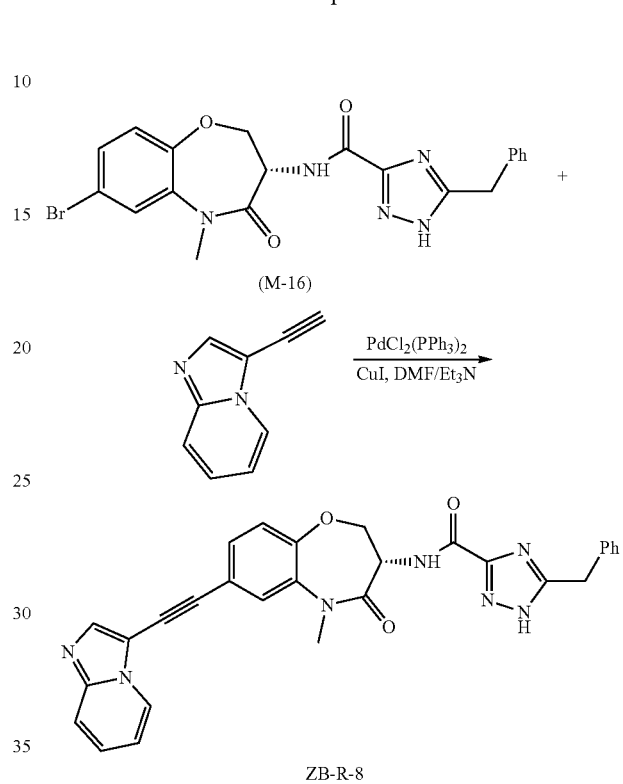

ZB-R-8

M-16 (25 mg), 3-ethynylimidazo[1,2-A]pyridine (CAS: 943320-53-4, 13 mg), PdCl$_2$(PPh$_3$)$_2$ (CAS: 13965-03-2, 4.6 mg) and cuprous iodide (2.5 mg) were dissolved in 2 mL of N,N-dimethylformamide (DMF) and 1 mL of triethylamine, heated to 85° C. under argon, reacted for 3 h, cooled to room temperature, rotary evaporated under vacuum to remove the solvent, and separated by HPLC to obtain the compound ZB-R-8. HPLC-MS: [M+H]$^+$=518.2.

Example 27

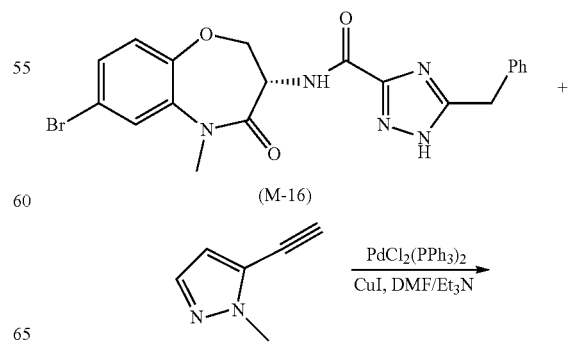

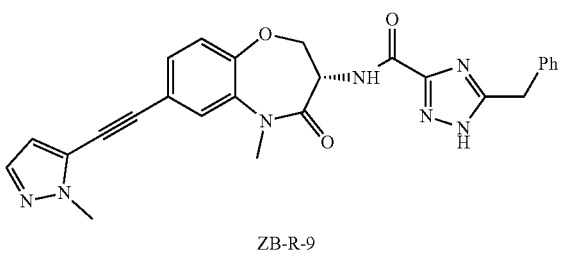

ZB-R-9

M-16 (25 mg), 5-ethynyl-1-methyl-1H-pyrazole (CAS: 19762-15-3, 13 mg), PdCl$_2$(PPh$_3$)$_2$ (CAS: 13965-03-2, 4.6 mg) and cuprous iodide (2.5 mg) were dissolved in 2 mL of N,N-dimethylformamide (DMF) and 1 mL of triethylamine, heated to 85° C. under argon, reacted for 3 h, cooled to room temperature, rotary evaporated under vacuum to remove the solvent, and separated by HPLC to obtain the compound ZB-R-9. HPLC-MS: [M+H]$^+$=482.2.

Example 28

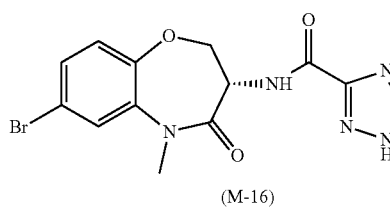

(M-16)

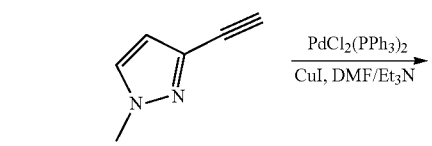

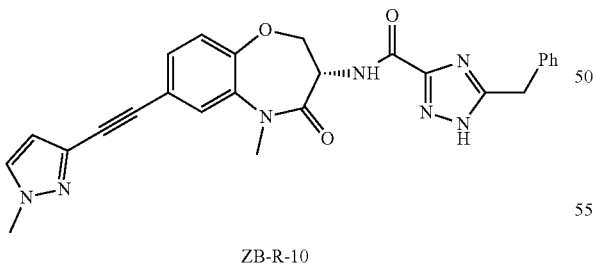

ZB-R-10

M-16 (25 mg), 3-ethynyl-1-methyl-1H-pyrazole (CAS: 61514-59-8, 13 mg), PdCl$_2$(PPh$_3$)$_2$ (CAS: 13965-03-2, 4.6 mg) and cuprous iodide (2.5 mg) were dissolved in 2 mL of N,N-dimethylformamide (DMF) and 1 mL of triethylamine, heated to 85° C. under argon, reacted for 3 h, cooled to room temperature, rotary evaporated under vacuum to remove the solvent, and separated by HPLC to obtain the compound ZB-R-10. HPLC-MS: [M+H]$^+$=482.2.

Example 29

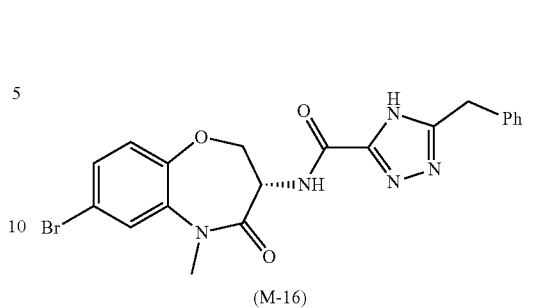

ZB-R-67

M-16 (25 mg), N-methylpropargylamine (CAS: 35161-71-8, 13 mg), PdCl$_2$(PPh$_3$)$_2$ (CAS: 13965-03-2, 4.6 mg) and cuprous iodide (2.5 mg) were dissolved in 2 mL of N,N-dimethylformamide (DMF) and 1 mL of triethylamine, heated to 85° C. under argon, reacted for 3 h, cooled to room temperature, rotary evaporated under vacuum to remove the solvent, and separated by HPLC to obtain the compound ZB-R-67. HPLC-MS: [M+H]$^+$=445.4.

$^1$H NMR (400 MHz, methanol-d$_4$) δ 7.59 (d, J=1.9 Hz, 1H), 7.43 (dd, J=8.3, 1.9 Hz, 1H), 7.36-7.23 (m, 6H), 5.01 (dd, J=11.5, 7.3 Hz, 1H), 4.59 (dd, J=9.8, 7.3 Hz, 1H), 4.48 (dd, J=11.5, 9.8 Hz, 1H), 4.17 (s, 3H), 3.40 (s, 3H), 2.83 (s, 3H).

Example 30

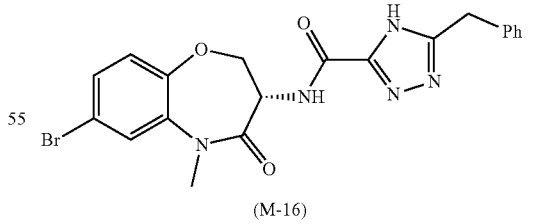

-continued

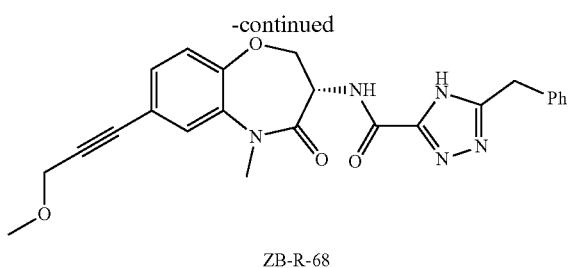

ZB-R-68

M-16 (25 mg), methyl propynyl ether (CAS: 627-41-8, 13 mg), PdCl$_2$(PPh$_3$)$_2$ (CAS: 13965-03-2, 4.6 mg) and cuprous iodide (2.5 mg) were dissolved in 2 mL of N,N-dimethylformamide (DMF) and 1 mL of triethylamine, heated to 85° C. under argon, reacted for 3 h, cooled to room temperature, rotary evaporated under vacuum to remove the solvent, and separated by HPLC to obtain the compound ZB-R-68. HPLC-MS: [M+H]$^+$=446.2. $^1$H NMR (400 MHz, methanol-d$_4$) δ 7.51 (d, J=1.9 Hz, 1H), 7.36 (dd, J=8.3, 1.9 Hz, 1H), 7.34-7.21 (m, 5H), 7.19 (d, J=8.3 Hz, 1H), 5.01 (dd, J=11.5, 7.4 Hz, 1H), 4.59 (dd, J=9.9, 7.4 Hz, 1H), 4.42 (dd, J=11.5, 9.9 Hz, 1H), 4.32 (s, 2H), 4.16 (s, 2H), 3.43 (s, 3H), 3.39 (s, 3H).

Example 31

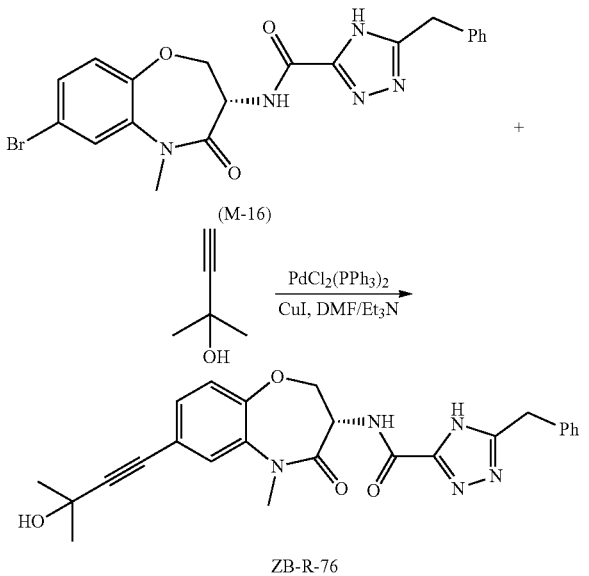

ZB-R-76

M-16 (25 mg), 3-methylbutyn-3-ol (CAS: 115-19-5, 13 mg), PdCl$_2$(PPh$_3$)$_2$ (CAS: 13965-03-2, 4.6 mg) and cuprous iodide (2.5 mg) were dissolved in 2 mL of N,N-dimethylformamide (DMF) and 1 mL of triethylamine, heated to 85° C. under argon, reacted for 3 h, cooled to room temperature, rotary evaporated under vacuum to remove the solvent, and separated by HPLC to obtain the compound ZB-R-76. HPLC-MS: [M+H]$^+$=460.15. $^1$H NMR (400 MHz, methanol-d$_4$) δ 7.44 (d, J=1.8 Hz, 1H), 7.33-7.19 (m, 6H), 7.16 (d, J=8.3 Hz, 1H), 4.99 (dd, J=11.5, 7.4 Hz, 1H), 4.57 (dd, J=9.9, 7.4 Hz, 1H), 4.40 (dd, J=11.5, 9.9 Hz, 1H), 4.14 (s, 2H), 3.37 (s, 3H), 1.56 (s, 6H).

Example 32

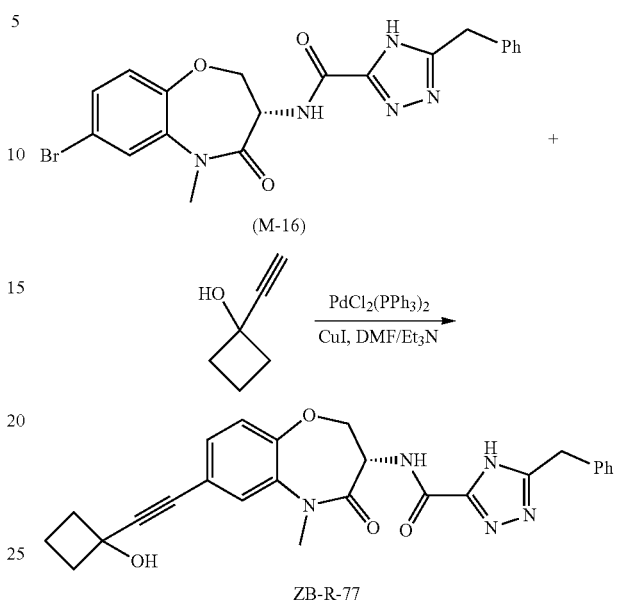

ZB-R-77

M-16 (25 mg), 1-ethynyl cyclobutanol (CAS: 98135-75-2, 13 mg), PdCl$_2$(PPh$_3$)$_2$ (CAS: 13965-03-2, 4.6 mg) and cuprous iodide (2.5 mg) were dissolved in 2 mL of N,N-dimethylformamide (DMF) and 1 mL of triethylamine, heated to 85° C. under argon, reacted for 3 h, cooled to room temperature, rotary evaporated under vacuum to remove the solvent, and separated by HPLC to obtain the compound ZB-R-77. HPLC-MS: [M+H]$^+$=472.2. $^1$H NMR (400 MHz, methanol-d$_4$) δ 7.49 (d, J=1.9 Hz, 1H), 7.34 (dd, J=8.4, 2.0 Hz, 1H), 7.32-7.21 (m, 5H), 7.19 (d, J=8.3 Hz, 1H), 5.01 (dd, J=11.5, 7.4 Hz, 1H), 4.59 (dd, J=9.9, 7.4 Hz, 1H), 4.42 (dd, J=11.5, 9.9 Hz, 1H), 2.52-2.43 (m, 2H), 2.36-2.25 (m, 2H), 1.93-1.82 (m, 2H).

Example 33

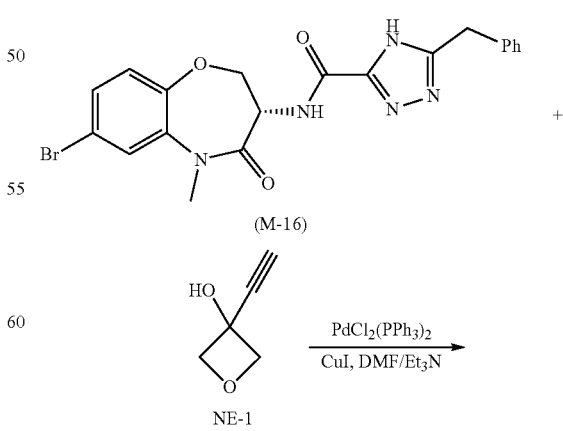

-continued

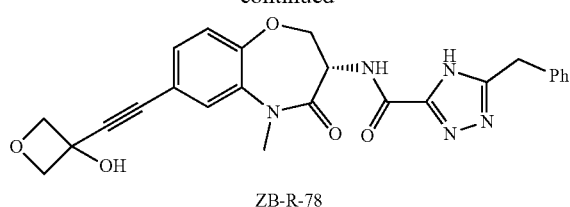

ZB-R-78

M-16 (25 mg), NE-1 (CAS: 1352492-38-6, 13 mg), PdCl$_2$(PPh$_3$)$_2$ (CAS: 13965-03-2, 4.6 mg) and cuprous iodide (2.5 mg) were dissolved in 2 mL of N,N-dimethylformamide (DMF) and 1 mL of triethylamine, heated to 85° C. under argon, reacted for 3 h, cooled to room temperature, rotary evaporated under vacuum to remove the solvent, and separated by HPLC to obtain the compound ZB-R-78. HPLC-MS: [M+H]$^+$=474.2. $^1$H NMR (400 MHz, methanol-d$_4$) δ 7.53 (t, J=1.4 Hz, 1H), 7.41-7.18 (m, 7H), 5.01 (dd, J=11.5, 7.4 Hz, 1H), 4.88 (d, J=6.4 Hz, 2H), 4.71 (d, J=6.4 Hz, 2H), 4.59 (dd, J=9.9, 7.4 Hz, 1H), 4.43 (dd, J=11.5, 9.9 Hz, 1H), 4.15 (s, 3H), 3.38 (d, J=1.0 Hz, 3H).

Example 34

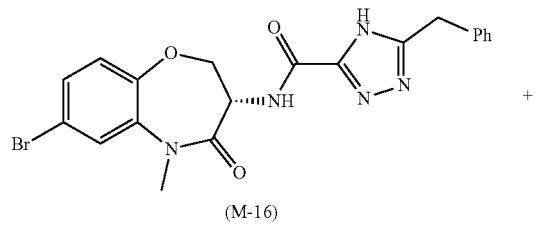

ZB-R-79

M-16 (25 mg), 1-ethynyl cyclohexanol (CAS: 78-27-3, 13 mg), PdCl$_2$(PPh$_3$)$_2$ (CAS: 13965-03-2, 4.6 mg) and cuprous iodide (2.5 mg) were dissolved in 2 mL of N,N-dimethylformamide (DMF) and 1 mL of triethylamine, heated to 85° C. under argon, reacted for 3 h, cooled to room temperature, rotary evaporated under vacuum to remove the solvent, and separated by HPLC to obtain the compound ZB-R-79. HPLC-MS: [M+H]$^+$=500.2. $^1$H NMR (400 MHz, methanol-d$_4$) δ 7.46 (d, J=1.8 Hz, 1H), 7.35-7.20 (m, 6H), 7.18 (d, J=8.3 Hz, 1H), 5.00 (dd, J=11.6, 7.5 Hz, 1H), 4.58 (dd, J=9.9, 7.4 Hz, 1H), 4.41 (dd, J=11.5, 9.9 Hz, 1H), 4.15 (s, 2H), 3.38 (s, 3H), 2.03-1.53 (m, 10H).

Example 35

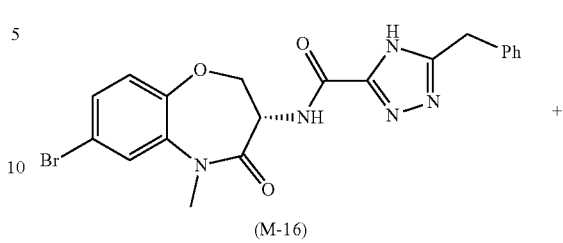

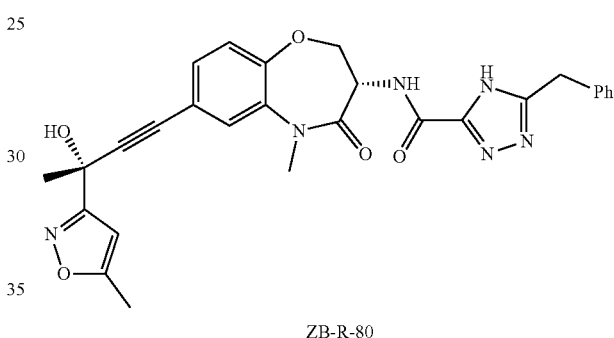

ZB-R-80

M-16 (25 mg), (R)-5-methylisoxazole-3-butyn-2-ol (CAS: 1202771-72-9, 13 mg), PdCl$_2$(PPh$_3$)$_2$ (CAS: 13965-03-2, 4.6 mg) and cuprous iodide (2.5 mg) were dissolved in 2 mL of N,N-dimethylformamide (DMF) and 1 mL of triethylamine, heated to 85° C. under argon, reacted for 3 h, cooled to room temperature, rotary evaporated under vacuum to remove the solvent, and separated by HPLC to obtain the compound ZB-R-80. HPLC-MS: [M+H]$^+$=527.3. $^1$H NMR (400 MHz, methanol-d$_4$) δ 7.52 (d, J=1.8 Hz, 1H), 7.35 (dd, J=8.4, 2.0 Hz, 1H), 7.32-7.20 (m, 5H), 7.17 (d, J=8.3 Hz, 1H), 6.31 (s, 1H), 4.99 (dd, J=11.6, 7.4 Hz, 1H), 4.58 (dd, J=9.9, 7.4 Hz, 1H), 4.41 (dd, J=11.5, 9.9 Hz, 1H), 4.14 (s, 2H), 3.37 (s, 3H), 2.42 (s, 3H), 1.87 (s, 3H).

Example 36

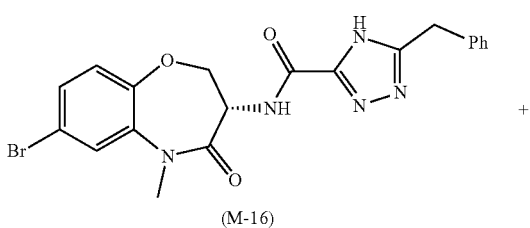

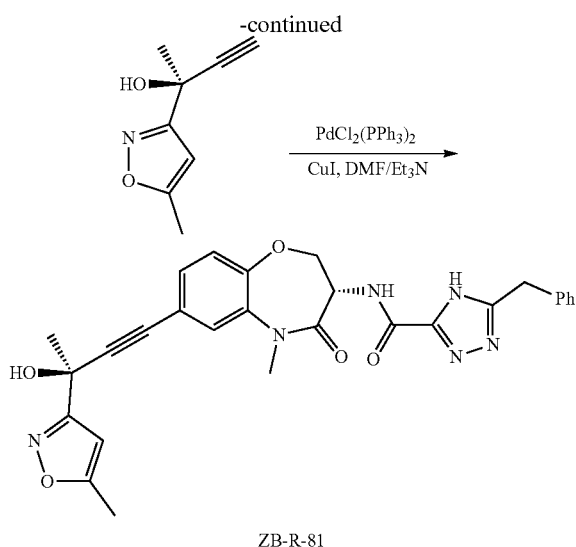

ZB-R-81

M-16 (25 mg), (S)-5-methylisoxazole-3-butyn-2-ol (CAS: 1202771-70-7, 13 mg), PdCl$_2$(PPh$_3$)$_2$ (CAS: 13965-03-2, 4.6 mg), cuprous iodide (2.5 mg) were dissolved in 2 mL of N,N-dimethylformamide (DMF) and 1 mL of triethylamine, heated to 85° C. under argon, reacted for 3 h, cooled to room temperature, rotary evaporated under vacuum to remove the solvent, and separated by HPLC to obtain the compound ZB-R-81. HPLC-MS: [M+H]$^+$=527.3. $^1$H NMR (400 MHz, methanol-d$_4$) δ 7.53 (t, J=1.4 Hz, 1H), 7.37 (dt, J=8.3, 1.4 Hz, 1H), 7.33-7.21 (m, 5H), 7.19 (d, J=8.3 Hz, 1H), 6.31 (s, 1H), 5.00 (dd, J=11.5, 7.4 Hz, 1H), 4.59 (dd, J=9.9, 7.4 Hz, 1H), 4.42 (dd, J=11.5, 9.9 Hz, 1H), 4.15 (s, 2H), 3.38 (s, 3H), 2.43 (s, 3H), 1.87 (s, 3H).

Example 37

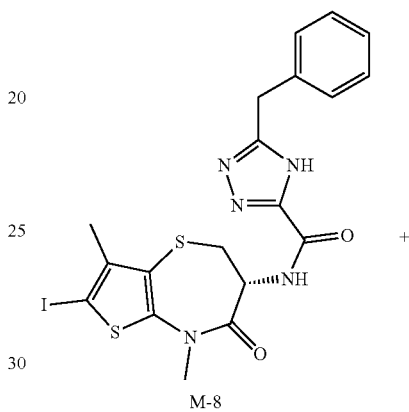

M-8 (30 mg), 5-ethynyl-1-methyl-1H-imidazole (CAS: 71759-92-7, 11 mg), bistriphenylphosphine palladium dichloride [PdCl$_2$(PPh$_3$)$_2$ (CAS: 13965-03-2, 4.6 mg)] and cuprous iodide (2.5 mg) were dissolved in 2 mL of N,N-dimethylformamide (DMF) and 0.5 mL of triethylamine, heated to 70° C. under argon, reacted for 3 h, cooled to room temperature, rotary evaporated under vacuum to remove the solvent, and separated by HPLC to obtain the compound ZB-R-82. HPLC-MS: [M+H]$^+$=518.6. $^1$H NMR (400 MHz, methanol-d$_4$) δ 7.76 (s, 1H), 7.35-7.19 (m, 6H), 4.84 (dd, J=11.6, 6.6 Hz, 1H), 4.14 (s, 2H), 3.78 (dd, J=11.6, 6.6 Hz, 1H), 3.76 (s, 3H), 3.39 (s, 3H), 3.30 (t, J=11.6 Hz, 1H), 2.37 (s, 3H).

Example 38

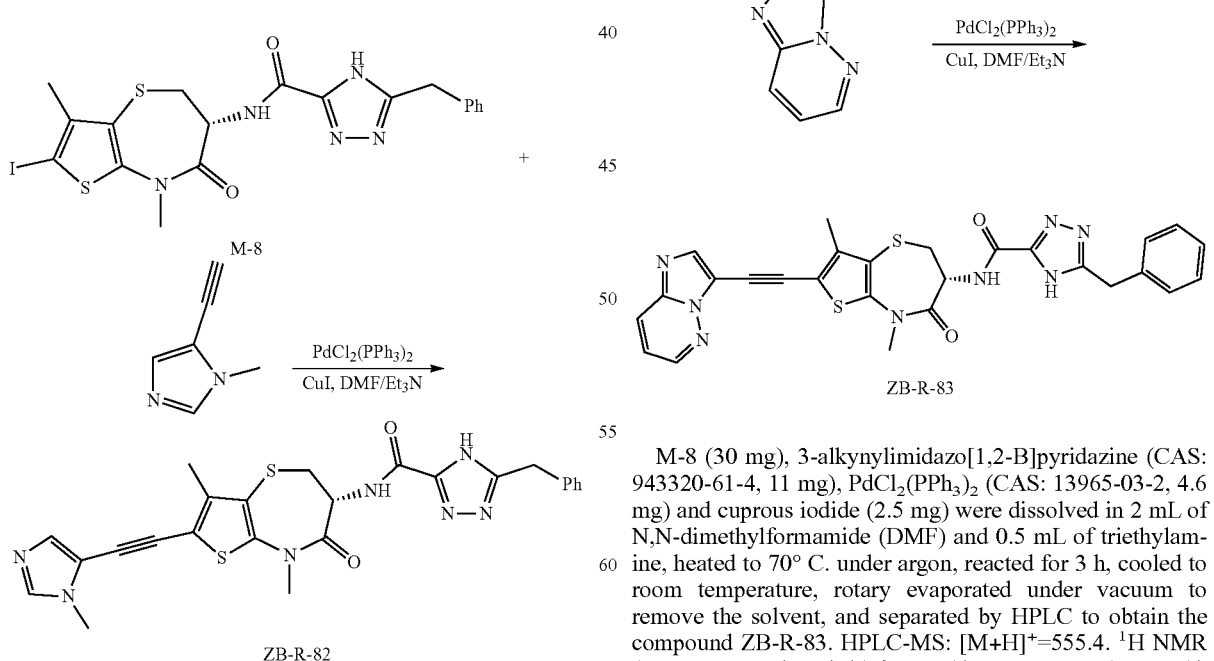

ZB-R-83

M-8 (30 mg), 3-alkynylimidazo[1,2-B]pyridazine (CAS: 943320-61-4, 11 mg), PdCl$_2$(PPh$_3$)$_2$ (CAS: 13965-03-2, 4.6 mg) and cuprous iodide (2.5 mg) were dissolved in 2 mL of N,N-dimethylformamide (DMF) and 0.5 mL of triethylamine, heated to 70° C. under argon, reacted for 3 h, cooled to room temperature, rotary evaporated under vacuum to remove the solvent, and separated by HPLC to obtain the compound ZB-R-83. HPLC-MS: [M+H]$^+$=555.4. $^1$H NMR (400 MHz, methanol-d$_4$) δ 8.61 (d, J=4.4 Hz, 1H), 8.08 (d, J=10.7 Hz, 2H), 7.39-7.19 (m, 6H), 4.86 (dd, J=11.4, 6.5 Hz, 1H), 4.15 (s, 2H), 3.80 (dd, J=11.4, 6.5 Hz, 1H), 3.41 (s, 3H), 3.32 (t, J=11.4 Hz, 1H), 2.42 (s, 3H).

Example 39

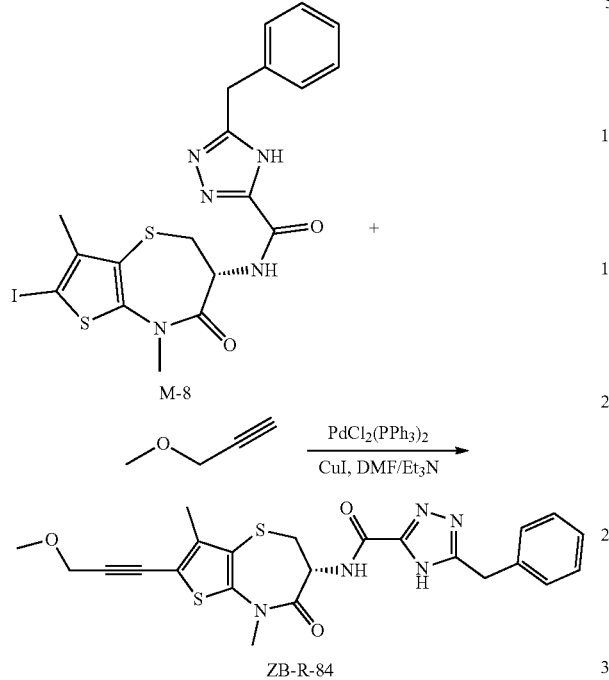

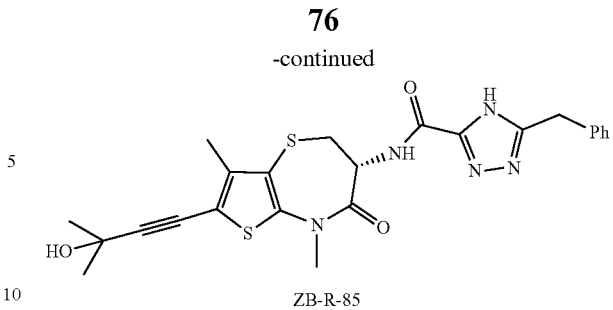

M-8 (30 mg), methyl propynyl ether (CAS: 627-41-8, 11 mg), PdCl$_2$(PPh$_3$)$_2$ (CAS: 13965-03-2, 4.6 mg) and cuprous iodide (2.5 mg) were dissolved in 2 mL of N,N-dimethylformamide (DMF) and 0.5 mL of triethylamine, heated to 70° C. under argon, reacted for 3 h, cooled to room temperature, rotary evaporated under vacuum to remove the solvent, and separated by HPLC to obtain the compound ZB-R-84. HPLC-MS: [M+H]$^+$=482.3. $^1$H NMR (400 MHz, methanol-d$_4$) δ 7.34-7.20 (m, 5H), 4.81 (dd, J=11.5, 6.5 Hz, 1H), 4.38 (s, 2H), 4.15 (s, 2H), 3.76 (dd, J=11.4, 6.5 Hz, 1H), 3.42 (s, 3H), 3.37 (s, 3H), 3.28 (t, J=11.5 Hz, 1H), 2.32 (s, 3H).

Example 40

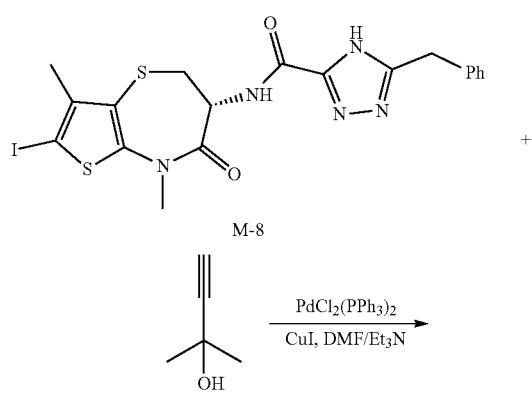

M-8 (30 mg), 3-methylbutyn-3-ol (CAS: 115-19-5, 11 mg), PdCl$_2$(PPh$_3$)$_2$ (CAS: 13965-03-2, 4.6 mg) and cuprous iodide (2.5 mg) were dissolved in 2 mL of N,N-dimethylformamide (DMF) and 0.5 mL of triethylamine, heated to 70° C. under argon, reacted for 3 h, cooled to room temperature, rotary evaporated under vacuum to remove the solvent, and separated by HPLC to obtain the compound ZB-R-85. HPLC-MS: [M+H]$^+$=496.1. $^1$H NMR (400 MHz, methanol-d$_4$) δ 7.34-7.20 (m, 5H), 4.80 (dd, J=11.5, 6.6 Hz, 1H), 4.15 (s, 2H), 3.76 (dd, J=11.5, 6.6 Hz, 1H), 3.36 (s, 3H), 3.28 (t, J===11.5 Hz, 1H), 2.31 (s, 3H), 1.57 (s, 6H).

Example 41

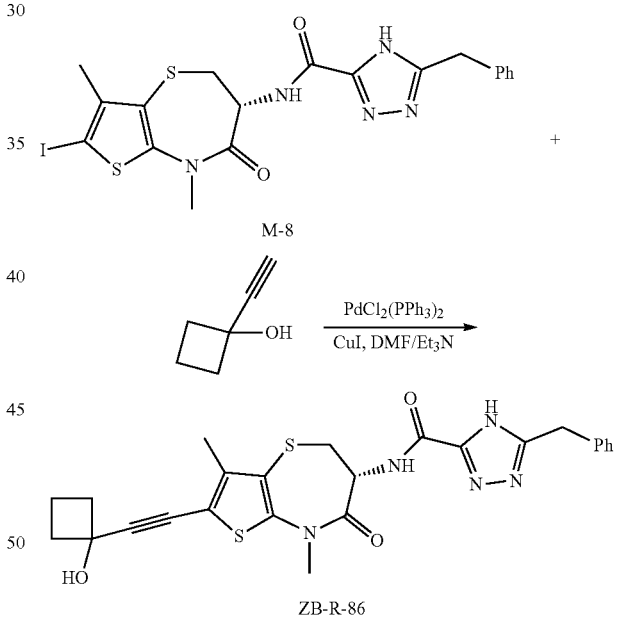

M-8 (30 mg), 1-ethynylcyclobutynol (CAS: 98135-75-2, 11 mg), 13965-03-2, 4.6 mg) and cuprous iodide (2.5 mg) were dissolved in 2 mL of N,N-dimethylformamide (DMF) and 0.5 mL of triethylamine, heated to 70° C. under argon, reacted for 3 h, cooled to room temperature, rotary evaporated under vacuum to remove the solvent, and separated by HPLC to obtain the compound ZB-R-86. HPLC-MS: [M+H]$^+$=508.1. $^1$H NMR (400 MHz, methanol-d$_4$) δ 7.34-7.20 (m, 5H), 4.81 (dd, J=11.5, 6.5 Hz, 1H), 4.15 (s, 2H), 3.76 (dd, J=11.5, 6.5 Hz, 1H), 3.37 (s, 3H), 3.28 (t, J=11.5 Hz, 1H), 2.47 (qd, J=7.8, 6.2, 4.5 Hz, 2H), 2.31-2.28 (m, 5H), 1.88 (td, J=9.1, 4.6 Hz, 2H).

Example 42

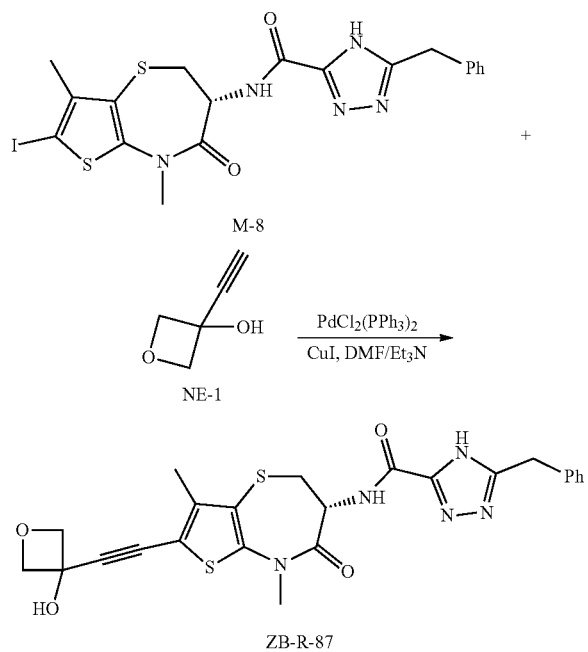

M-8 (30 mg), NE-1 (CAS: 1352492-38-6, 11 mg), PdCl$_2$(PPh$_3$)$_2$ (CAS: 13965-03-2, 4.6 mg), cuprous iodide (2.5 mg) were dissolved in 2 mL of N,N-dimethylformamide (DMF) and 0.5 mL of triethylamine, heated to 70° C. under argon, reacted for 3 h, cooled to room temperature, rotary evaporated under vacuum to remove the solvent, and separated by HPLC to obtain the compound ZB-R-87. HPLC-MS: [M+H]$^+$=510.2. $^1$H NMR (400 MHz, methanol-d$_4$) δ 7.34-7.20 (m, 5H), 4.87 (d, J=6.5 Hz, 2H), 4.81 (dd, J=11.4, 6.4 Hz, 1H), 4.72 (d, J=6.5 Hz, 2H), 4.15 (s, 2H), 3.77 (dd, J=11.4, 6.4 Hz, 1H), 3.38 (s, 3H), 3.30 (t, J=11.4 Hz, 1H), 2.35 (s, 3H).

Example 43

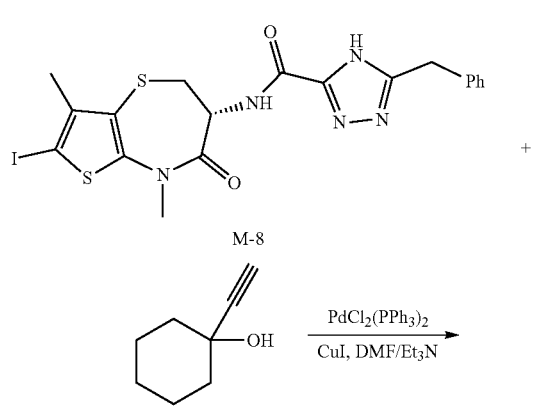

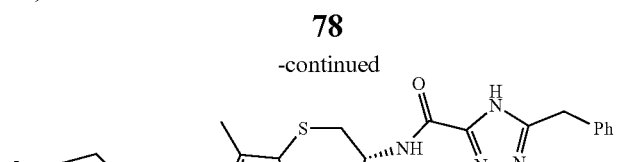

M-8 (30 mg), 1-ethynylcyclohexanol (CAS: 78-27-3, 11 mg), PdCl$_2$(PPh$_3$)$_2$ (CAS: 13965-03-2, 4.6 mg) and cuprous iodide (2.5 mg) were dissolved in 2 mL of N,N-dimethylformamide (DMF) and 0.5 mL of triethylamine, heated to 70° C. under argon, reacted for 3 h, cooled to room temperature, rotary evaporated under vacuum to remove the solvent, and separated by HPLC to obtain the compound ZB-R-88. $^1$H NMR (400 MHz, methanol-d$_4$) δ 7.35-7.20 (m, 5H), 4.81 (dd, J=11.5, 6.5 Hz, 1H), 4.15 (s, 2H), 3.76 (dd, J=11.5, 6.4 Hz, 1H), 3.37 (s, 3H), 3.28 (t, J=11.5 Hz, 1H), 2.32 (s, 3H), 2.07-1.92 (m, 2H), 1.83-1.53 (m, 8H).

Example 44

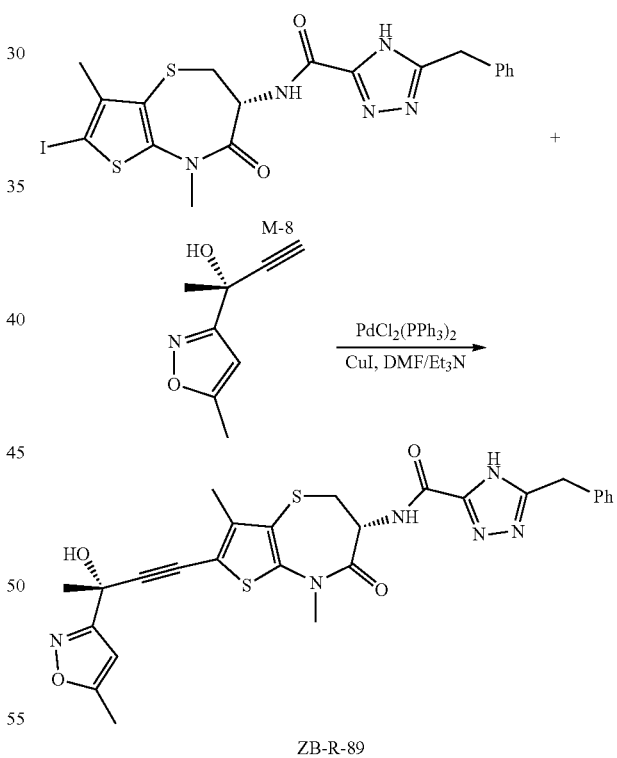

M-8 (30 mg), the alkyne (CAS: 1202771-72-9, 11 mg) in the scheme, PdCl$_2$(PPh$_3$)$_2$ (CAS: 13965-03-2, 4.6 mg) and cuprous iodide (2.5 mg) were dissolved in 2 mL of N,N-dimethylformamide (DMF) and 0.5 mL of triethylamine, heated to 70° C. under argon, reacted for 3 h, cooled to room temperature, rotary evaporated under vacuum to remove the solvent, and separated by HPLC to obtain the compound ZB-R-89. HPLC-MS: [M+H]$^+$=563.3. $^1$H NMR (400 MHz, methanol-d$_4$) δ 7.35-7.18 (m, 5H), 6.29 (s, 1H), 4.80 (dd, J=11.6, 6.6 Hz, 1H), 4.14 (s, 2H), 3.76 (dd, J=11.6, 6.6 Hz, 1H), 3.36 (s, 3H), 3.28 (t, J=11.6 Hz, 1H), 2.43 (s, 3H), 2.32 (s, 3H), 1.87 (s, 3H).

Example 45

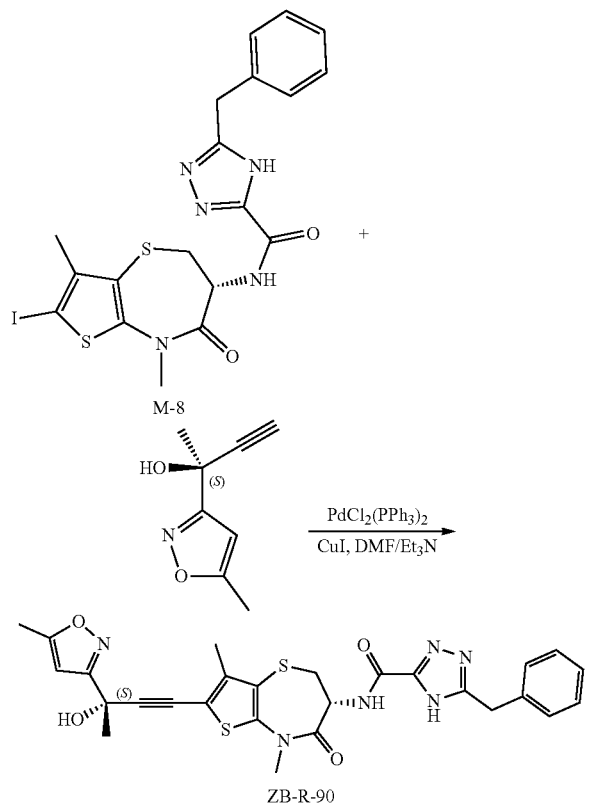

M-8 (30 mg), the alkyne (CAS: 1202771-70-7, 11 mg) in the scheme, PdCl$_2$(PPh$_3$)$_2$ (CAS: 13965-03-2, 4.6 mg) and cuprous iodide (2.5 mg) were dissolved in 2 mL of N,N-dimethylformamide (DMF) and 0.5 mL of triethylamine, heated to 70° C. under argon, reacted for 3 h, cooled to room temperature, rotary evaporated under vacuum to remove the solvent, and separated by HPLC to obtain the compound ZB-R-90. [M+H]$^+$=563.3. $^1$H NMR (400 MHz, methanol-d$_4$) δ 7.35-7.18 (m, 5H), 6.29 (s, 1H), 4.80 (dd, J=11.6, 6.6 Hz, 1U), 4.14 (s, 2H), 3.76 (dd, J=11.6, 6.6 Hz, 1H), 3.36 (d, J=0.9 Hz, 3H), 3.28 (d, J=11.6 Hz, 1H), 2.43 (s, 3H), 2.32 (s, 3H), 1.88 (s, 3H).

Example 46

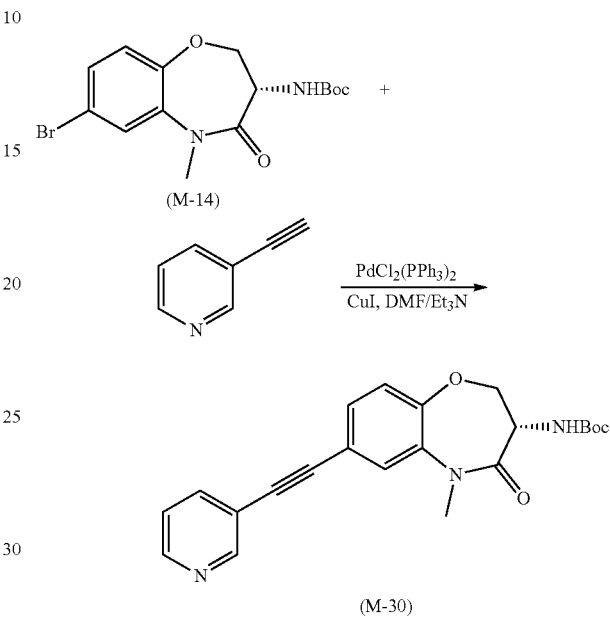

M-14 (25 mg), 3-ethynylpyridine (10 mg), PdCl$_2$(PPh$_3$)$_2$ (CAS: 13965-03-2, 4.6 mg) and cuprous iodide (2.5 mg) were dissolved in 2 mL of N,N-dimethylformamide (DMF) and 1 mL of triethylamine, heated to 85° C. under argon, reacted for 3 h, cooled to room temperature, rotary evaporated under vacuum to remove the solvent, and separated by HPLC to obtain the compound M-30. [M+H]$^+$=394.1.

Example 47

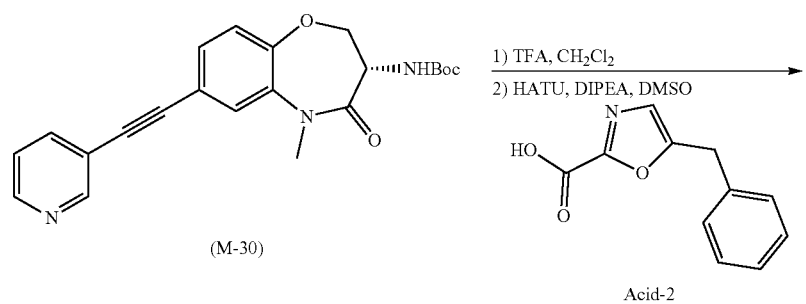

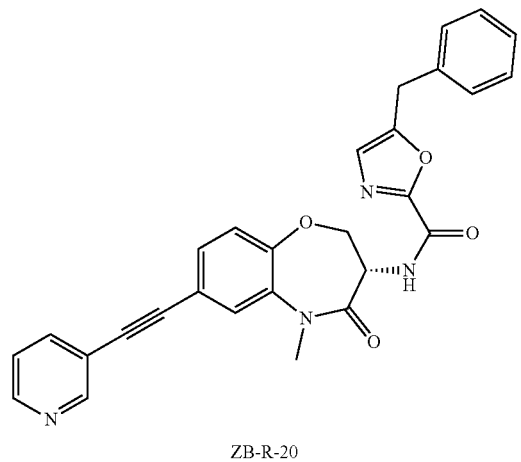

ZB-R-20

M-30 (25 mg) was dissolved in 2 mL of dichloromethane and 1 mL of trifluoroacetic acid, reacted for 1 h, and rotary-dried to remove the solvent to obtain an intermediate amine. The intermediate was dissolved in DMSO (1 mL), added with 35 mg of acid-2 (for the preparation of the acid please refer to CN 105121432A and *J. Med Chem.* 2017, 60, 1247), HATU (56 mg) and DIPEA (60 mg), reacted overnight, and added with water and ethyl acetate to extract. The organic layer was collected, dried over anhydrous sodium sulfate, rotary-evaporated under vacuum to remove the solvent, and separated by HPLC to obtain the compound ZB-R-20. HPLC-MS: [M+H]$^+$=479.1.

Example 48 rotary-dried to remove the solvent to obtain an intermediate amine. The intermediate was dissolved in DMSO (1 mL), added with 35 mg of acid-3 (the acid was purchased commercially, or for the preparation of the acid please refer to CN 105121432A and *J. Med Chem.* 2017, 60, 1247), HATU (56 mg) and DIPEA (60 mg), reacted overnight, and added with water and ethyl acetate to extract. The organic layer was collected, dried over anhydrous sodium sulfate, rotary-evaporated under vacuum to remove the solvent, and separated by HPLC to obtain the compound ZB-R-21. HPLC-MS: [M+H]$^+$=478.2.

Example 49

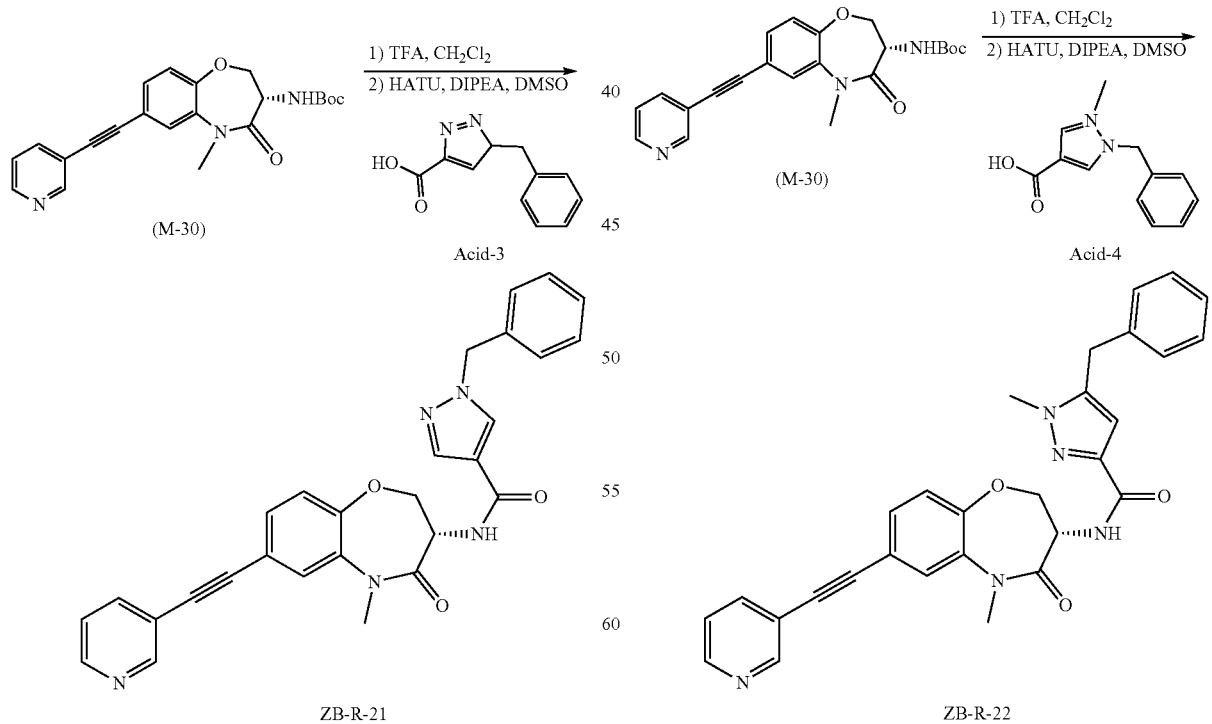

M-30 (25 mg) was dissolved in 2 mL of dichloromethane and 1 mL of trifluoroacetic acid, reacted for 1 h, and M-30 (25 mg) was dissolved in 2 mL of dichloromethane and 1 mL of trifluoroacetic acid, reacted for 1 h, and rotary-dried to remove the solvent to obtain an intermediate amine. The intermediate was dissolved in DMSO (1 mL), added with 35 mg of acid-4 (the acid was purchased commercially, or for the preparation of the acid please refer to CN105121432A and *J. Med Chem.* 2017, 60, 1247), HATU (56 mg) and DIPEA (60 mg), reacted overnight, and added with water and ethyl acetate to extract. The organic layer was collected, dried over anhydrous sodium sulfate, rotary-evaporated under vacuum to remove the solvent, and separated by HPLC to obtain the compound ZB-R-22. HPLC-MS: [M+H]$^+$=492.2.

Example 50

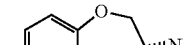

M-30 (25 mg) was dissolved in 2 mL of dichloromethane and 1 mL of trifluoroacetic acid, reacted for 1 h, and rotary-dried to remove the solvent to obtain an intermediate amine. The intermediate was dissolved in DMSO (1 mL), added with 35 mg of acid-5 (the acid was purchased commercially, or for the preparation of the acid please refer to CN105121432A and *J. Med Chem.* 2017, 60, 1247), HATU (56 mg) and DIPEA (60 mg), reacted overnight, and added with water and ethyl acetate to extract. The organic layer was collected, dried over anhydrous sodium sulfate, rotary-evaporated under vacuum to remove the solvent, and separated by HPLC to obtain the compound ZB-R-23. HPLC-MS: [M+H]$^+$=479.2.

Example 51

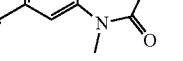

M-30 (25 mg) was dissolved in 2 mL of dichloromethane and 1 mL of trifluoroacetic acid, reacted for 1 h, and rotary-dried to remove the solvent to obtain an intermediate amine. The intermediate was dissolved in DMSO (1 mL), added with 35 mg of acid-6 (the acid was purchased commercially, or for the preparation of the acid please refer to CN 105121432A and *J. Med Chem.* 2017, 60, 1247), HATU (56 mg) and DIPEA (60 mg), reacted overnight, and added with water and ethyl acetate to extract. The organic layer was collected, dried over anhydrous sodium sulfate, rotary-evaporated under vacuum to remove the solvent, and separated by HPLC to obtain the compound ZB-R-24. HPLC-MS: [M+H]$^+$=479.2.

Example 52

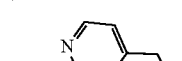

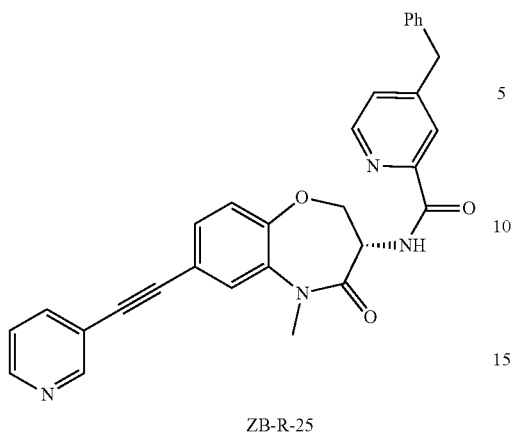

ZB-R-25

M-30 (25 mg) was dissolved in 2 mL of dichloromethane and 1 mL of trifluoroacetic acid, reacted for 1 h, and rotary-dried to remove the solvent to obtain the intermediate amine. The intermediate was dissolved in DMSO (1 mL), added with 35 mg of Acid-7 (the acid was purchased commercially, or for the preparation of the acid please refer to CN105121432A and *J. Med Chem.* 2017, 60, 1247), HATU (56 mg) and DIPEA (60 mg), reacted overnight, and added with water and ethyl acetate to extract. The organic layer was collected, dried over anhydrous sodium sulfate, rotary-evaporated under vacuum to remove the solvent, and separated by HPLC to obtain the compound ZB-R-25. HPLC-MS: [M+H]$^+$=489.1.

Example 53

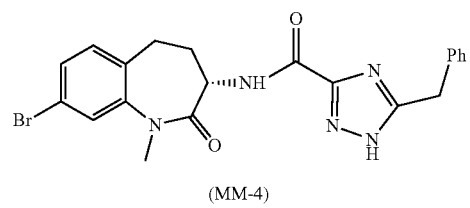

(MM-4)

Step One:

50 mg of MM-1 (for the synthesis of MM-1 please refer to WO2014125444) was dissolved in 3 mL of DMF, added with 30 mg of potassium carbonate and 24 mg of methyl iodide, reacted for 3 h, and added with 15 ml of water to precipitate a large amount of solid, which was filtered and dried to obtain the intermediate MM-2.

Step Two:

40 mg of MM-2 was dissolved in 3 mL of methylene chloride, added with 1 ml of trifluoroacetic acid, reacted for 30 min, and rotary-dried to remove the solvent to obtain the intermediate MM-3, which was directly used for the next step without purification.

Step Three:

MM-3 obtained in the previous step was added with DMSO (1 mL), and then with 20 mg of acid-1 (for the preparation of the acid please refer to CN 105121432A and *J. Med Chem.* 2017, 60, 1247), HATU (62 mg) and DIPEA (60 mg), reacted overnight, and added with water and ethyl acetate to extract. The organic layer was collected, dried over anhydrous sodium sulfate, and separated by column chromatography to obtain MM-4. HPLC-MS: [M+H]$^+$=454.1.

Example 54

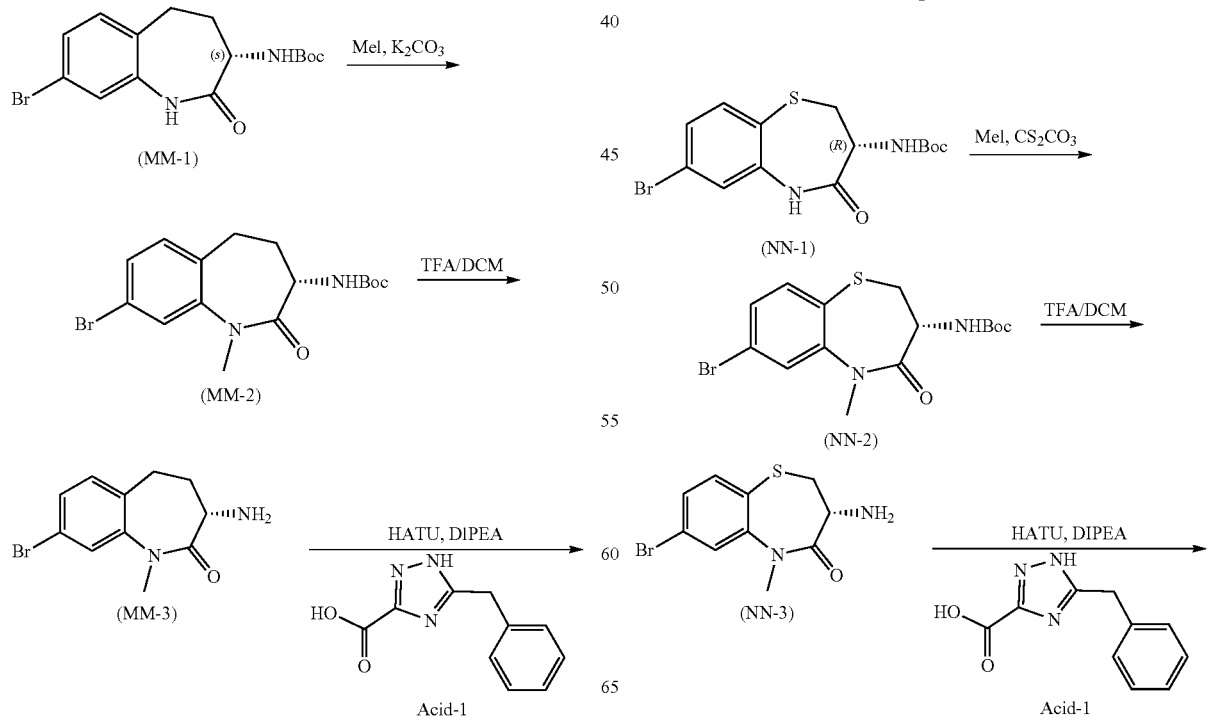

-continued

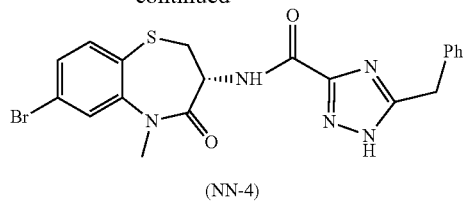

(NN-4)

Step One:

50 mg of NN-1 (for the synthesis of NN-1 please refer to WO2014125444) was dissolved in 3 mL of DMF, added with 30 mg of cesium carbonate and 24 mg of methyl iodide, reacted for 3 h, and added with 15 mL of water to precipitate a large amount of solid, which was filtered and dried to obtain the intermediate NN-2.

Step Two:

40 mg of NN-2 was dissolved in 3 mL of methylene chloride, added with 1 ml of trifluoroacetic acid, reacted for 30 min, and rotary-dried to remove the solvent to obtain the intermediate NN-3, which was directly used for the next step without purification.

Step Three:

NN-3 obtained in the previous step was added with DMSO (1 mL), and then with 20 mg of acid-1 (for the preparation of the acid please refer to CN105121432A and *J. Med Chem.* 2017, 60, 1247), HATU (62 mg) and DIPEA (60 mg), reacted overnight, and added with water and ethyl acetate to extract. The organic layer was collected, dried over anhydrous sodium sulfate, and separated by column chromatography to obtain NN-4. HPLC-MS: [M+H]$^+$=472.1.

Example 55

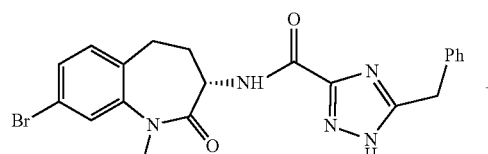

(MM-4)

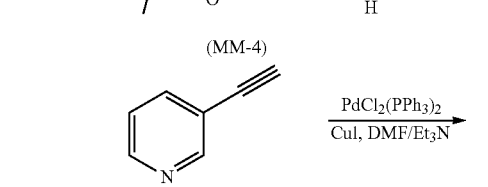

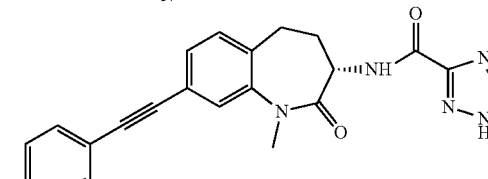

ZB-R-26

MM-4 (25 mg), 3-ethynylpyridine (10 mg), PdCl$_2$(PPh$_3$)$_2$ (CAS: 13965-03-2, 4.6 mg) and cuprous iodide (2.5 mg) were dissolved in 2 mL of N,N-dimethylformamide (DMF) and 1 mL of triethylamine, heated to 85° C. under argon, reacted for 3 h, cooled to room temperature, rotary evaporated under vacuum to remove the solvent, and separated by HPLC to obtain the compound ZB-R-26. HPLC-MS: [M+H]$^+$=477.2.

Example 56

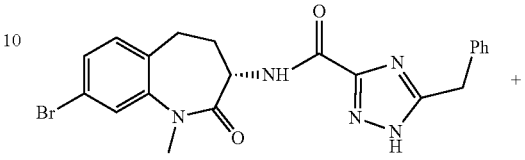

(MM-4)

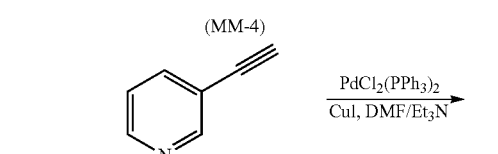

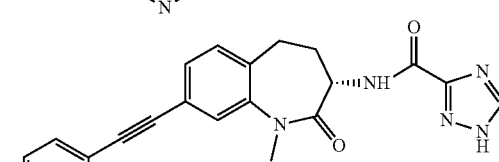

ZB-R-27

MM-4 (25 mg), 2-ethynylpyridine (10 mg), PdCl$_2$(PPh$_3$)$_2$ (CAS: 13965-03-2, 4.6 mg) and cuprous iodide (2.5 mg) were dissolved in 2 mL of N,N-dimethylformamide (DMF) and 1 mL of triethylamine, heated to 85° C. under argon, reacted for 3 h, cooled to room temperature, rotary evaporated under vacuum to remove the solvent, and separated by HPLC to obtain the compound ZB-R-27. HPLC-MS: [M+H]$^+$=477.2.

Example 57

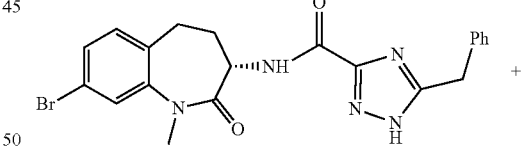

(MM-4)

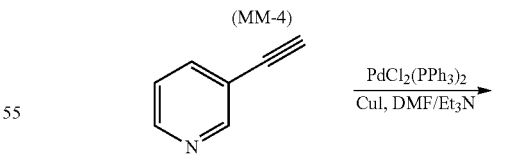

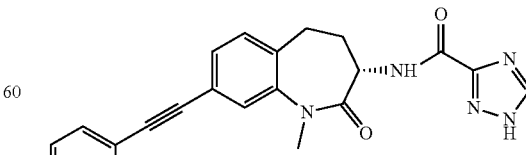

ZB-R-28

MM-4 (25 mg), 4-ethynylpyridine (10 mg), PdCl$_2$(PPh$_3$)$_2$ (CAS: 13965-03-2, 4.6 mg) and cuprous iodide (2.5 mg) were dissolved in 2 mL of N,N-dimethylformamide (DMF) and 1 mL of triethylamine, heated to 85° C. under argon, reacted for 3 h, cooled to room temperature, rotary evaporated under vacuum to remove the solvent, and separated by HPLC to obtain the compound ZB-R-28. HPLC-MS: [M+H]$^+$=477.2.

Example 58

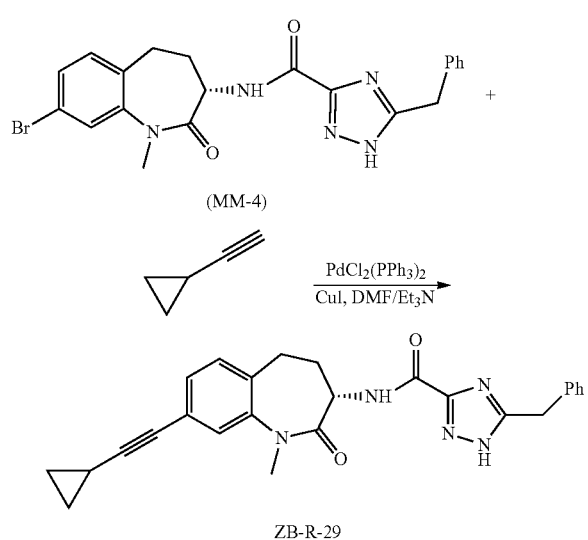

ZB-R-29

MM-4 (25 mg), cyclopropylacetylene (10 mg), PdCl$_2$(PPh$_3$)$_2$, (CAS: 13965-03-2, 4.6 mg) and cuprous iodide (2.5 mg) were dissolved in 2 mL of N,N-dimethylformamide (DMF) and 1 mL of triethylamine, heated to 85° C. under argon, reacted for 3 h, cooled to room temperature, rotary evaporated under vacuum to remove the solvent, and separated by HPLC to obtain the compound ZB-R-29. HPLC-MS: [M+H]$^+$=440.2.

Example 59

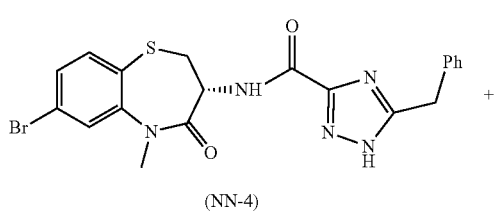

(NN-4)

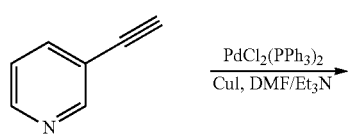

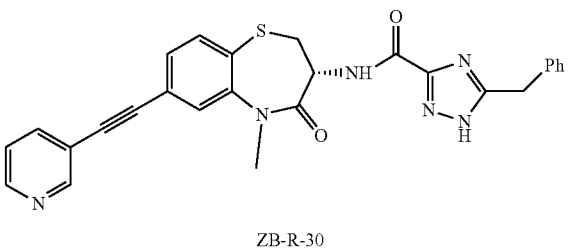

ZB-R-30

NN-4 (25 mg), 3-ethynylpyridine (10 mg), PdCl$_2$(PPh$_3$)$_2$ (CAS: 13965-03-2, 4.6 mg) and cuprous iodide (2.5 mg) were dissolved in 2 mL of N,N-dimethylformamide (DMF) and 1 mL of triethylamine, heated to 85° C. under argon, reacted for 3 h, cooled to room temperature, rotary evaporated under vacuum to remove the solvent, and separated by HPLC to obtain the compound ZB-R-30. HPLC-MS: [M+H]$^+$=495.2.

Example 60

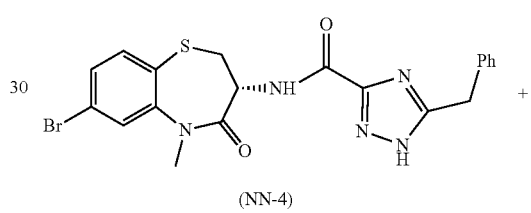

(NN-4)

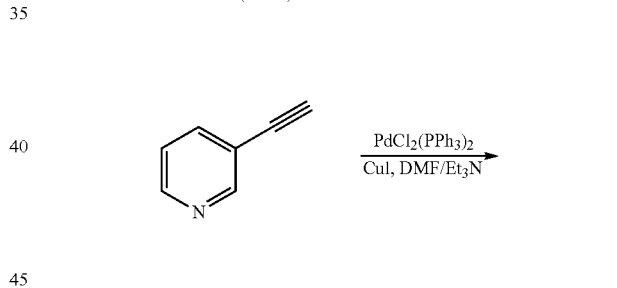

ZB-R-31

NN-4 (25 mg), 2-ethynylpyridine (10 mg), PdCl$_2$(PPh$_3$)$_2$ (CAS: 13965-03-2, 4.6 mg) and cuprous iodide (2.5 mg) were dissolved in 2 mL of N,N-dimethylformamide (DMF) and 1 mL of triethylamine, heated to 85° C. under argon, reacted for 3 h, cooled to room temperature, rotary evaporated under vacuum to remove the solvent, and separated by HPLC to obtain the compound ZB-R-31. HPLC-MS: [M+H]$^+$=495.2.

Example 61

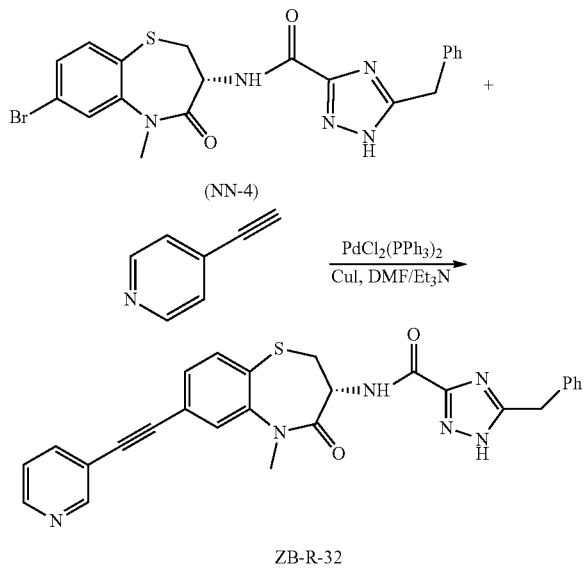

NN-4 (25 mg), 4-ethynylpyridine (10 mg), PdCl$_2$(PPh$_3$)$_2$, (CAS: 13965-03-2, 4.6 mg) and cuprous iodide (2.5 mg) were dissolved in 2 mL of N,N-dimethylformamide (DMF) and 1 mL of triethylamine, heated to 85° C. under argon, reacted for 3 h, cooled to room temperature, rotary evaporated under vacuum to remove the solvent, and separated by HPLC to obtain the compound ZB-R-32. HPLC-MS: [M+H]$^+$=495.2.

Example 62

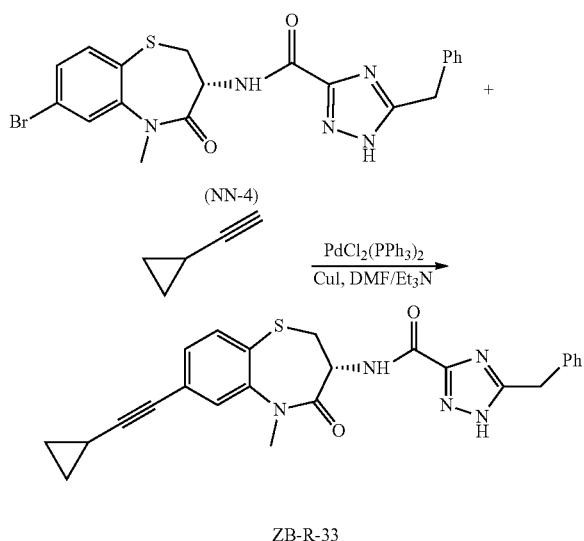

NN-4 (25 mg), cyclopropylacetylene (10 mg), PdCl$_2$(PPh$_3$)$_2$ (CAS: 13965-03-2, 4.6 mg) and cuprous iodide (2.5 mg) were dissolved in 2 mL of N,N-dimethylformamide (DMF) and 1 mL of triethylamine, heated to 85° C. under argon, reacted for 3 h, cooled to room temperature, rotary evaporated under vacuum to remove the solvent, and separated by HPLC to obtain the compound ZB-R-33. HPLC-MS: [M+H]$^+$=458.2.

Example 63: Cell Viability Test (TNFα Induced U937 Cell Programmed Necroptosis System)

1. Cell culture:
U937 cells were cultured in a 37° C., 5% CO$_2$ saturated humidity incubator using RPM 1-1640 culture medium (containing 100 U/mL penicillin and 0.1 g/L streptomycin) containing 10% fetal bovine serum, and the medium was exchanged 3-4 times a week for passage.

2. Experimental instruments: electronic balance (Mettler Toledo METTLER TOLEDO (AL104)), water bath (Shanghai Jinghong Experimental Equipment Co., Ltd., DKZ-2), upright microscope (Leica Microsystems, Germany), biological safety cabinet (Heal Force HF Safe-1500), 4° C. refrigerator (U.S. Haier HYC360), −30° C. refrigerator (Japan Panasonic mdf-u539-pc), −80° C. refrigerator (U.S. thereto fisher scientific 906-ULTS), incubator (Forma 311 Thermo Forma), pure water system (U.S. Millipore company), flow cytometer (BDFACS Calibur), microplate reader (U.S. PE Envision).

3. Experimental reagents: RPMI-1640 medium, RPMI-1640 medium (no phenol red), CellTiter-Glo® Luminescent Cell Viability Assay (promega, G7572), Human TNFα (Peprotech, 300-01 A), Q-VD-Oph (Selleck, S7311), FITC Annexin V Apoptosis Detection Kit (BD, 556547), Reactive Oxygen Species Assay Kit (Beyotime, S0033).

4. Experimental protocol: TNFα induced U937 cell programmed necroptosis system was used to screen for compounds with RIP 1 kinase inhibitory activity.
  1) U937 cells were collected to prepare a single cell suspension and count.
  2) The cells were seeded in a 96-well plate with 5*10$^6$ cells/well.
  3) Dissolving the compound: the compound was dissolved in dimethyl sulfoxide (DMSO) to prepare a 5 mM stock solution.
  4) Diluting the compound: starting from 50 nM, the compound was successively diluted by 2.5 times, with 7 concentration gradients.
  5) Setting Cell control wells (Control) and stimulation control wells (programmed necroptosis induced by TNFα combined with QVD), the other wells were added with the test compounds having different concentrations to co-incubate with 25 µM Q-VD-Oph for 30 min, and then added with 100 ng/mL of TNFα for stimulation, and cultivated for 24 h.
  6) After incubation, 100 µl of CellTiter-Glo® Luminescent reagent was added, shaked for 2 min, and then the fluorescence value was read on a microplate reader.

5. Inhibition assay of compounds: the fluorescence value reflects the number of living cells per well. Inhibition= (fluorescence value of test compound sample−fluorescence value of TNFα stimulated sample) % (fluorescence value of control well (Control)−fluorescence value of TNFα stimulated sample)*100, and then IC$_{50}$ was fitted.

GSK2982772 as the positive compound is currently in phase II clinical trials (J. Med. Chem. 2017, 60, 1247-1261).

TABLE 1

| Compound | RIP1 IC$_{50}$(nM) |
| --- | --- |
| GSK2982772 | 2.30 |
| ZB-R-39 | 0.17 |

TABLE 1-continued

| Compound | RIP1 IC$_{50}$(nM) |
|---|---|
| ZB-R-42 | 0.32 |
| ZB-R-44 | 4.08 |
| ZB-R-45 | 8.13 |
| ZB-R-46 | 5.39 |
| ZB-R-47 | 0.39 |
| ZB-R-50 | 0.26 |
| ZB-R-51 | <0.5 |
| ZB-R-52 | 0.42 |
| ZB-R-53 | 0.11 |
| ZB-R-54 | 0.10 |
| ZB-R-55 | <0.5 |
| ZB-R-68 | 0.2 |
| ZB-R-76 | 0.54 |
| ZB-R-78 | 0.35 |
| ZB-R-80 | 0.31 |
| ZB-R-81 | 0.29 |
| ZB-R-82 | 0.30 |
| ZB-R-84 | 0.19 |
| ZB-R-85 | 1.09 |
| ZB-R-87 | 0.2 |
| ZB-R-89 | 1.7 |
| ZB-R-20 | <0.5 |
| ZB-R-24 | <1 |
| ZB-R-25 | <2 |

From the results in Table 1 above, it can be seen that the cell activities of some compounds are significantly stronger than the positive compound GSK2982772, and the cell activities of several compounds are ten times stronger than that of the positive compound GSK2982772.

Example 64

TNFα Induced C57BL/6 Mouse Systemic Inflammatory Response Syndrome (SIRS) Model

1. Experimental Animals:

Source, stirp and strain: C57BL/6 pure mouse, female, 18-20 g, purchased from Shanghai Lingchang Biotechnology Co., Ltd., license No. SCXK (Shanghai) 2013-0018. The animals were bred in the SPF animal room of Building No. 2 of the Shanghai institute of Materia Medica, and the experimental animal use license number is SYXK (Shanghai) 2013-0049. The animals were bred for at least one week before use at 22±1° C. with a humidity of 55±5% and 12 h light and dark cycle. Both feed and water are freely ingested by the animals after disinfection. All experiments were carried out in strict accordance with the relevant regulations on experimental animals.

2. Test Reagents and Materials:
1) Recombinant Mouse mTNFα was purchased from Shanghai JIN'AN Biological Company.
2) Experimental materials: 1.5 mL centrifuge tubes were purchased from Axygen Company, 15 mL and 50 mL centrifuge tubes were purchased from Corning Company; commonly used surgical instruments (ophthalmic scissors, large tweezers, small tweezers, tissue scissors) and 1 mL, 2 mL, and 10 mL disposable plastic dispensers were purchased from Sinopharm Chemical Reagent Co., Ltd.; pipettes of various specifications were purchased from Eppendorf Company; tips of various specifications were purchased from Axygen and Sartoruris Company.
3) Experimental equipments: the syringe adopts omnican insulin syringes, a disposable syringe adopts sterile insulin syringe with a product number of 9161635, and an outer diameter and length of the needle tube of 0.30*8 mm; the mouse tail vein syringe is model YLS-Q9G purchased from Jinan Yyan Technology Development Co., Ltd.; Laboratory animal rectal temperature measuring instrument was model ALC-ET06 purchased from Shanghai Alcott Biotechnology Co., Ltd.

3. Reagents and Compound Preparation Methods:
1) Recombinant Mouse mTNFα: mTNFα lyophilized powder was dissolved in PBS to prepare a stock solution of 200 µg/mL, and stored in a refrigerator at −20° C. after sub-packaging. The stock solution was put in a refrigerator at 4° C. overnight to reach dissolution equilibrium when in use. On the day of modeling, the stock solution was diluted 5-folds with PBS to 40 µg/mL, and gently shaken to mix well.
2) Compound preparation: Both the positive control drug and the test compound were suspended in 0.2% HPMC, and sonicated to form a uniform suspension. The drug concentration was determined comprehensively according to the results of in vitro experiments and the pharmacokinetic properties.

4. Experimental Scheme:
1) Model introduction: This model was injected with TNFα through the tail vein, causing systemic inflammation in mice accompanied with hypothermic shock. The RIP1 protein, which is the research object of the project, is a downstream protein of the TNF receptor and plays a key role in the inflammatory response. Therefore, the model with tail vein injection of TNFα was selected as the classic model for an animal level screen of RIP1 inhibitor.
2) Experimental process:
a) The experimental animals were randomly grouped according to their body weight one day in advance, and there are 8 animals in each group.
b) On the day of the experiment, mTNFα and sterile PBS were diluted according to the above method, sucked into an insulin syringe at 125 µl/piece, that is, 5 µg/mice.
c) The drug was administered 15 min before modeling by gavage at 0.2 mL/mouse.
d) 15 min after administration, the modeling was started by injection of PBS or mTNFα into the tail vein, the injection was conducted according to the above dose.
e) After modeling, the rectal temperature was measured every 1 h and the survival rate was measured.

5. Testing Indicators:
1) Animal body temperature: The rectal temperature was measured every 1 h after modeling. The protective effect of the compound from decrease in body temperature can reflect its RIPK1 inhibitory activity.
2) Mortality: Animals will die when their body temperature drops below 26° C. The detection of mortality is also an indicator to evaluate the protective effect of the compound on the animal's hypothermic shock response.

Among them, GSK2982772 is a positive compound (J. Med. Chem. 2017, 60, 1247-1261).

The experimental results of the body temperature and the mortality of the above animals for ZB-R-53, ZB-R-54, ZB-R-55, ZB-R-50 and the positive control compound GSK2982772 is shown in FIGS. 1-4 and the following Table 2.

As shown in FIGS. 1-4, the compounds ZB-R-53, ZB-R-54, ZB-R-55 and ZB-R-50 of the present application can exhibit a better effect of body temperature protection than the positive control compound GSK2982772 in hypothermic shock models, that is, the degree of body temperature drop is lower.

TABLE 2

| Mice type | Survival rate |
|---|---|
| Normal mice | 100% |
| Non-administered model mice | 50% |
| GSK2982772 treated mice | 100% |
| ZB-R-53 treated mice | 100% |
| ZB-R-54 treated mice | 100% |
| ZB-R-55 treated mice | 100% |
| ZB-R-50 treated mice | 100% |

As shown in Table 2, the survival rate of mice administered with the compound of the present application in the hypothermic shock model was 100%.

Therefore, the compound of the present application not only exhibits effective anti-systemic inflammatory response syndrome activity (relative to the blank control, that is, vehicle), but also exhibits better activity than the positive control compound.

Example 65

Study on Oral Pharmacokinetics in Rats

1. Healthy male SD rats were used as test animals, ZB-R-39, ZB-R-50, ZB-R-51, ZB-R-52, ZB-R-53, ZB-R-54 and ZB-R-55 (3 mg/kg) were administered by gavage, and the drug plasma concentrations in rat at different time points after administration were determined by using LC/MS/MS method. The pharmacokinetic behaviors of the compounds of the present invention in rats were studied, and the pharmacokinetic properties of the compounds were evaluated.
2. The test animals are healthy adult male SD rats, 3 in each group.
3. Pharmaceutical preparation: The compounds ZB-R-39, ZB-R-50, ZB-R-51, ZB-R-52, ZB-R-53, ZB-R-54, ZB-R-55 were prepared by dissolving them separately in DMSO/0.5% HPMC (5/95, v/v), vortexing, and sonicating to disperse the solid matter evenly, so as to obtain a pale white suspension.
4. Operation: ZB-R-39, ZB-R-50, ZB-R-51, ZB-R-52, ZB-R-53, ZB-R-54 and ZB-R-55 were administered to the rats by gavage (3 mg/kg), respectively, and after 0.25, 0.5, 1, 2, 4, 8 and 24 h of administration, 45 μL of the blood was taken through the femoral vein, put in heparinized centrifuge tubes and centrifuged for 5 min to separate plasma for sample analysis. Liquid chromatography tandem mass spectrometry (LC-MS/MS) was used to determine the plasma concentration of test compounds in rat after intragastrical administration of different compounds.

The pharmacokinetic parameters of the compounds of the present invention are shown in Table 3 below:

TABLE 3

| Compound | | Half life T1/2 (h) | Peak plasma concentration $C_{max}$ (ng/mL) | $AUC_{last}$ (h*ng/mL) | $AUC_{INF\_obs}$ (h*ng/mL) | Average residence time $MRT_{INF\_obs}$ (h) |
|---|---|---|---|---|---|---|
| ZB-R-39 | Average | 3.46 | 525 | 1677 | 1701 | 4.07 |
| | SD | 1.13 | 11 | 252 | 220 | 1.06 |
| ZB-R-50 | Average | 1.56 | 1452 | 3110 | 3116 | 2.20 |
| | SD | 1.28 | 861 | 1069 | 1074 | 0.69 |
| ZB-R-51 | Average | 1.79 | 1363 | 4208 | 4292 | 2.80 |
| | SD | 0.74 | 339 | 773 | 693 | 0.56 |
| ZB-R-52 | Average | 0.81 | 755 | 1557 | 1559 | 1.61 |
| | SD | 0.05 | 107 | 203 | 203 | 0.08 |
| ZB-R-53 | Average | 1.54 | 1757 | 4499 | 4654 | 2.41 |
| | SD | 0.11 | 179 | 476 | 451 | 0.16 |
| ZB-R-54 | Average | 1.14 | 667 | 1239 | 1250 | 2.00 |
| | SD | 0.25 | 529 | 598 | 592 | 0.58 |
| ZB-R-55 | Average | 3.71 | 2895 | 25712 | 26092 | 7.23 |
| | SD | 0.23 | 761 | 4767 | 4775 | 0.60 |

$AUC_{last}$: the AUC of the period from the administration time to the last time point
$AUC_{INF\_obs}$: the AUC of the period from the administration time to the time point of the theoretical extrapolate to infinity As shown in Table 3, the compound of the present invention has good pharmacokinetic absorption and has obvious pharmacokinetic advantages.

Example 66

[I]. The Establishment of DSS-Induced Ulcerative Colitis Mouse Model and Pharmacodynamic Evaluation 1. Female C57BL/6 mice were randomly divided into normal control group, model group, GSK2982772 (GSK) treated group, and ZB-R-51 and ZB-R-52 (10 mg/kg) (having a RIP1 inhibitory activity effect) treated Groups, 6 mice in each group. Except for the mice in the normal control group, 3% DSS was added to the drinking water of the mice in the other groups, including the model group and the compound-treated group for 8 consecutive days, to induce the intestinal inflammation model.
2. From the day when the mice were induced and modeled to the end of the experiment, the treatment groups were respectively given GSK2982772 or the compounds ZB-R-51 or ZB-R-52 (10 mg/kg) by gavage for therapeutic intervention.
3. Evaluation of disease activity index During the experiment, each group of mice was weighed every day, and detected fecal occult blood, and the disease activity of each mouse was scored according to Table 4 below.

TABLE 4

Disease Activity Index (DAI) score sheet

| Weight loss (%) | Fecal form | Fecal occult blood | score |
|---|---|---|---|
| 0 | Normal | Negative | 0 |
| 1~5 | / | + | 1 |
| 5~10 | Soft Fecal | ++ | 2 |
| 10~20 | / | +++ | 3 |
| >20 | Loose Fecal | Perianal bleeding | 4 |

Table 4. Weight loss is divided into 5 levels (0, no weight loss or increase; 1, a decrease of 1-5%; 2, a decrease of 5-10%; 3, a decrease of 10-20%; 4, a decrease of more than 20%); fecal hardness is divided into 3 levels (0, normal; 2, soft fecal; 4, loose fecal); fecal occult blood is divided into 5 levels (0, negative; 1, +; 2, ++; 3, +++; 4, perianal bleeding).

FIGS. 5 to 8 show the graphs of body weight and the disease activity index versus time of normal mice, blank control group, control group, and mice administered with the compound of the present invention. It can be seen from FIGS. 5 to 8 that the administration of the active compounds ZB-R-51 and ZB-R-52 of the present invention by intragastric administration can significantly improve the disease symptoms of DSS-induced inflammatory bowel disease in mice, and improve the clinical symptoms of weight loss, diarrhea, hematochezia etc.

[II]. The Overall and Microscopic Pathological Changes of Mouse Colon Tissue

At the end of the experiment, mouse colon tissue was taken to measure its length. The distal colon was cut and fixed in formalin, paraffin-embedded and H&E stained to make pathological sections.

Figure 9:
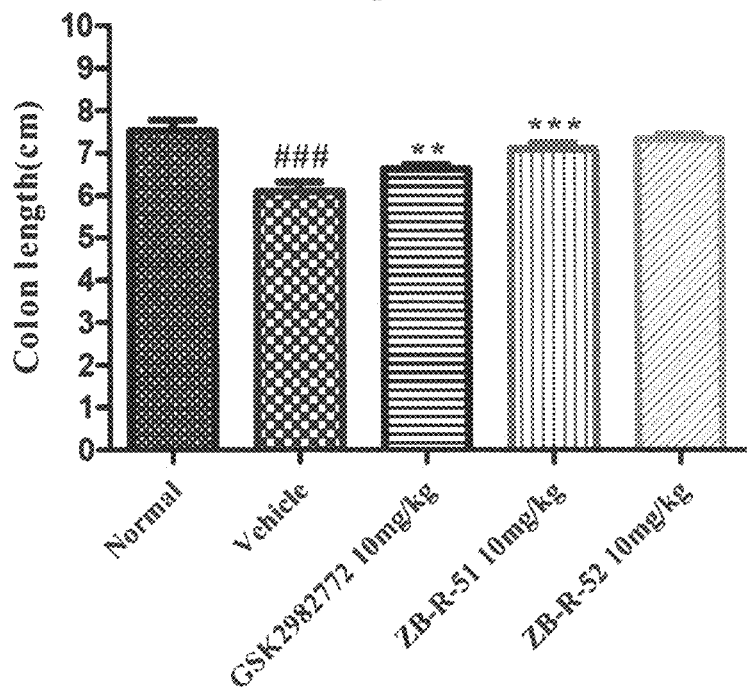
FIG. 9 is a graph of comparing colon lengths of normal mice, blank control group, positive control group administered with GSK, and mice administered with the compound ZB-R-52 of the present application at the end of the experiment.
Figure 10:
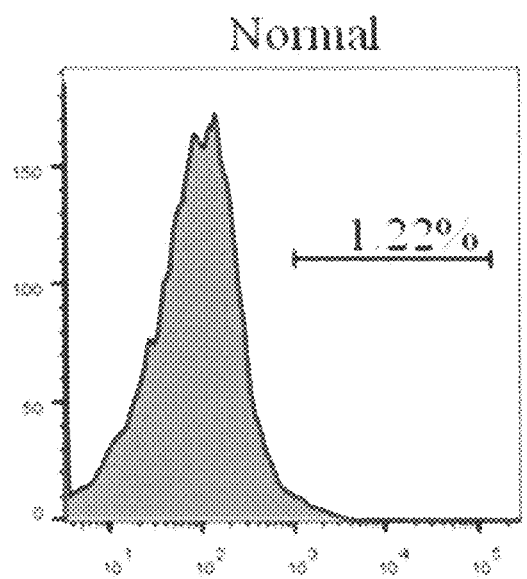
FIGS. 10-14 are respectively the graphs showing the UC mouse spleen T cell activation of the normal mice, blank control group, positive control group administered with GSK, mice administered with the compound ZB-R-51 of the present application, and mice administered with the compound ZB-R-52 of the present application.
Figure 11:
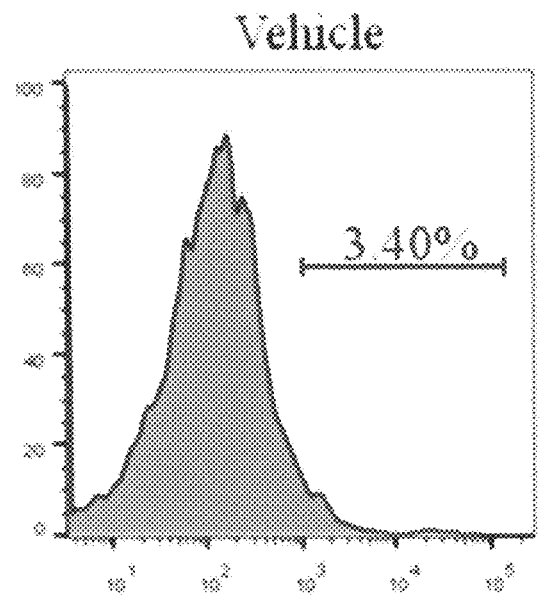
Figure 12:
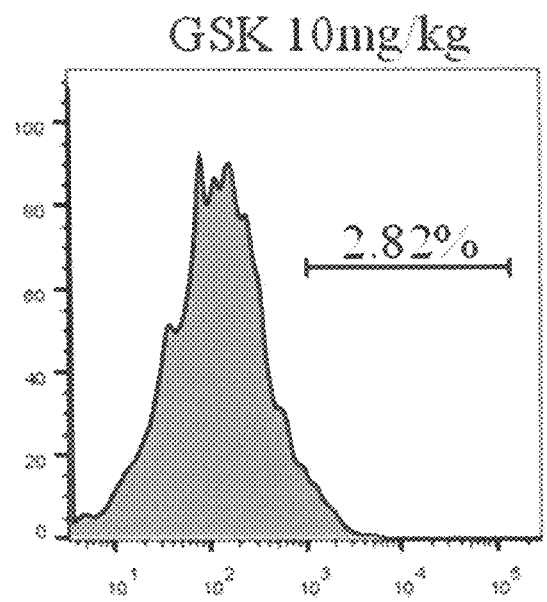
Figure 13:
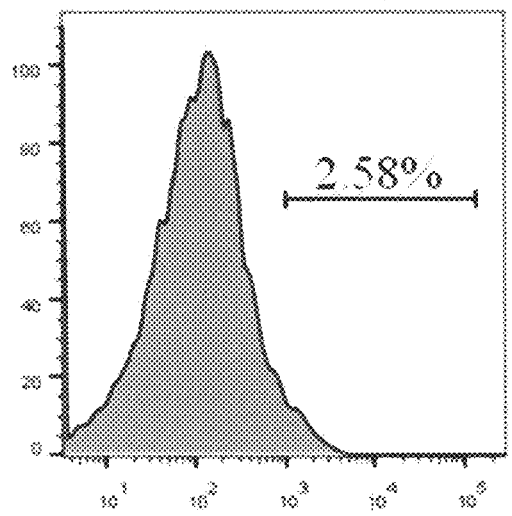
Figure 14:
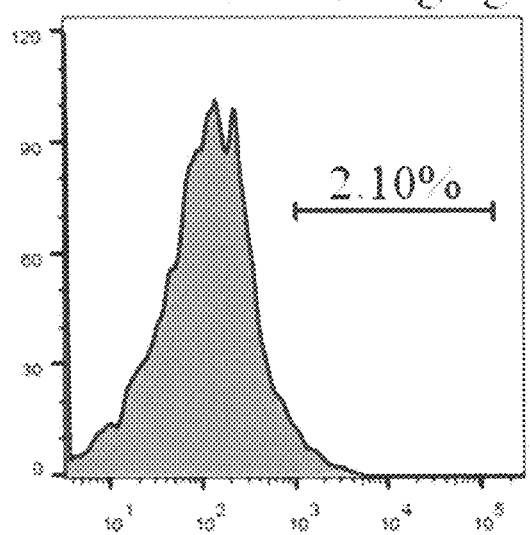
Figure 15:
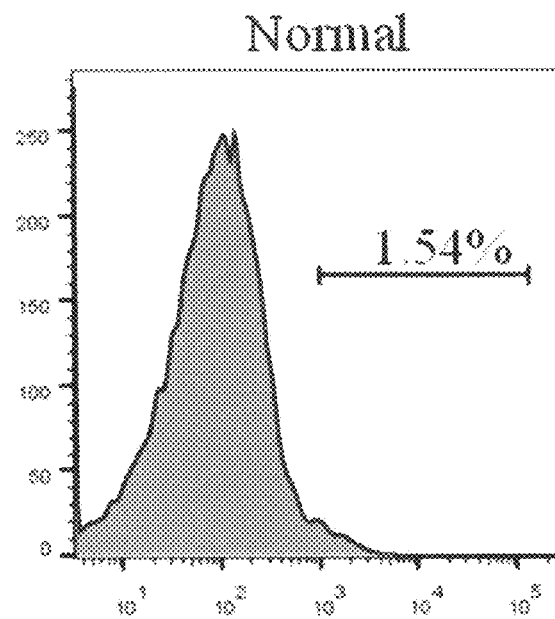
FIGS. 15-19 are respectively the graphs showing the UC mouse mesenteric lymph node T cell activation of the normal mice, blank control group, positive control group administered with GSK, mice administered with the compound ZB-R-51 of the present application, and mice administered with the compound ZB-R-52 of the present application.
Figure 16:
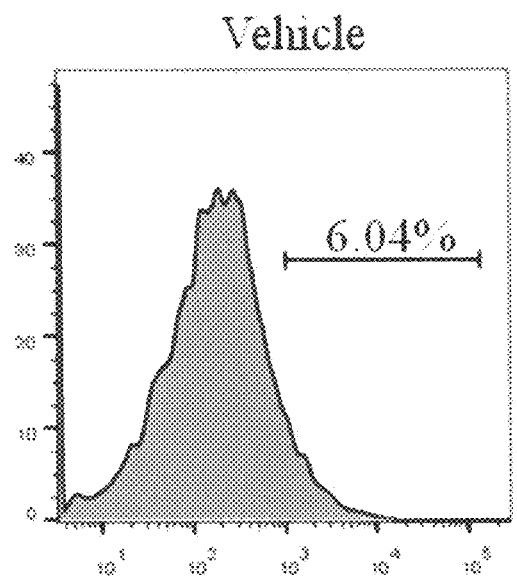
Figure 17:
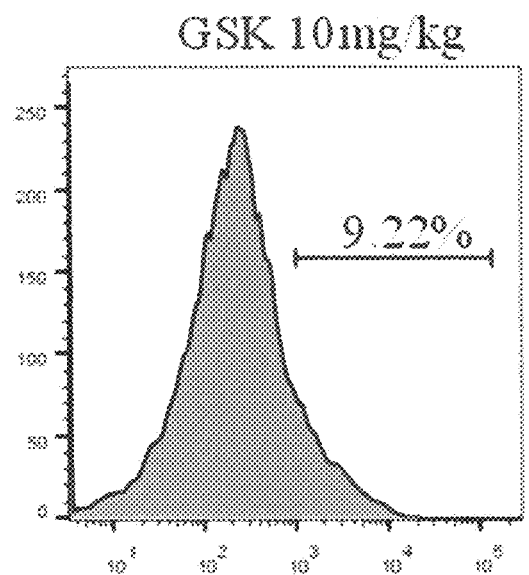
Figure 18:
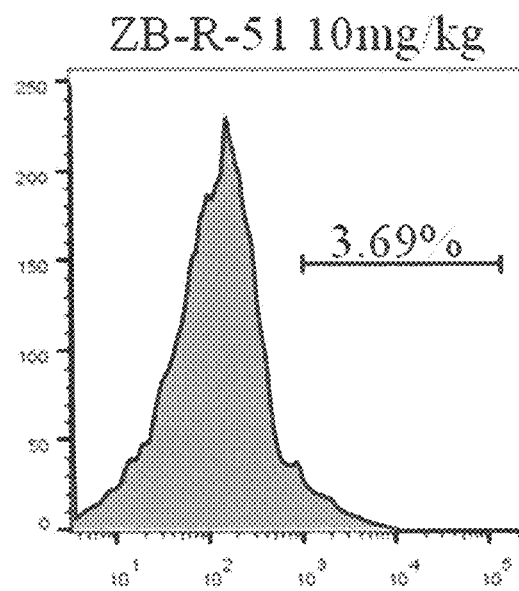
Figure 19:
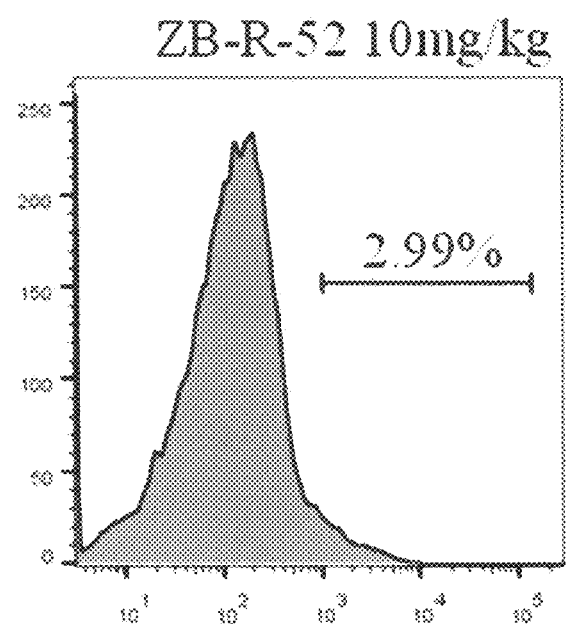

FIG. 9 is a graph of comparing colon lengths at the end of the experiment of normal mice, blank control group, positive control group administered with GSK, and mice administered with ZB-R-51 and ZB-R-52 of the present application.

FIGS. 10-14 are the graphs showing the UC mouse spleen T cell activation of the normal mice, blank control group, positive control group administered with GSK, mice administered with ZB-R-51 of the present application, and mice administered with ZB-R-52 of the present application.

S FIGS. 15-19 are the graphs showing the UC mouse mesenteric lymph node T cell activation of the normal mice, blank control group, positive control group administered with GSK, mice administered with ZB-R-51 of the present application, and mice administered with ZB-R-52 of the present application.

It can be seen from FIG. 9 that the treatment with the compounds ZB-R-51 and ZB-R-52 of the present invention can significantly inhibit the shortening of colon length caused by DSS-induced inflammation.

From FIG. 10 to FIG. 19, it can be seen that the compounds ZB-R-51 and ZB-R-52 are significantly better than the positive compound GSK2982772 (GSK) in the multiple evaluated indicators.

Therefore, the experimental results of the above-mentioned representative compounds ZB-R-51 and ZB-R-52 in a mouse model of inflammatory bowel disease induced by dextran sulfate (DSS) show that the compounds of the present invention by intragastric administration can effectively improve the clinical symptoms of colitis, such as weight loss, diarrhea and hematochezia of the experiment animals, reduce the pathological damage of colon tissue, and pharmacological studies have confirmed that this type of compounds has good anti-inflammatory and immunosuppressive activity and high safety, and has good application prospects in clinical treatment and adjuvant treatment of inflammatory bowel disease.

The invention claimed is:

1. A compound of formula I, or a pharmaceutically acceptable salt, stereoisomer, enantiomer, diastereomer, atropisomer, optical isomer, racemate, polymorph, solvate or isotopically labeled compound thereof:

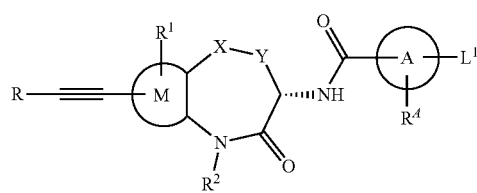

Formula I wherein
X is S, SO,

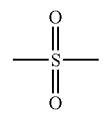

Y is $C_1$-$C_2$ alkylene;
Ring A is a benzene ring, a 5-6 membered heteroaromatic ring, a 5-6 membered non-aromatic heterocyclic ring or

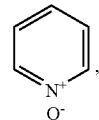

and the carbonyl moiety and $L^1$ connected to Ring A are in meta-positions;
$R^A$ is H or $C_1$-$C_4$ alkyl;
$L^1$ is $C_3$-$C_6$ alkyl, $C_3$-$C_6$ alkoxy, halogenated $C_3$-$C_6$ alkoxy, $C_3$-$C_6$ alkenyl, $C_3$-$C_6$ alkenyloxy, or

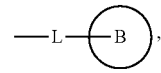

wherein
L is O, S, NH, N(CH$_3$), CH$_2$, CH$_2$CH$_2$, CH(CH$_3$), CHF, CF$_2$, CH$_2$O, CH$_2$N(CH$_3$), CH$_2$NH or CH(OH);
Ring B is a $C_3$-$C_6$ cycloalkyl, phenyl, 5-6 membered heteroaryl or 5-6 membered non-aromatic heterocyclyl, wherein the $C_3$-$C_6$ cycloalkyl, the phenyl, the 5-6 membered heteroaryl and the 5-6 membered non-aromatic heterocyclyl are each independently unsubstituted or substituted with one or two substituents each independently selected from the group consisting of halogen, $C_1$-$C_4$ alkyl, halogenated $C_1$-$C_4$ alkyl, $C_1$-$C_4$ alkoxy, halogenated $C_1$-$C_4$ alkoxy, nitro and $C_1$-$C_4$ alkyl C(O)—;
$R^2$ is H or CH$_3$;
Ring M is independently a $C_6$-$C_{10}$ aromatic ring or a 5-10 membered heteroaromatic ring;
$R^1$ representative 1-3 substituents each independently being H, halogen, —OH, —CN, —COOH, Ct-Co alkyl, $C_1$-$C_6$ haloalkyl, $C_1$-$C_6$ alkoxy, $C_1$-$C_6$ haloalkoxy, $C_2$-$C_{10}$ alkoxyalkyl, $C_2$-$C_{10}$ haloalkoxyalkyl, $C_1$-$C_6$ hydroxyalkyl, —B(OH)$_2$, —S(O)$_{n1}$R$^a$, —N(R$^a$)$_2$, —C(═O)N(R$^a$)$_2$, —NHC(═O)R$^a$, —NHC(═O)OR$^a$, —NHC(═O)C(═O)N(R$^1$)$_2$, —NHC(═O)C(═O)OR$^a$, —NHC(═O)N(R$^a$)$_2$, —NHC(═O)

NR$^a$C(=O)N(R$^a$)$_2$, —NHC(=O)NR$^a$S(O)$_2$OR$^a$, —NHC(=O)NR$^a$S(O)$_2$N(R$^a$)$_2$, —NHC(=S)N(R$^a$)$_2$, —NHC(=N—C=N)NR$^a$, —NHC(=N—C=N)SR$^a$, —NHS(O)$_{n1}$R$^a$, M$^a$, —(C$_1$-C$_6$ alkylene)-B(OH)$_2$, —(C$_1$-C$_6$ alkylene)-S(O)$_{n1}$R$^a$, —(C$_1$-C$_6$ alkylene)-N(R$^a$)$_2$, —(C$_1$-C$_6$ alkylene)-C(=O)N(R$^a$)$_2$, —(C$_1$-C$_6$ alkylene)-NHC(=O)R$^a$, —(C$_1$-C$_6$ alkylene)-NHC(=O)OR$^a$, —(C$_1$-C$_6$ alkylene)-NHC(=O)C(=O)N(R$^a$)$_2$, —(C$_1$-C$_6$ alkylene)-NHC(=O)C(=O)OR$^a$, —(C$_1$-C$_6$ alkylene)-NHC(=O)N(R$^a$)$_2$, —(C$_1$-C$_6$ alkylene)-NHC(=O)NR$^a$C(=O)N(R$^a$)$_2$, —(C$_1$-C$_6$ alkylene)-NHC(=O)NRAS(O)$_2$OR$^a$, —(C$_1$-C$_6$ alkylene)-NHC(=O)NR$^a$S(O)$_2$N(R$^a$)$_2$, —(C$_1$-C$_6$ alkylene)-NHC(=S)N(R$^a$)$_2$, —(C$_1$-C$_6$ alkylene)-NHC(=N—C=N)NR$^a$, —(C$_1$-C$_6$ alkylene)-NHC(=N—C=N)SR$^a$, —(C$_1$-C$_6$ alkylene)-NHS(O)$_{n1}$R$^a$, —(C$_1$-C$_6$ alkylene)-M$^a$, —OM$^a$, —SM$^a$, or —N(R$^a$)M$^a$;

R$^a$ at each occurrence is independently hydrogen, C$_1$-C$_6$ alkyl, C$_6$-C$_{10}$ aryl, 5-10 membered heteroaryl, 3-10 membered non-aromatic heterocyclyl, C$_3$-C$_{10}$ cycloalkyl, or C$_5$-C$_{10}$ cycloalkenyl, wherein the C$_1$-C$_6$ alkyl, the C$_6$-C$_{10}$ aryl, the 5-10 membered heteroaryl, the 3-10 membered non-aromatic heterocyclyl, the C$_3$-C$_{10}$ cycloalkyl and the C$_5$-C$_{10}$ cycloalkenyl are each independently unsubstituted or substituted with one or two selected from the group consisting of amino, hydroxyl, C$_1$-C$_4$ alkoxy, C$_1$-C$_6$ alkyl, C$_3$-C$_{10}$ cycloalkyl, and CN;

M$^a$ at each occurrence is independently C$_6$-C$_{10}$ aryl, 5-10 membered heteroaryl, 3-10 membered non-aromatic heterocyclyl, C$_3$-C$_{10}$ cycloalkyl, or C$_3$-C$_{10}$ cycloalkenyl, wherein the C$_6$-C$_{10}$ aryl, the 5-10 membered heteroaryl, the 3-10 membered non-aromatic heterocyclyl, the C$_3$-C$_{10}$ cycloalkyl, and the C$_3$-C$_{10}$ cycloalkenyl are each independently unsubstituted or substituted with one or two selected from the group consisting of halogen, C$_1$-C$_4$ alkyl, C$_1$-C$_4$ alkoxy, and —CN;

n1 at each occurrence is independently 0, 1 or 2;

R is each independently hydrogen, C$_1$-C$_{10}$ alkyl, C$_6$-C$_{10}$ aryl, 5-10 membered heteroaryl, 3-10 membered non-aromatic heterocyclyl, C$_3$-C$_{10}$ cycloalkyl, or C$_3$-C$_{10}$ cycloalkenyl, wherein the C$_1$-C$_{10}$ alkyl, the C$_6$-C$_{10}$ aryl, the 5-10 membered heteroaryl, the 3-10 membered non-aromatic heterocyclyl, the C$_3$-C$_{10}$ cycloalkyl, and the C$_3$-C$_{10}$ cycloalkenyl are each independently unsubstituted or substituted with 1 to 4 M$^d$s;

M$^d$ at each occurrence is independently C$_1$-C$_6$ alkyl, C$_2$-C$_6$ alkenyl, C$_2$-C$_6$ alkynyl, halogen, C$_1$-C$_6$ haloalkyl, —CN, NO$_2$, SCF$_3$, oxo, —OM$^e$, —OC(O)M$^h$, —OC(O)NM$^f$M$^g$, —SM$^e$, —S(O)$_2$M$_e$, —S(O)$_2$NM$^f$M$^g$, —C(O)M$^e$, —C(O)-(5-10 membered monocyclic heterocyclic ring), —C(O)-(5-10-membered monocyclic heteroaryl), —C(O)OM$^e$, —C(O)NM$^f$M$^g$, —NM$^f$M$^g$, —N(M$^e$)C(O)M$^h$, —N(M$^e$)S(O)$_2$M, —N(M)C(O)OM$^h$, —N(M)C(O)NM$^f$M$^g$, —(C$_1$-C$_6$ alkylene)-OM$^e$, —(C$_1$-C$_6$ alkylene)-OC(O)M$^h$, —(C$_1$-C$_6$ alkylene)-OC(O)NM$^f$M$^g$, —(C$_1$-C$_6$ alkylene)-S(O)$_2$M$^e$, —(C$_1$-C$_6$ alkylene)-S(O)$_2$NM$^f$M$^9$, —(C$_1$-C$_6$ alkylene)-C(O)M$^e$, —(C$_1$-C$_6$ alkylene)-C(O)OM$^h$, —(C$_1$-C$_6$ alkylene)-C(O)NM$^f$M$^g$, —(C$_1$-C$_6$ alkylene)-NM$^f$M$^g$, —(C$_1$-C$_6$ alkylene)-N(M$^e$)C(O)M, —(C$_1$-C$_6$ alkylene)-N(M$^e$)S(O)$_2$M$^h$, —(C$_1$-C$_6$ alkylene)-N(M$^e$)C(O)OM$^h$, —(C$_1$-C$_6$ alkylene)-N(M$^e$)C(O)NM$^f$M$^g$, —(C$_1$-C$_6$ alkylene)-CN, C$_6$-C$_{10}$ aryl, 5-10 membered heteroaryl, 3-10 membered non-aromatic heterocyclyl, C$_3$-C$_{10}$ cycloalkyl, or C$_3$-C$_{10}$ cycloalkenyl, wherein the C$_6$-C$_{10}$ aryl, the 5-10 membered heteroaryl, the 3-10 membered non-aromatic heterocyclyl, the C$_3$-C$_{10}$ cycloalkyl and the C$_3$-C$_{10}$ cycloalkenyl are each independently unsubstituted or substituted by one or two substituents each independently selected from the group consisting of halogen, C$_1$-C$_4$ alkyl, C$_1$-C$_4$ alkoxy, and —CN;

M$^e$, M$^f$, M$^g$ and M$^h$ at each occurrence are each independently hydrogen, C$_1$-C$_6$ alkyl, C$_1$-C$_6$ haloalkyl, C$_3$-C$_{10}$ cycloalkyl, C$_6$-C$_{10}$ aryl, 5-10 membered heteroaryl, or 3-10 membered non-aromatic heterocyclyl, wherein the Ct-Co alkyl, the C$_1$-C$_{10}$ cycloalkyl, the C$_6$-C$_{10}$ aryl, the 5-10 membered heteroaryl, and the 3-10 membered non-aromatic heterocyclyl are each independently unsubstituted or substituted by one or two substituents each independently selected from the group consisting of halogen, hydroxy, C$_1$-C$_4$ alkyl, C$_1$-C$_4$ alkoxy, —CN, —S(O)$_2$(C$_1$-C$_4$ alkyl), and —C(O)(C$_1$-C$_4$ alkyl); or two M$^d$s together with the ring atoms to which they are connected, form a 3-8 membered saturated or unsaturated ring.

2. The compound, or a pharmaceutically acceptable salt, stereoisomer, enantiomer, diastereomer, atropisomer, optical isomer, racemate, polymorph, solvate or isotopically labeled compound thereof according to claim 1, wherein, the compound of formula I is selected from the group consisting of the compounds represented by formulae Ia and Ib:

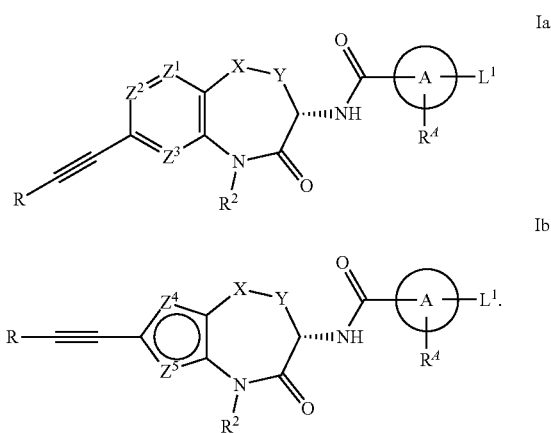

Z$^1$ is N, CH, C(CH$_3$), or C(halogen);

Z$^2$ is N or CR$^1$;

Z$^3$ is N, CH, C(CH$_3$), or C(halogen); and Z$^1$, Z$^2$, Z$^3$ are not N at the same time;

Z$^4$ is O, CR$^1$, S, N, or NR$^1$;

Z$^5$ is O, CR$^1$, S, N, or NR$^1$;

A, L$^1$, X, Y, R, R$^A$, R$^1$ and R$^2$ are the same as defined in the formula I of claim 1.

3. The compound, or a pharmaceutically acceptable salt, stereoisomer, enantiomer, diastereomer, atropisomer, optical isomer, racemate, polymorph, solvate or isotopically labeled compound thereof according to claim 1, wherein, the compound of formula I is selected from the group consisting of the compounds represented by formulae Ic, Id, Ie and If:

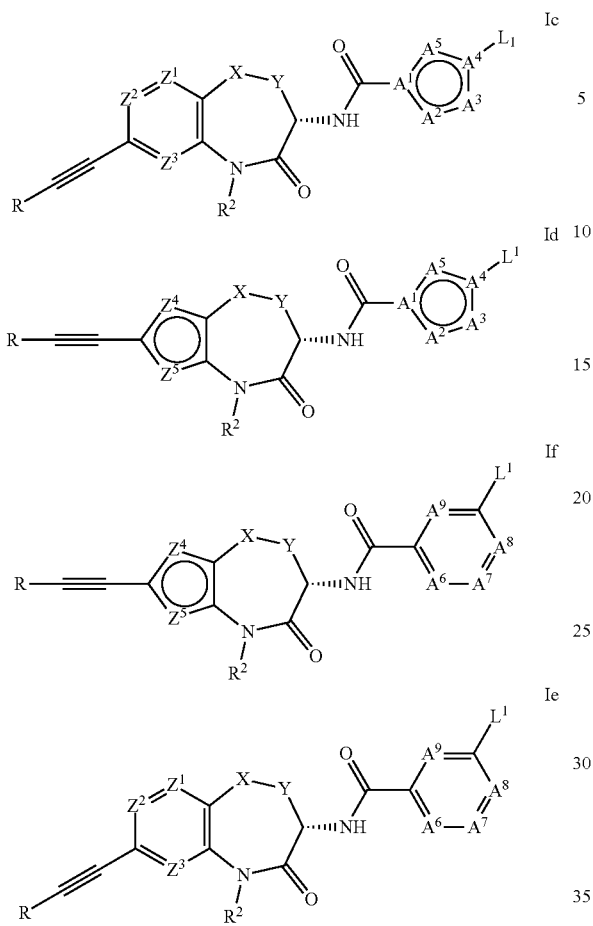

$Z^1$ is N, CH, C(CH$_3$), or C(halogen);
$Z^2$ is N or CR$^1$;
$Z^3$ is N, CH, C(CH$_3$), or C(halogen); and $Z^1$, $Z^2$, $Z^3$ are not N at the same time;
$Z^4$ is O, CR$^1$, S, N, or NR$^1$;
$Z^5$ is O, CR$^1$, S, N, or NR$^1$;
$A^1$ is C;
$A^4$ is C or N; and
$A^2$, $A^3$ and $A^5$ are each independently selected from the group consisting of CR$^4$, O, S, N and NR$^4$, so as to form a ring moiety of furyl, thienyl, isoxazolyl, oxazolyl, thiazolyl, oxadiazolyl, pyrrolyl, pyrazolyl, imidazolyl, triazolyl, or tetrazolyl, wherein at most one R$^4$ is not hydrogen;
$A^6$, $A^7$, $A^8$ and $A^9$ are each independently CR$^4$, wherein at most one R$^4$ is not hydrogen; or
one of $A^6$, $A^7$, $A^8$ and $A^9$ is N, and the others of $A^6$, $A^7$, $A^8$ and $A^9$ are CH; or
one of $A^6$, $A^7$, $A^8$ and $A^9$ is N$^+$—O$^-$, and the others of $A^6$, $A^7$, $A^8$ and $A^9$ are CH;
$L^1$, X, Y, R, R$^4$, R$^1$ and R$^2$ are the same as defined in the formula I of claim 1.

4. The compound, or a pharmaceutically acceptable salt, stereoisomer, enantiomer, diastereomer, atropisomer, optical isomer, racemate, polymorph, solvate or isotopically labeled compound thereof according to claim 1, wherein, the compound of formula I is selected from the group consisting of the compounds represented by formulae Ig and Ih:

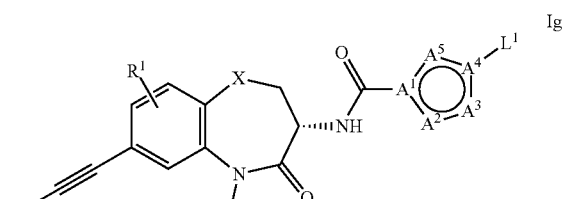

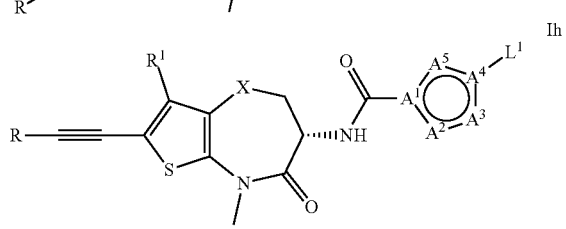

R$^1$ is H, halogen, —OH, —CN, C$_1$-C$_6$ alkyl, C$_1$-C$_6$ haloalkyl, C$_1$-C$_6$ alkoxy, or C$_1$-C$_6$ haloalkoxy;
X is S;
$A^1$ is C;
$A^4$ is C or N; and
$A^2$, $A^3$ and $A^5$ are each independently selected from the group consisting of CR$^4$, O, S, N and NR$^4$, so as to form a ring moiety of furyl, thienyl, isoxazolyl, oxazolyl, thiazolyl, oxadiazolyl, pyrrolyl, pyrazolyl, imidazolyl, triazolyl, or tetrazolyl, wherein at most one R$^4$ is not hydrogen;
$L^1$, R, and R$^4$ are the same as defined in the formula I of claim 1.

5. The compound, or a pharmaceutically acceptable salt, stereoisomer, enantiomer, diastereomer, atropisomer, optical isomer, racemate, polymorph, solvate or isotopically labeled compound thereof according to claim 1, wherein, the compound of formula I is selected from the group consisting of the compounds represented by formulae Ii and Ij:

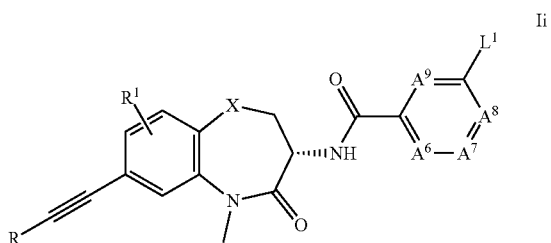

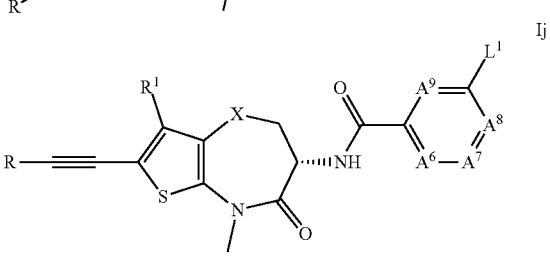

R$^1$ is H, halogen, —OH, —CN, C$_1$-C$_6$ alkyl, C$_1$-C$_6$ haloalkyl, C$_1$-C$_6$ alkoxy, or C$_1$-C$_6$ haloalkoxy;
X is S;
$A^6$, $A^7$, $A^8$ and $A^9$ are each independently CR$^4$, wherein at most one R$^4$ is not hydrogen; or
one of $A^6$, $A^7$, $A^8$ and $A^9$ is N, and the others of $A^6$, $A^7$, $A^8$ and $A^9$ are CH; or one of $A^6$, $A^7$, $A^8$ and $A^9$ is $N^+$—$O^-$, and the others of $A^6$, $A^7$, $A^8$ and $A^9$ are CH;

$L^1$, R, $R^A$ are the same as defined in the formula I of claim 1.

6. The compound, or a pharmaceutically acceptable salt, stereoisomer, enantiomer, diastereomer, atropisomer, optical isomer, racemate, polymorph, solvate or isotopically labeled compound thereof according to claim 1, wherein, the compound of formula I is selected from the group consisting of the compounds represented by the formula Il:

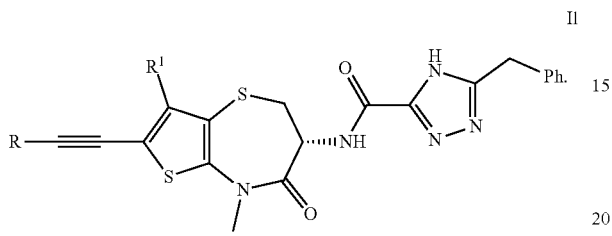

Il $R^1$ is H, F, Cl, $CH_3$, or $CH_2CH_3$;

R is isoxazolyl, oxazolyl, thiazolyl, oxadiazolyl, pyrrolyl, pyrarolyl, imidazolyl, triazolyl, pyridinyl, pyrimidinyl, $C_3$-$C_6$ cycloalkyl,

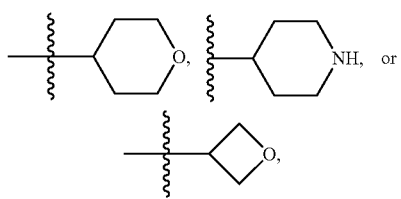

each independently being unsubstituted or substituted with one substituent selected from the group consisting of F, Cl, methyl, ethyl, isopropyl and cyclopropyl; or the compound of the formula I is selected from the group consisting of the compounds represented by formulae Im and In:

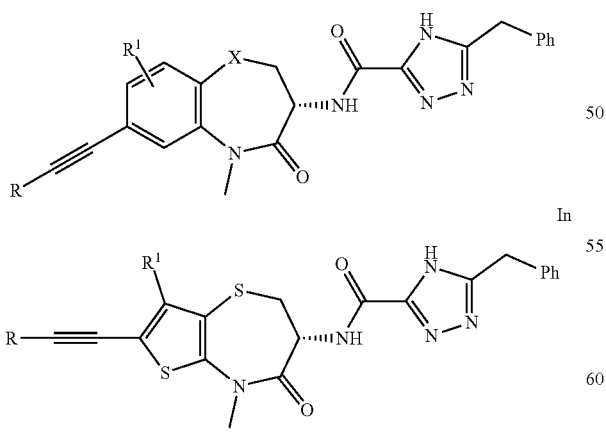

$R^1$ is H, F, Cl, $CH_3$, or $CH_2CH_3$;
X is S;
R is $C_1$-$C_6$ alkyl, $C_6$-$C_{10}$ aryl, 5-10 membered heteroaryl, 3-7 membered non-aromatic heterocyclyl, $C_3$-$C_8$ cycloalkyl, or $C_5$-$C_8$ cycloalkenyl, wherein the $C_1$-$C_4$ alkyl, the $C_6$-$C_{10}$ aryl, the 5-10 membered heteroaryl, the 3-7 membered non-aromatic heterocyclyl, the $C_3$-$C_8$ cycloalkyl, and the $C_5$-$C_8$ cycloalkenyl are each independently unsubstituted or substituted with 1 to 4 $M^d$s $M^d$ is selected from the group consisting of F, Cl, methyl, ethyl, propyl, butyl, trifluoromethyl, —($C_1$-$C_6$ alkylene)-OH, isopropyl, cyclopropyl, hydroxyl, methoxy, amino, methylamino, dimethylamino, diethylamino, $C_6$-$C_{10}$ aryl, 5-10 membered heteroaryl, 3-6 membered non-aromatic heterocyclyl; wherein the $C_6$-$C_{10}$ aryl, the 5-10 membered heteroaryl and the 3-6 membered non-aromatic heterocyclyl are each independently unsubstituted or substituted by one or two substituents each independently selected from the group consisting of halogen, $C_1$-$C_4$ alkyl, $C_1$-$C_4$ alkoxy, and —CN, or two $M^a$s together with the ring atoms to which they are connected form a 3-8 membered saturated or unsaturated ring.

7. The compound, or a pharmaceutically acceptable salt, stereoisomer, enantiomer, diastereomer, atropisomer, optical isomer, racemate, polymorph, solvate or isotopically labeled compound thereof according to claim 1, wherein, the compound of formula I is selected from the group consisting of the following compounds:

ZB-R-44

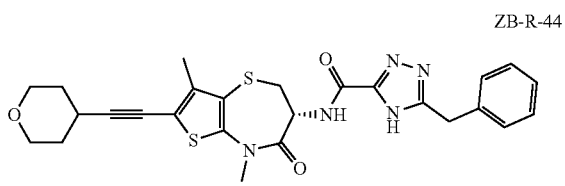

ZB-R-45

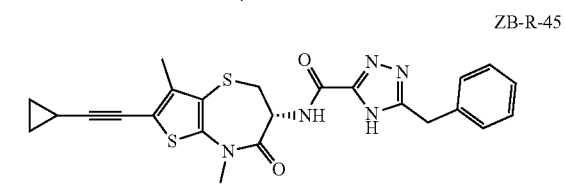

ZB-R-46

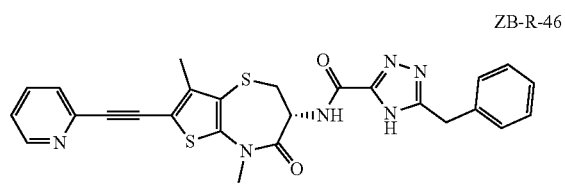

ZB-R-47

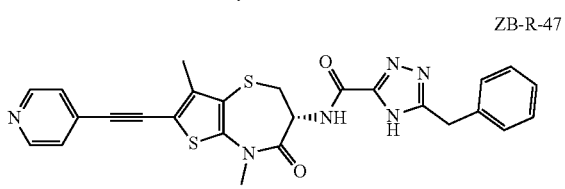

ZB-R-42

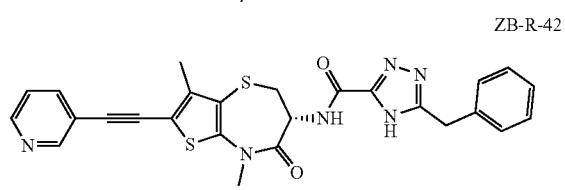

-continued
ZB-R-48
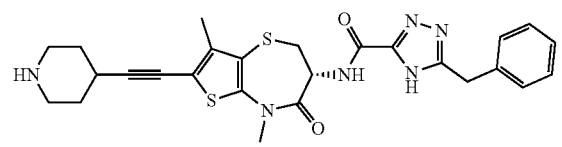
ZB-R-39
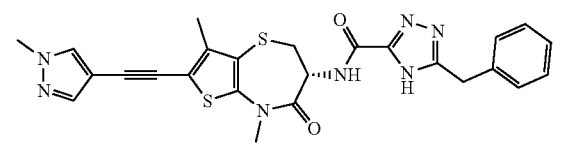
ZB-R-1
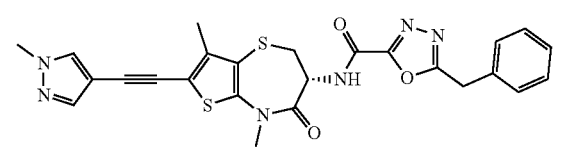
ZB-R-2
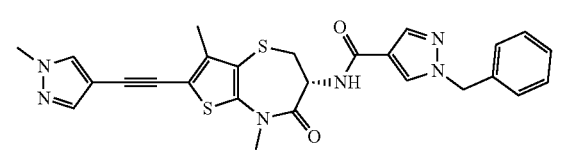
ZB-R-3
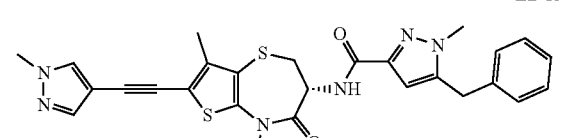
ZB-R-4
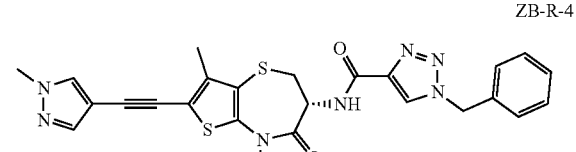
ZB-R-5
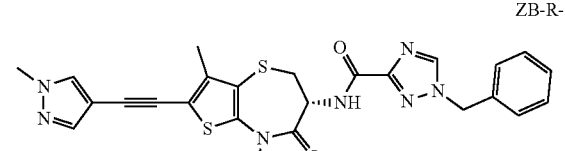
ZB-R-6
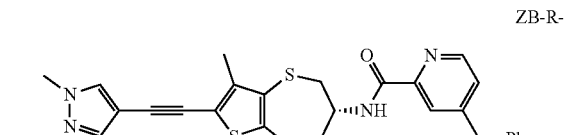
ZB-R-82
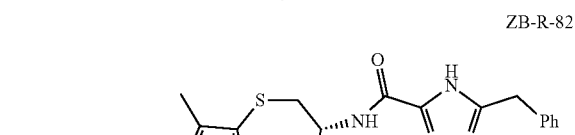
-continued
ZB-R-83
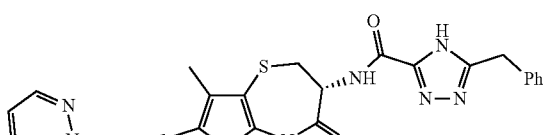
ZB-R-84
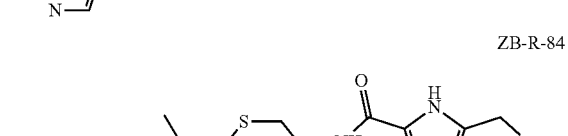
ZB-R-85
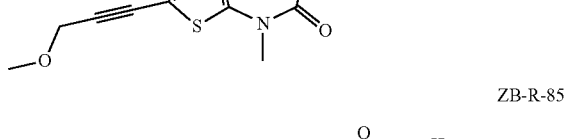
ZB-R-86
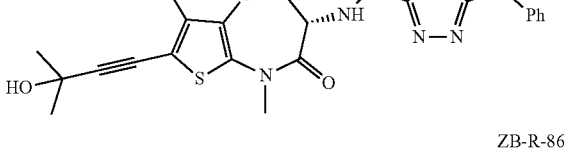
ZB-R-87
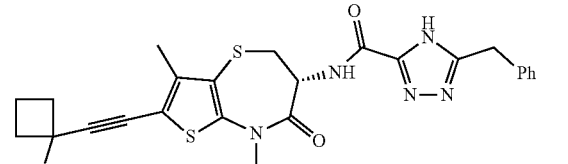
ZB-R-88
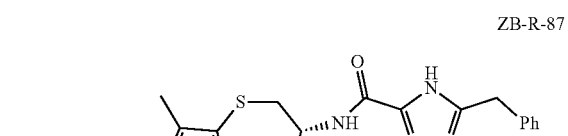
ZB-R-89
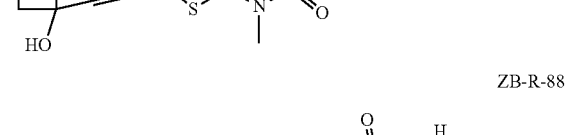

ZB-R-90

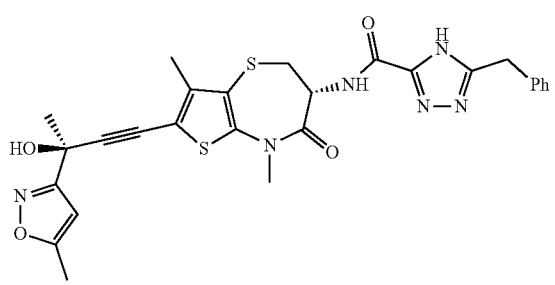

ZB-R-33

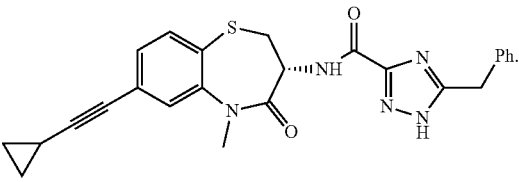

ZB-R-30

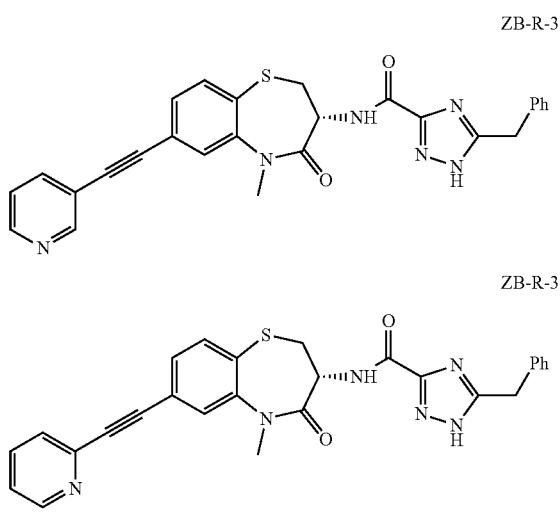

ZB-R-31

ZB-R-32

8. A pharmaceutical composition comprising a therapeutically effective amount of one or more selected from the group consisting of the compound of formula (C), and pharmaceutically acceptable salts, enantiomers, diastereomers, atropisomers, optical isomers, racemates, polymorphs, solvates and isotopically labeled compounds thereof according to claim 1, and optionally, a pharmaceutically acceptable carrier.

9. Method for treating a disease or disorder or condition in a subject, comprising the step of administrating the compound, or a pharmaceutically acceptable salt, stereoisomer, enantiomer, diastereomer, atropisomer, optical isomer, racemate, polymorph, solvate or isotopically labeled compound thereof according to claim 1 to the subject, wherein the disease or disorder or condition is selected from the group consisting of inflammatory bowel disease, Crohn's disease, ulcerative colitis, psoriasis, retinal detachment, retinitis pigmentosa, macular degeneration, pancreatitis, atopic dermatitis, rheumatoid arthritis, spondyloarthritis, gout, SoJIA, systemic lupus erythematosus, Sjogren's syndrome, systemic scleroderma, antiphospholipid syndrome, vasculitis, osteoarthritis, non-alcoholic fatty liver hepatitis, autoimmune hepatitis, autoimmune hepatobiliary disease, primary sclerosed cholangitis, nephritis, celiac disease, autoimmune ITP, transplant rejection, solid organ ischemia-reperfusion injury, sepsis, systemic inflammatory response syndrome, cerebrovascular accident, myocardial infarction, Huntington's disease, Alzheimer's disease, Parkinson's disease, allergic disease, asthma, multiple sclerosis, Type I diabetes, Wegener's granulomatosis, pulmonary sarcoidosis, Behcet's disease, interleukin-I converting enzyme-related fever syndrome, chronic obstructive pulmonary disease, tumor necrosis factor receptor-related periodic syndrome, and periodontitis.

* * * * *